United States Patent
Wood et al.

(10) Patent No.: US 8,391,960 B2
(45) Date of Patent: *Mar. 5, 2013

(54) SCANNED LASER VEIN CONTRAST ENHANCER

(75) Inventors: Fred Wood, Medford, NY (US); Ron Goldman, Cold Spring Harbor, NY (US); Stephen Conlon, Cold Spring Harbor, NY (US); Vincent Luciano, Farmingville, NY (US)

(73) Assignee: AccuVein Inc.

( * ) Notice: Subject to any disclaimer, the term of this patent is extended or adjusted under 35 U.S.C. 154(b) by 1260 days.

This patent is subject to a terminal disclaimer.

(21) Appl. No.: 11/807,064

(22) Filed: May 25, 2007

(65) Prior Publication Data

US 2008/0287806 A1 Nov. 20, 2008

Related U.S. Application Data

(63) Continuation-in-part of application No. 11/478,322, filed on Jun. 29, 2006.

(60) Provisional application No. 60/817,623, filed on Jun. 29, 2006.

(51) Int. Cl.
*A61B 6/00* (2006.01)

(52) U.S. Cl. ............ 600/473; 600/407; 600/476; 606/1; 606/2; 606/10; 606/11; 606/12; 606/13; 606/17; 606/18

(58) Field of Classification Search ............... 600/407, 600/473, 476; 606/1, 2, 10, 11, 12, 13, 17, 606/18

See application file for complete search history.

(56) References Cited

U.S. PATENT DOCUMENTS

| | | | | |
|---|---|---|---|---|
| 4,321,930 A | * | 3/1982 | Jobsis et al. | 600/344 |
| 4,502,075 A | | 2/1985 | DeForest et al. | |
| 4,619,249 A | | 10/1986 | Landry | |
| 4,817,622 A | * | 4/1989 | Pennypacker et al. | 600/473 |
| 5,214,458 A | | 5/1993 | Kanai | |
| 5,406,070 A | | 4/1995 | Edgar et al. | |

(Continued)

FOREIGN PATENT DOCUMENTS

| | | |
|---|---|---|
| FR | 2289149 | 5/1976 |
| GB | 1507329 | 4/1978 |

(Continued)

OTHER PUBLICATIONS

Wiklof, Chris. Display Technology Spawns Laser Camera. Dec. 1, 2004. Laser Focus World.*

(Continued)

*Primary Examiner* — James Kish

(74) *Attorney, Agent, or Firm* — Thomas A. O'Rourke; Bodner & O'Rourke, LLP

(57) ABSTRACT

The present invention is a Miniature Vein Enhancer that includes a Miniature Projection Head. The Miniature Projection Head may be operated in one of three modes, AFM, DBM, and RTM. The Miniature Projection Head of the present invention projects an image of the veins of a patient, which aids the practitioner in pinpointing a vein for an intravenous drip, blood test, and the like. The Miniature projection head may have a cavity for a power source or it may have a power source located in a body portion of the Miniature Vein Enhancer. The Miniature Vein Enhancer may be attached to one of several improved needle protectors, or the Miniature Vein Enhancer may be attached to a body similar to a flashlight for hand held use. The Miniature Vein Enhancer of the present invention may also be attached to a magnifying glass, a flat panel display, and the like.

12 Claims, 37 Drawing Sheets

U.S. PATENT DOCUMENTS

| | | | |
|---|---|---|---|
| 5,519,208 A * | 5/1996 | Esparza et al. | 250/226 |
| 5,541,820 A | 7/1996 | McLaughlin | |
| 5,608,210 A | 3/1997 | Esparza et al. | |
| 5,631,976 A | 5/1997 | Bolle et al. | |
| 5,678,555 A | 10/1997 | O'Connell | |
| 5,772,593 A | 6/1998 | Hakamata | |
| 5,860,967 A | 1/1999 | Zavislan et al. | |
| 5,982,553 A * | 11/1999 | Bloom et al. | 359/627 |
| 6,061,583 A | 5/2000 | Ishihara et al. | |
| 6,135,599 A | 10/2000 | Fang | |
| 6,142,650 A * | 11/2000 | Brown et al. | 362/259 |
| 6,149,644 A | 11/2000 | Xie | |
| 6,178,340 B1 | 1/2001 | Svetliza | |
| 6,464,646 B1 * | 10/2002 | Shalom et al. | 600/549 |
| 6,542,246 B1 | 4/2003 | Toida | |
| 6,556,854 B1 | 4/2003 | Sato et al. | |
| 6,556,858 B1 * | 4/2003 | Zeman | 600/473 |
| 6,782,161 B2 | 8/2004 | Barolet et al. | |
| 6,980,852 B2 | 12/2005 | Jersey-Willuhn et al. | |
| 7,158,660 B2 * | 1/2007 | Gee et al. | 382/128 |
| 2002/0016533 A1 | 2/2002 | Marchitto | |
| 2002/0118338 A1 | 8/2002 | Kohayakawa | |
| 2005/0043596 A1 | 2/2005 | Chance | |
| 2005/0113650 A1 | 5/2005 | Pacione et al. | |
| 2005/0141069 A1 | 6/2005 | Wood et al. | |
| 2005/0143662 A1 | 6/2005 | Marchitto et al. | |
| 2005/0161051 A1 | 7/2005 | Pankratov et al. | |
| 2005/0174777 A1 | 8/2005 | Cooper et al. | |
| 2005/0175048 A1 | 8/2005 | Stern et al. | |
| 2005/0215875 A1 | 9/2005 | Khou | |
| 2005/0281445 A1 | 12/2005 | Marcotte et al. | |
| 2006/0122515 A1 | 6/2006 | Zeman | |
| 2006/0129037 A1 | 6/2006 | Kaufman et al. | |
| 2006/0232660 A1 | 10/2006 | Nakajima et al. | |
| 2006/0253010 A1 | 11/2006 | Brady et al. | |
| 2006/0271028 A1 | 11/2006 | Altshuler et al. | |
| 2007/0016079 A1 | 1/2007 | Freeman et al. | |

FOREIGN PATENT DOCUMENTS

| | | |
|---|---|---|
| JP | 2004237051 | 8/2004 |
| WO | WO 94/22370 | 10/1994 |
| WO | WO 96/39925 | 12/1996 |
| WO | WO 9826583 | 6/1998 |
| WO | WO 01/82786 | 11/2001 |
| WO | WO 03/009750 | 2/2003 |
| WO | WO 2007/078447 A2 | 7/2007 |

OTHER PUBLICATIONS

The Exploratorium. "To Do & Notice: Getting the Feel of your Hand." www.exploratorium.edu, Jul. 23, 1997. pp. 1-3.*

* cited by examiner

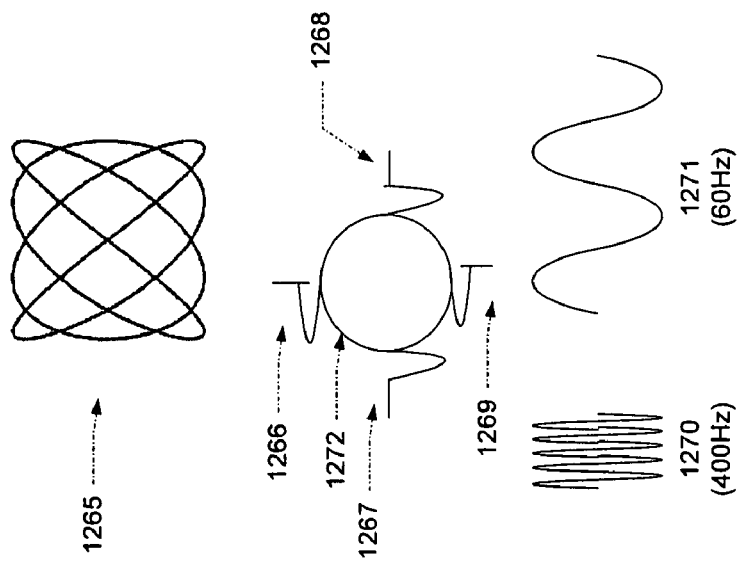
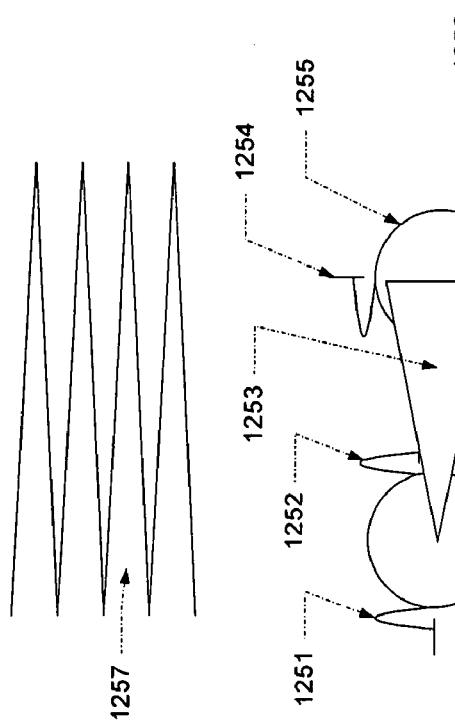

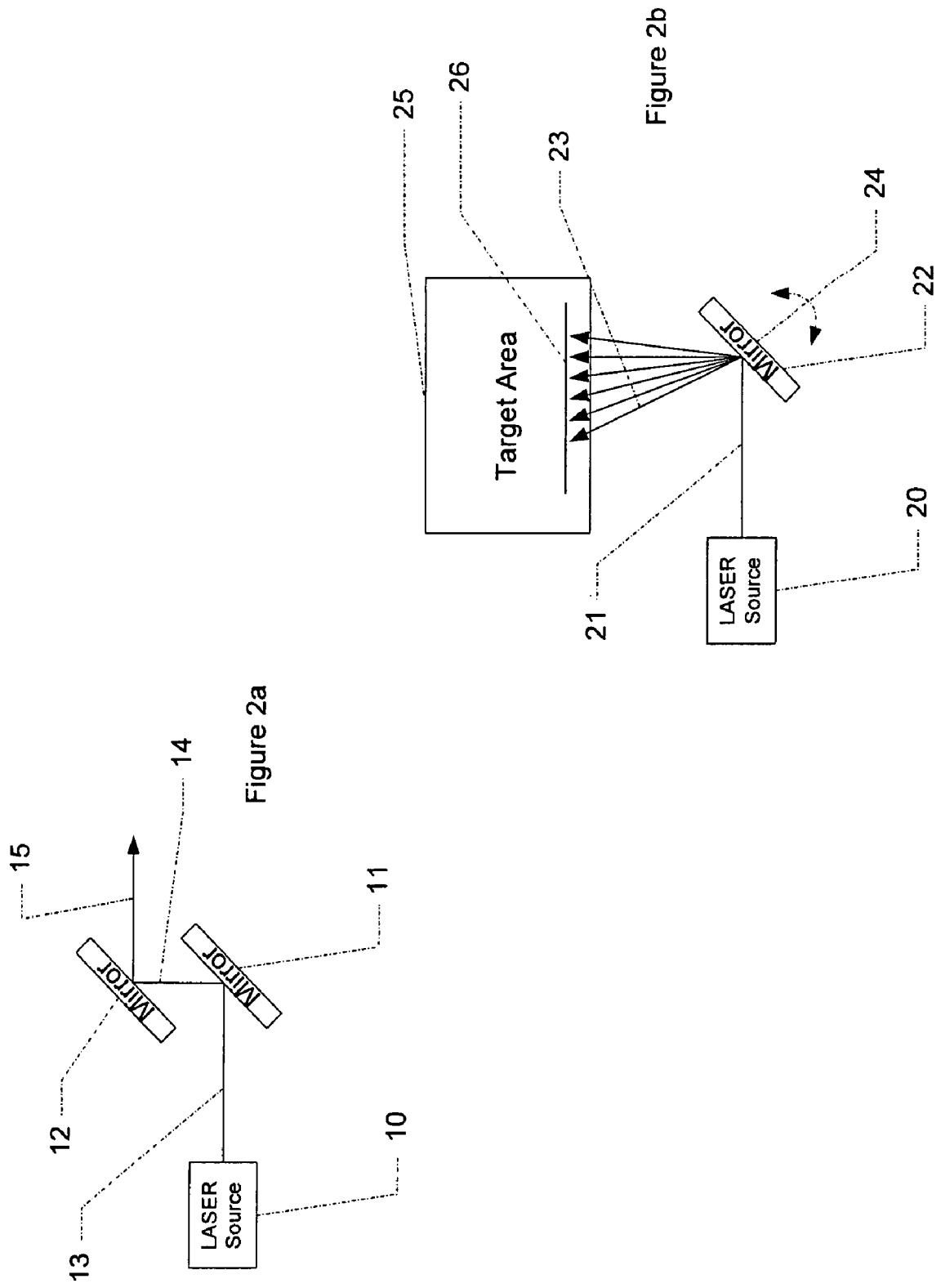

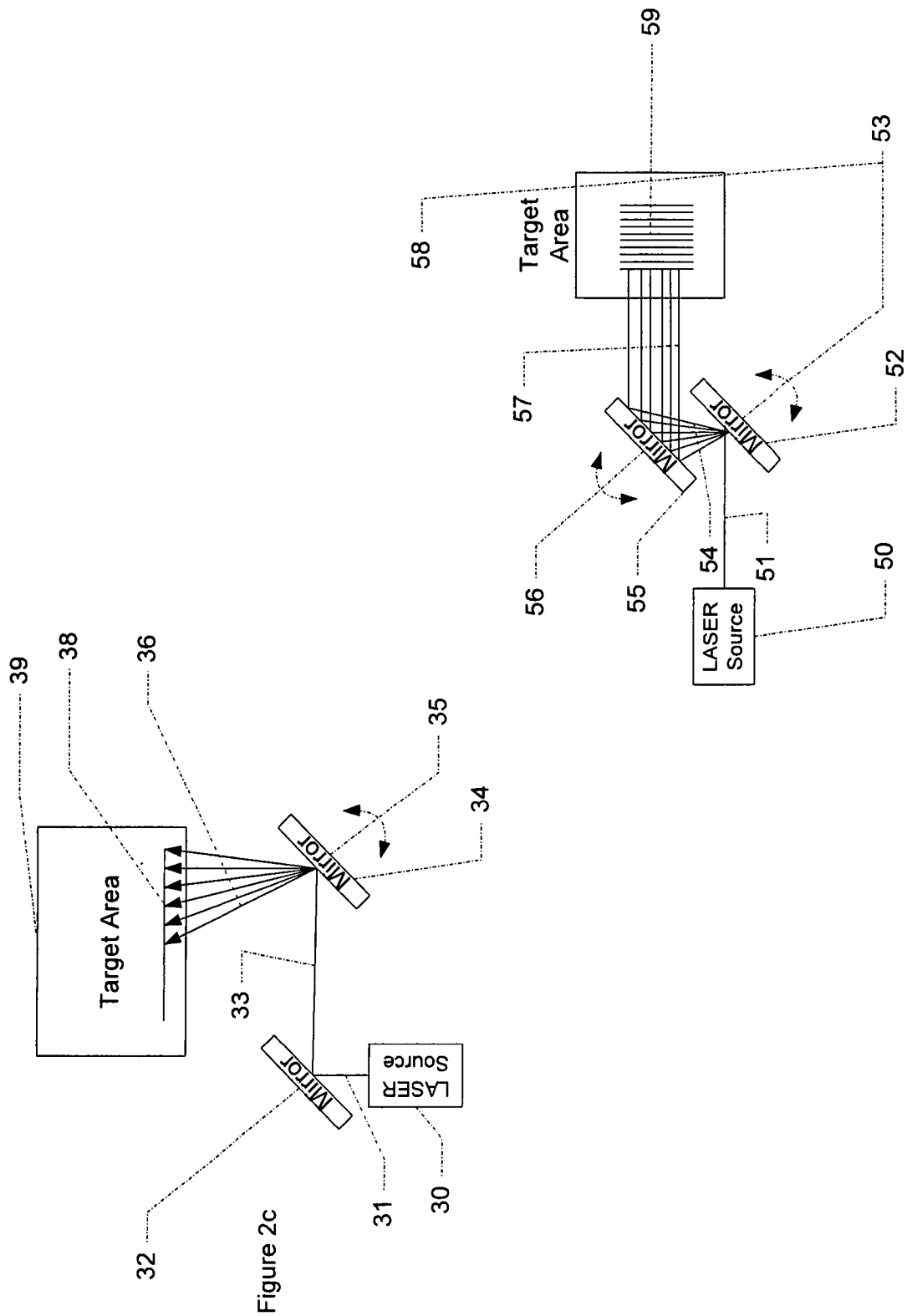

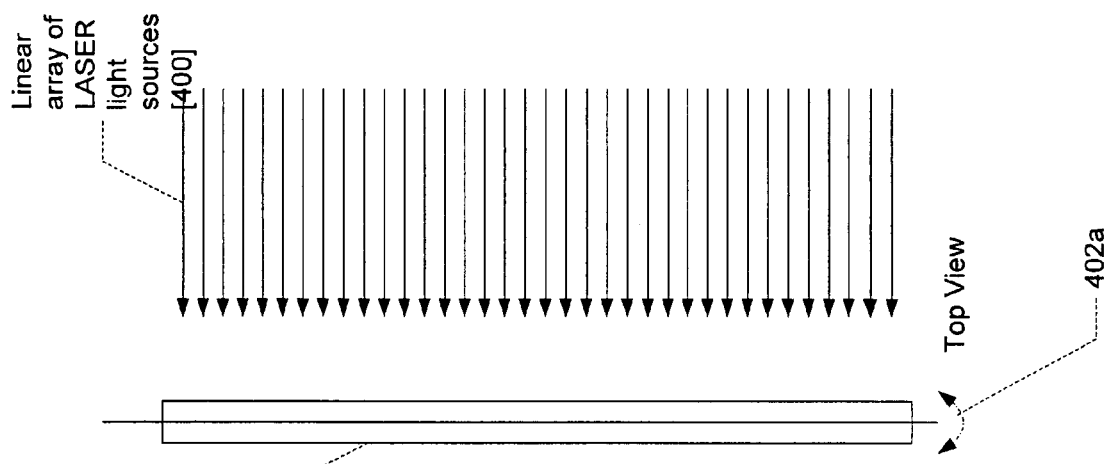
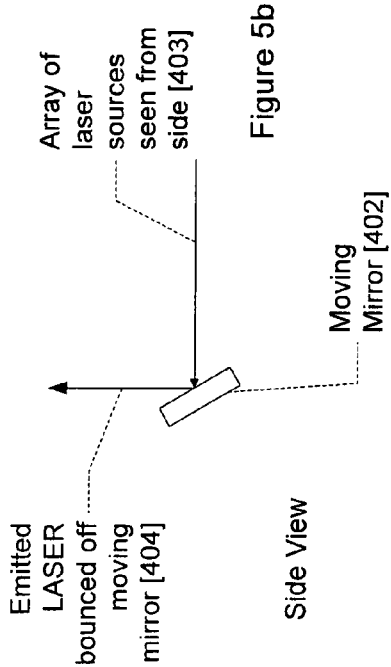

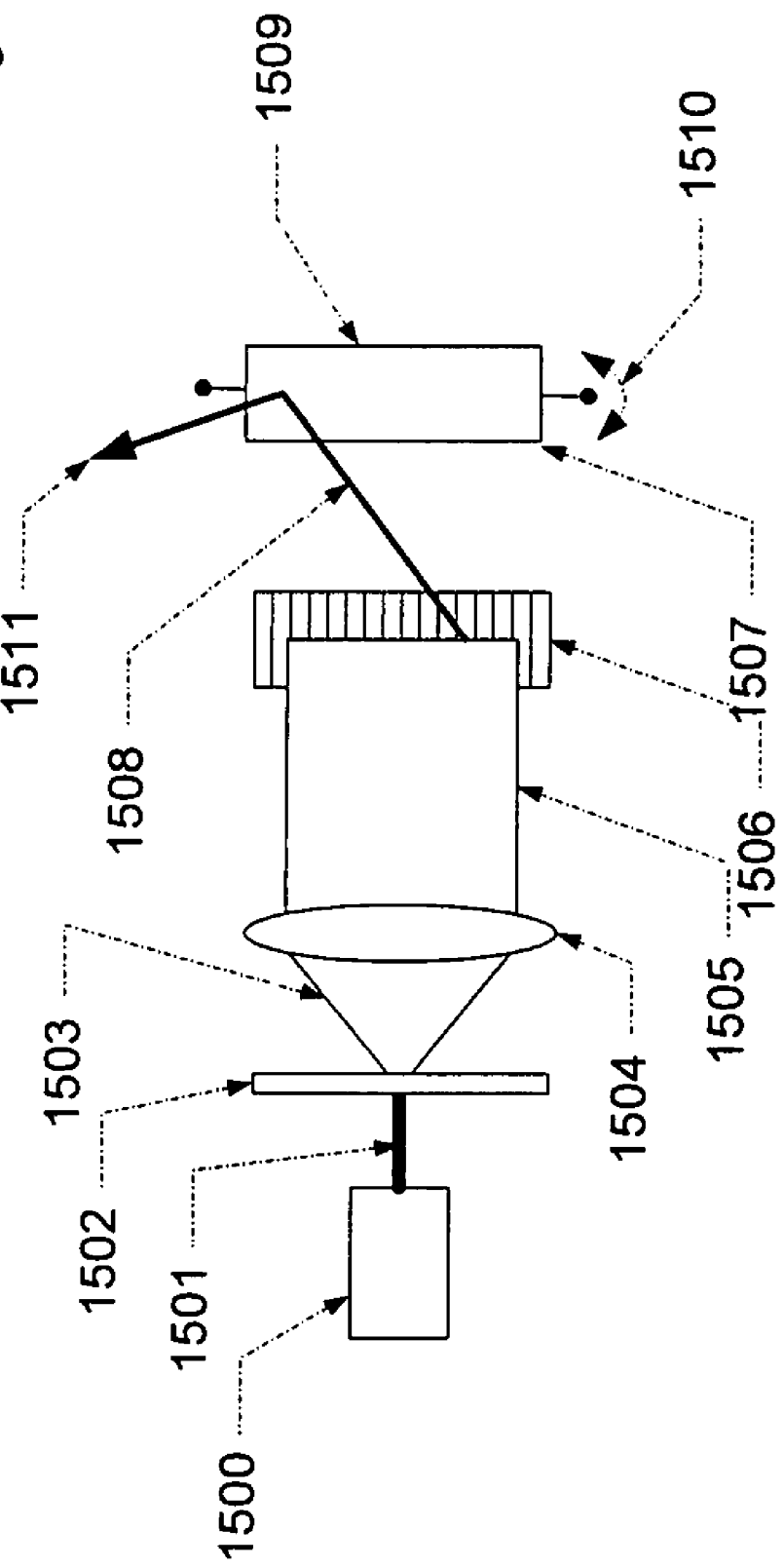

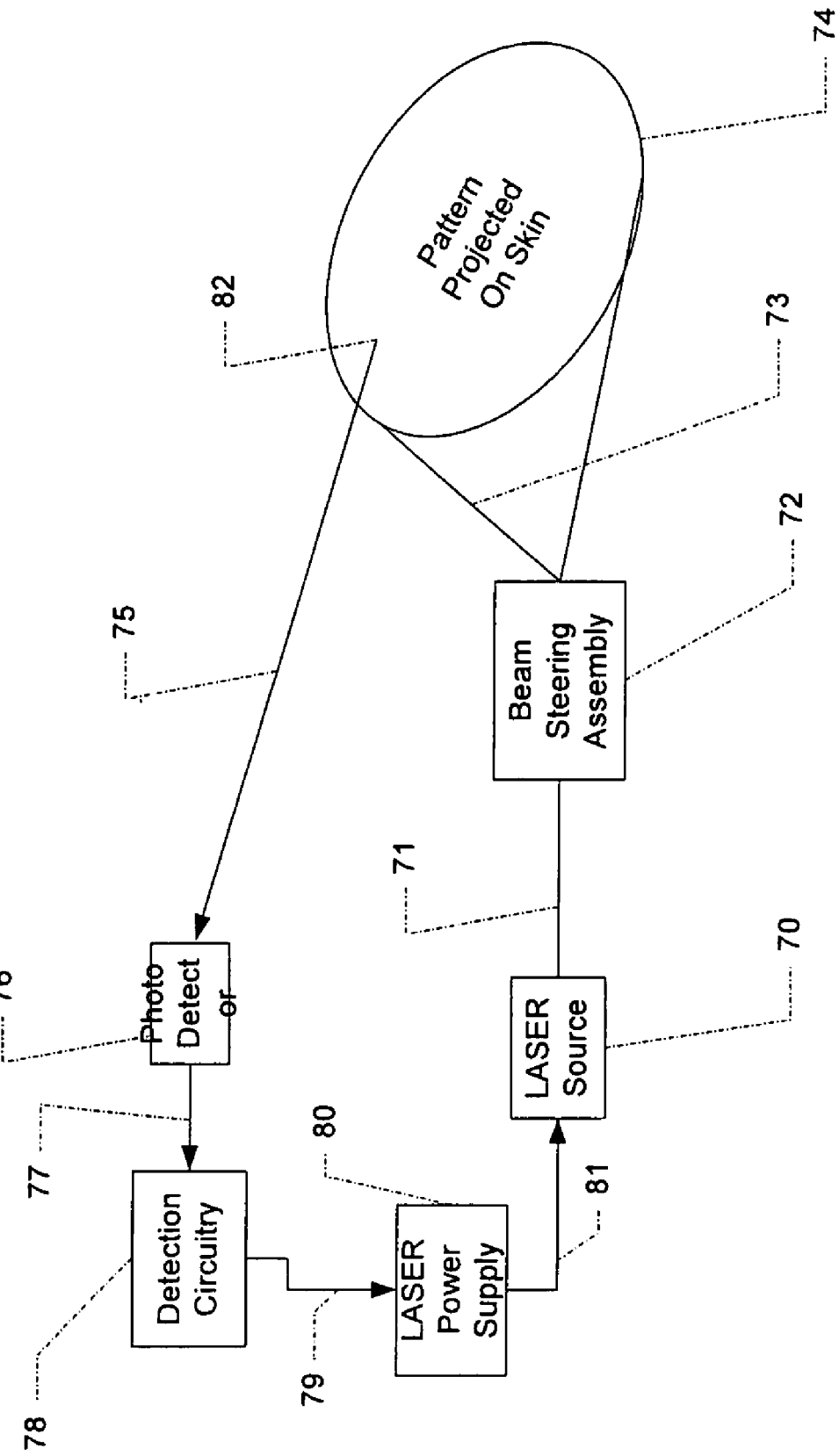

SCANNED LASER VEIN CONTRAST ENHANCER

This application is a continuation in part of application Ser. No. 11/478,322, filed on Jun. 29, 2006 and also claims priority on provisional patent application entitled Three Dimensional Imaging of Veins, Application No. 60/817,623, also filed on Jun. 29, 2006, all disclosures of which are hereby incorporated by reference.

FIELD OF INVENTION

The invention described herein relates generally to an imaging device, in particular, an imaging means for enhancing visualization of components covered by living tissue thin opaque films. More particularly, the present invention is directed to enhancing the visualization of veins, arteries and other subcutaneous structures of the body for inter alia facilitating fluid insertion into or extraction from the body or otherwise visualizing subcutaneous structures for diagnosis of the medical condition of a patient or administration of medical treatment to a patient.

BACKGROUND OF THE INVENTION

A visit to a doctor's office, a clinic or a hospital may necessitate vascular access that is, the insertion of a needle or catheter into a patient's vein or artery. These procedures may be required for many reasons including: to administer fluids, drugs or solutions, to obtain and monitor vital signs, to place long-term access devices, and to perform simple venipunctures. Vascular access ranks as the most commonly performed invasive medical procedure in the U.S.—over 1.4 billion procedures annually—as well as the top patient complaint among clinical procedures. The overwhelming majority of vascular access procedures is performed without the aid of any visualization device and relies on what is observed through the patient's skin and by the clinician's ability to feel the vessel—basically educated guesswork.

Medical literature reports the following statistics: 28% first attempt IV failure rate in normal adults, 44% first attempt IV failure in pediatrics, 43% of pediatric IVs require three or more insertion attempts, 23% to 28% incidence of extravasations/infiltration, 12% outright failure rate in cancer patients, 25% of hospital in-patients beyond three days encounter difficult access. The miniature vein enhancer of the present invention may be used by a practitioner to locate a vein and is particularly useful when trying to locate a vein in the very old, very young or obese patients. More than fifty percent of attempts to find a vein in the elderly, who have a generally high percentage of loose, fatty tissue, and in children, who have a generally high percentage of small veins and "puppy fat", are unsuccessful. The present invention is aimed at reducing and/or preventing the discomfort and delay associated with botched attempts to pierce veins for injections and blood tests. In addition, the present invention can cut the time it takes to set up potentially life-saving intravenous drip. During venous penetration, whether for an injection or drip, it is essential to stick a vein in exactly the right location. If a practitioner is only slightly off center, the needle will more than likely just roll off and require a re-stick.

Other Approaches

It is known in the art to use an apparatus to enhance the visual appearance of the veins in a patient to facilitate insertion of needles into the veins. An example of such a system is described in U.S. Pat. Nos. 5,969,754 and 6,556,858 incorporated herein by reference as well as a publication entitled "The Clinical Evaluation of Vein Contrast Enhancement". Luminetx is currently marketing such a device under the name "Veinviewer Imaging System."

The Luminetx Vein Contrast Enhancer (hereinafter referred to as LVCE) utilizes an infrared light source (generated by an array of LEDs) for flooding the region to be enhanced with infrared light. A CCD imager is then used to capture an image of the infrared light reflected off the patient. The resulting captured image is then projected by a visible light projector onto the patient in a position closely aligned with the image capture system. Given that the CCD imager and the image projector are both two dimensional, and do not occupy the same point in space, it is relatively difficult to design and build a system that closely aligns the captured image and the projected image.

A further characteristic of the LVCE is that both the imaging CCD and the projector have fixed focal lengths. Accordingly, the patient must be at a relatively fixed distance relative to the LVCE. This necessitates that the LVCE be positioned at a fixed distance from the region of the patient to be enhanced.

The combination of the size of the LVCE and the fixed focal arrangement precludes using the LVCE as small portable units that are hand held.

Other patents such as U.S. Pat. No. 6,230,046, issued to Crane et al., implement a light source for illuminating or trans-illuminating the corresponding portion of the body with light of selected wavelengths and a low-level light detector such as an image intensifier tube (including night vision goggles), a photomultiplier tube, photodiode or charge coupled device, for generating an image of the illuminated body portion, and optical filter(s) of selected spectral transmittance which can be located at the light source(s), detector, or both.

All cited references are incorporated herein by reference in their entireties. Citation of any reference is not an admission regarding any determination as to its availability as prior art to the claimed invention.

Objects of the Invention

The present invention is directed to technologies and processes associated with the use of one or more moving laser light sources to detect the presence of blood-filled structures, such as venous or arterial structures, below the surface of the skin and to project an image back on to the skin that shows the operator the pattern of detected structures. The present approach uses one or more laser light sources that are scanned over the body using mirrors and a light detector that measures the reflections of the laser light and uses the pattern of reflections to identify the targeted blood rich structures. Various preferred approaches are described for the main subsystems of the design as well as various alternative techniques for accomplishing the objects of this invention.

BRIEF DESCRIPTION OF DRAWINGS

FIG. 2 shows mirror systems for folding and scanning the lasers

FIG. 5 shows the use of an array of lasers to eliminate the need for a second moving mirror for scanning the lasers FIG. 6 shows the use of a light valve element to eliminate the need for a second moving mirror for scanning the lasers

SUMMARY OF THE INVENTION

Using One or More Lasers to Capture and Project an Image

Blood vessels, both venous and arterial, absorb red, near infrared and infrared (IR) light to a greater degree than surrounding tissues absorb those wavelengths of light. Therefore when illuminating the surface of the body with infrared light, blood rich tissues such as veins will absorb more of this light and other tissues will reflect more of this light. Analysis of this pattern of reflections enables the veins to be located. The present invention includes both a positive or negative image that is projected in the presence of a vein. Thus, a vein can be represented by a bright area and the absence of a vein can be presented as a dark area and vice versa.

A laser diode is preferred in the present invention as it emits light over a known, narrow wavelength range and when appropriately focused projects a small spot that varies very little in size over a wide range of distances. This is an effect that is commonly seen in laser pointers and laser gun sights.

Figure 16:
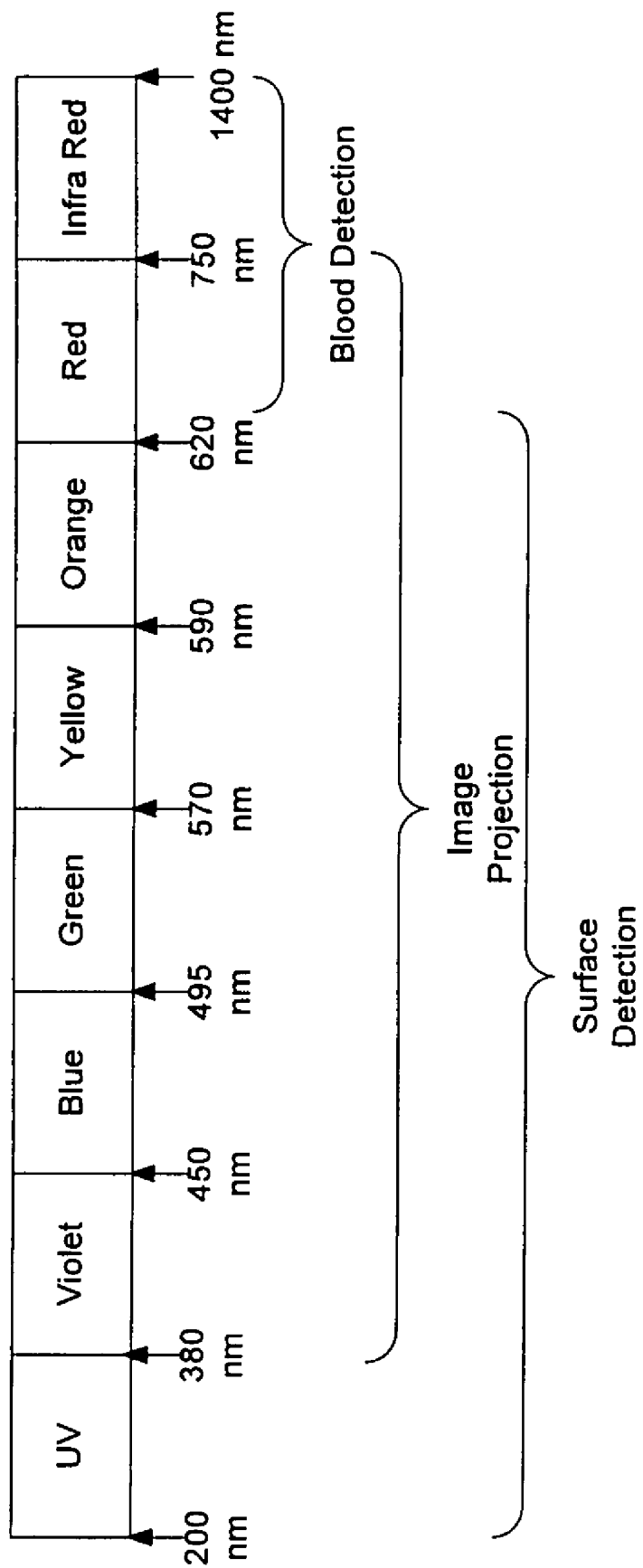
FIG. 16 shows the preferred wavelengths for various elements in the system.

1. In addition to a laser diode, the laser light used in the present invention can be generated by other laser light emitting elements including but not limited to VCSEL lasers, other semiconductor lasers and other solid state lasers. In the present invention a narrow wavelength of light is emitted producing a constant spot size even when the range to the target varies. The narrow wavelength allows a laser diode or diodes to be selected that have the desired characteristics of the ability to detect blood through differential absorption and the ability for a human eye to detect the reflected light. As will be discussed, certain embodiments may require differing tradeoffs in light wavelength. Additionally, the same characteristics of the laser that make it beneficial for detecting blood presence with useful resolution also makes it useful for projecting the pattern of blood and vein distribution back on to the skin. The major difference is laser selection for the projection application is to ensure that the wavelength of the light is within the visible spectrum for the human eye. For example, 635 nm light is perceived as bright red light by the human eye, while an IR laser at 740 nm is nearly invisible to the eye but is absorbed more by blood vessels than by surrounding tissues and can be measured using various photo detector technologies. Other colors of light such as green have significant benefits as the projected color since the eye is most sensitive to these wavelengths and it has a high contrast with many skin colors. Furthermore, in certain embodiments a single color laser may be selected that through novel techniques can perform both the projector and scanner functions. In this application, terms visible and infrared light are used to describe approximate wavelengths of light being used in the invention. Furthermore, specific wavelengths have been referenced in certain embodiments. These conventions were used for both clarity of discussion and as specific references to devices and wavelengths that are commercially available today. Referring to FIG. 16, the useful spectrum for each of the critical functions in a detection system is shown. As new devices become commercially available with desirable characteristics they can be used in the invention as long as their wavelengths fall in or near the identified ranges for their particular function. For example, a 785 nm laser might be a preferred embodiment since it would be:

a. Lower cost since it is produced in high volumes for use in DVD players b. Available in higher power versions of 120 milliwatts and above c. Easier to separate from 638 nm since their wavelengths are further from each other d. Less divergent Additionally, the use of laser as opposed to other techniques known in the art such as the Luminetx product allows finer control over the scanning for blood vessels. Since the laser is only striking a single spot on the body, the laser that is used to detect the presence of blood can be modulated on the fly wherein the intensity can be increased or decreased on a spot by spot basis. In a camera based solution, since the infrared light floods the area being scanned, no such control is possible.

Mirrors

Through the use of movable mirrors, the laser spot can be rapidly moved across the target area of the body. As the spot moves across the body there will be a modulation of the amplitude of the reflected light that is proportional to the attributes of that point on the body. For example, red, near IR and IR light will be absorbed and reflected in proportion to the amount of blood at the point at which the laser strikes the body. The invention uses this modulation to determine the location of veins. Other wavelengths of light will be reflected in proportion to the topology of the body at the point at which the laser strikes and can be used for enhancing vein detection.

Scan Mirrors

The invention uses one or more moving mirrors to move the laser light spot across the patient's skin in a variety of different possible patterns. The laser light is projected from a light generator on to the mirror and as the mirror is moved, the projected spot of light moves as a function of the angle of the mirrors at a given moment in time. The light is projected on to one or more mirrors moving in a coordinated way so as to generate a pattern of light on the target surface such as the patient's skin. Many patterns are possible by changing mirror attributes such as mirror size, position in relationship to each other and to the laser or lasers, the degree of the mirror's angle and the speed of mirror movement.

Random vs. Fixed Patterns

A scanning method implemented with the present invention is unique in its approach to scanning the target area. In general, the lower the level of precision required in positioning the laser spot, the easier and less costly it is to produce the pattern.

Coaxial Lasers

In a preferred embodiment, instead of a laser projector there is no need for a reproducible scan pattern so that from frame to frame the laser scan lines do not need to fall reproducibly upon the scan lines of the prior frame, thus, there is no need to know the instantaneous position of the laser. The reason being, the light used for detection and for projection are either from the same light source or from multiple coaxially aligned light sources and the vein detection is performed in near real time. The projected visible light can be modulated in real time so that whatever location is being imaged is instantaneously being projected and only a small offset between detection and projection occurs which will not be noticeable to the user. Therefore, since the image projection happens within the scan, it doesn't matter if the scan pattern on the next traversal of the area proceeds in the same way the previous scan pattern did.

Parallel Lagging Projection Laser

If small additional processing time is required, rather than coaxially arranging the scan and projection lasers, the system can hold them parallel with a small gap in one direction. In this way, the spots follow closely behind each other as the mirrors move, but there is additional time between when the detection spot hits a point on the body and when the closely following projection spot hits the body.

Repeatable Patterns

In other embodiments, there are benefits to knowing the instantaneous position of the laser spot. In such embodiments, the desire would be to delay the projection of the image so that analysis that requires additional time can be performed.

A raster pattern is one type of repeatable pattern. In such a pattern, there are a number of different delay strategies.

1. A short time delay that is a subset of a scan line where the lasers are arranged in parallel rather than coaxially so that the projection spot lags slightly behind the detection spot.
2. Alternating scan lines where as the lasers pass right to left the system performs detection and as it passes from left to right it projects
3. Alternating frames where the lasers complete their full x and y travels while capturing the information into memory and then projecting on the subsequent frame.

These differing approaches each have benefits. The shorter the time delay between capture and projection, the less complicated the system needs to be in terms of processing and memory. As the delay increases, more information needs to be stored and processed, and hand jitter becomes more of an issue. If the frame rate is fast enough, the user would not notice the lag even with the occurrence of hand jitter. Hand jitter is the result of motion of the hand holding the scanner in relationship to the body. In typical systems with frame rates of 30-60 Hz one or two frame delay is practical. If additional frames are needed for processing, than the frame rate can be increased to minimize the delay. Alternatively, the system can use digital or optical image stabilization well known in the art to maintain alignment from frame to frame. One method would be to use accelerometers can be used to determine the amplitude and direction of the movement from frame to frame. Many other techniques are well known in the art.

The positive side of frame-level or multi-frame delay is that more complex algorithms can be used to identify the veins such as edge detection and line detection algorithms that are well know in the art.

Averaging Across Frames

One embodiment of a system that uses repeatable scanning is one in which the image is averaged across two or more frames, thereby increasing the quality of the image captured and therefore increases the ability of the system to accurately detect the position of blood vessels.

Pattern Generation

Many patterns of scanning are possible. For example, the patterns can be based on raster, collapsing ellipse, spirals, lissajous or random. Tradeoffs between pattern and system complexity can be made to create multiple products of differing cost and performance. For example, if the mirrors are run at their natural resonance frequency, the system minimizes the power needed to move the mirrors thereby either extending battery life or reducing the battery size needed and thereby reducing size, weight and cost.

DETAILED DESCRIPTION OF THE INVENTION

Referring to FIG. 1a-1d, preferred embodiments are shown that generate raster, lissajous and collapsing ellipse and spiral patterns. The drawings show the mirror (e.g., 1250) on top of the electrical wave form (e.g., 1258) that is applied to the mirror to control its motion. These sinusoidal wave forms move the mirror in a back and forth pattern with maximum deflection at the peak of the wave, rest at the center of the wave and the opposite maximum deflection at the opposite peak of the wave. Also indicated in the drawing are the most preferred frequencies and the preferred ranges that would be used in an implementation of the invention.

Raster Pattern Generation

In FIG. 1a, a raster pattern 1257 is generated using two mirrors. Mirror 1250 is mounted so that it has a single degree of freedom of motion at fulcrum 1251/1252. A laser light source as described elsewhere strikes the mirror at an appropriate angle so that the angle of reflection is such that the light properly strikes the second mirror 1255. Mirror 1250 oscillates at a high frequency, for example, such as 20 KHz 1258. This generates the horizontal motion in the raster pattern 1257. The now moving beam 1253 is projected on to the second mirror 1255 so that it is parallel to its axis of movement. Mirror 1255 is mounted so that it has a single degree of freedom of motion at fulcrum 1254/1256. Mirror 1255 moves at a slower rate such as, for example, 60 Hz as shown in waveform 1259. The generated pattern is bi-directional, with the beam moving right to left and left to right as the fast mirror 1250 moves and top to bottom and bottom to top as the slow mirror 1255 moves.

A preferred embodiment uses 20 KHz for waveform 1258 and 60 Hz for waveform 1259. Other preferred embodiments can use 7 KHz to 35 KHz for waveform 1258 and 45 Hz to 90 Hz for waveform 1259.

Lissajous Pattern Generation

Referring to FIG. 1*b*, a preferred embodiment for the generation of a lissajous pattern 1265 using a single mirror 1272 that can move on two axes is shown. An alternative embodiment would be to use two mirrors arranged as shown in FIG. 1*a* but modulated as described for the lissajous pattern. The mirror is capable of moving along the axes created by fulcrum pairs 1266/1269 and 1267/1268. The mirrors are moved at different frequencies and in a specific phase relationship to generate this pattern. A lissajous pattern is mathematically described by the equations:

$$X=A \sin(at+\text{phase}), Y=B \sin(bt)$$

The two axes are modulated based on this relationship where various values of A, B and the phase offset control the specifics and density of the projected lissajous pattern. Waveform 1270 shows the X value over time and waveform 1271 shows the Y value over time. In the equation, A is the amplitude of waveform 1270 and B is the amplitude of waveform 1271. at and bt are the angle of the sine waves over time and phase is the phase shift (angle offset) between the two waveforms 1270/1271. Many values of these variables can be used for a scanning application, but a preferred embodiment would select values that move the mirror at its resonant frequencies so as to minimize power consumption.

A preferred embodiment uses 400 Hz for waveform 1270 and 60 Hz for waveform 1271. Other preferred embodiments can use 300 KHz to 35 KHz for waveform 1270 and 45 Hz to 90 Hz for waveform 1271.

Collapsing Ellipse Pattern Generation

Figure 1C:
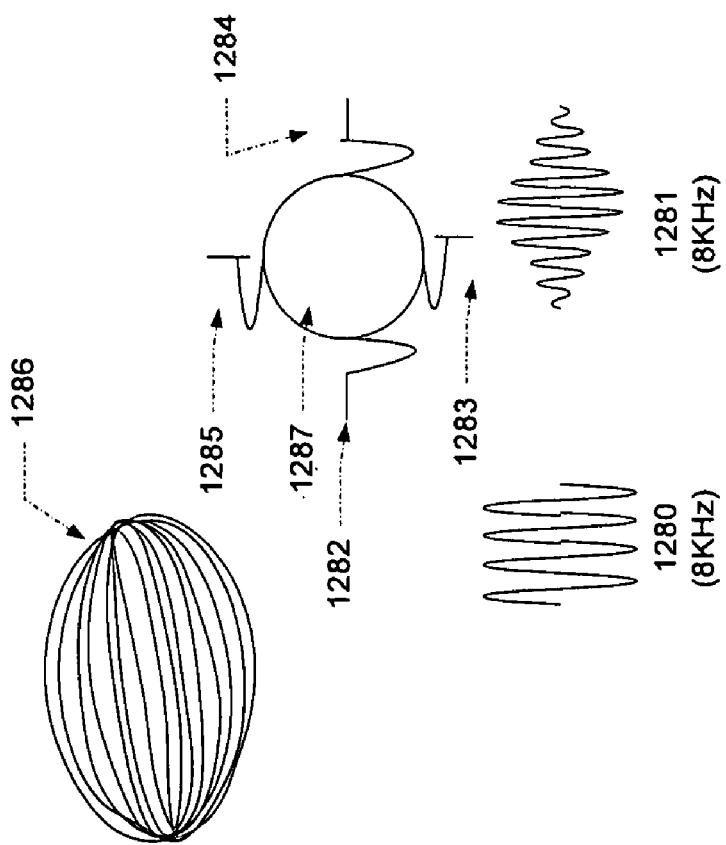
FIG. 1 shows preferred scan patters and the waveforms used to generate them

In FIG. 1*c*, the system is configured for a collapsing ellipse pattern 1286 where a series of loops are drawn across the target area with each circle either slightly smaller or slightly larger than the previously drawn circle. Again, a single mirror 1287 is shown, but the same function can be performed with two moving mirrors. The mirror is capable of moving along the axes created by fulcrum pairs 1282/1284 and 1285/1283. The mirrors are moved at identical frequencies and are 90 degrees out of phase to generate this pattern. The X direction of mirror movement is controlled by the waveform 1280. The Y direction of mirror movement is controlled by the waveform 1281. This waveform 1281 is amplitude modulated so that each subsequent full wave is slightly changed in amplitude so that a different sized circle is drawn.

A preferred embodiment uses 8 KHz for waveform 1280 and 8 KHz for waveform 1281. Other preferred embodiments can use 7 KHz to 35 KHz for waveform 1280 and 7 KHz to 35 KHz for waveform 1281.

Spiral Pattern Generation

Figure 1D:
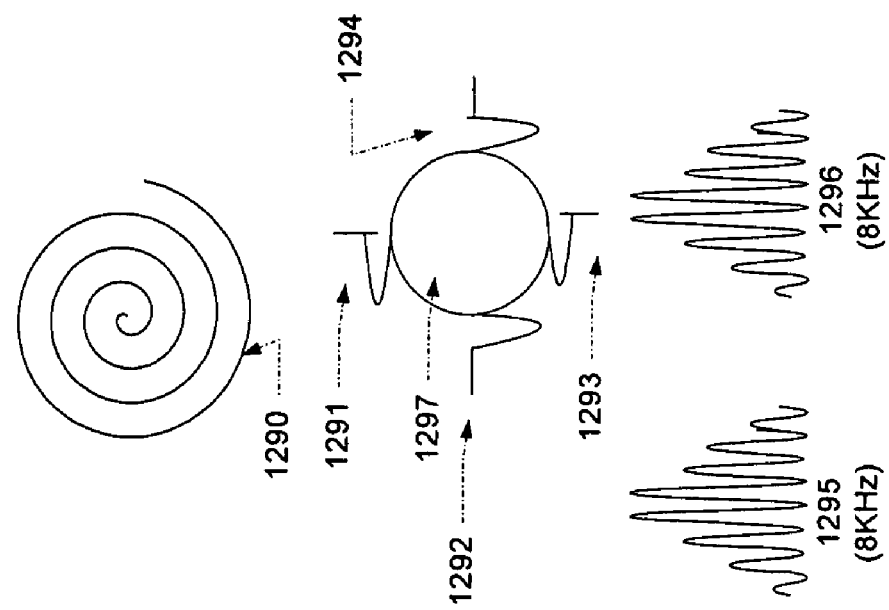

The spiral pattern 1290 in FIG. 1*d* is shown generated by a single mirror 1297 but could be drawn with two mirrors as previously shown. The mirror is capable of moving along the axes created by fulcrum pairs 1291/1293 and 1292/1294. The mirrors, are moved at identical frequencies and are 90 degrees out of phase to generate this pattern. The X direction of mirror movement is controlled by the waveform 1295. The Y direction of mirror movement is controlled by the waveform 1296. Both waveforms 1295/1296 are amplitude modulated in a sawtooth pattern generating a spiral pattern.

A preferred embodiment uses 8 KHz for waveform 1295 and 8 KHz for waveform 1296. Other preferred embodiments can use 7 KHz to 35 KHz for waveform 1295 and 7 KHz to 35 KHz for waveform 1296.

Bounce Mirrors

In addition to moving mirrors, one or more fixed mirrors may be used in the design of the invention. This allows many different arrangements of the light sources to minimize overall size or to otherwise optimize the positioning of the components of the device.

Referring to FIG. 2*a*, the laser source 10 is oriented to emit light 13 in a desired direction. A mirror 11 is placed in the path of the laser light at an angle to the light beam that is calculated to bounce the light beam 14 into the new desired direction. Additional mirrors 12 can be placed in the path of the beam to further redirect the light beam 15 into a desired orientation. Although two mirrors are shown in FIG. 2*a*, as many or as few mirrors as required can be used. Additionally, although FIG. 2*a* is drawn in two dimensions and the angles shown are right angles; these angles can be set so that the beam is reoriented at any angle required in three dimensions.

In FIG. 2*b*, the laser source 20 is oriented so that the beam 21 strikes the mirror 22 at the appropriate angle and position. Mirror 22 is a moving mirror with an axis of motion shown at 24. In FIG. 2*b*, the mirror is presented as moving on a single axis and therefore projects a single line on the target surface. Mirrors with two degrees of freedom are well known in the art and mirror 22 can be replaced by such a mirror so that it projects a two dimensional scan and projection field on the target area. Alternatively, a second moving mirror can be used as will be described in FIG. 2*d*.

Note that the laser beam 21 can be redirected by one or more bounce mirrors as shown in FIG. 2*b* if necessary to the specific embodiment. Such an implementation is shown in FIG. 2*c*. Laser source 30 projects a beam of light 31 so as to strike the mirror at the desired position and angle. Mirror 32 is oriented so that the reflected beam 33 strikes the appropriate position on the moving mirror 34. Again, the for ease of drawing, mirror 34 is shown moving on a single axis 35, but can be replaced by a mirror with two degrees of freedom so as to project and scan a two dimensional area with only a single mirror.

FIG. 2*d* shows a two mirror system that is used to project and image a two dimensional area. The laser source 50 is oriented so that the beam 51 strikes the mirror 52 at the appropriate angle and position. Intermediate bounce mirrors could be placed in the beam path 51 to reorient the beam. Mirror 52 is a moving mirror with an axis of motion shown at 53. The now moving beam of light 54 is directed to moving mirror 55. Mirror 55 has an axis of motion 56 that is oriented at an angle such as 90 degrees from the axis of motion of mirror 52 shown at 53. In this manner, the light reflected off of mirror 56 forms a two dimensionally shaped scanning pattern 59 on the target area 58.

Different embodiments will use one or more laser colors and sources to perform detection and projection. One embodiment of the invention uses two lasers to perform its functions where one laser is selected to have optimum performance at blood detection (e.g., 740 nm) and the second laser has optimum characteristics to project the resulting image to the user (e.g., 638 nm). The major benefits of this embodiment include the ability to modulate the detection and visible lasers simultaneously, and the ability to select lasers that have ideal characteristics for the function to be performed (rather than a trade off between detection and visibility as will be seen in a single laser embodiment). The laser sources (e.g., FIG. 2d, 10), can be an assembly that provides one or more colors of laser light either arranged either coaxially side by side in parallel.

Combining Lasers with Polarization or Dielectric Mirror

A key element of this embodiment is a mirror system that in addition to moving the light spot as previously described provides a mechanism that causes the two laser beams to become coaxial so that both lasers strike the same point on the patients skin. There are many different ways to align coaxially the visible laser and the infrared laser including the use of dielectric mirrors.

Combining Lasers with Dielectric Mirrors

Dielectric mirrors are specially coated mirrors that can reflect selected wavelengths (or wavelength ranges) of light while allowing other wavelengths to pass through the mirror. In this embodiment one or more coated mirrors are used in the optical path to make the separate laser sources coaxial so that when they strike the moving mirror subsystem, they then strike the same spot on the skin.

Furthermore, separate control systems are provided to modulate the intensities of the lasers. The laser intensities can be independently modulated to control the desired characteristics such as depth of detection and the brightness of the projected image providing a great degree of control over these desirable characteristics.

Additional embodiments are possible where additional lasers are added to provide for further refinement of the detection and presentation of the detected blood. For example an additional laser could be used to determine range to the surface of the skin so that finer control over the depth of detection can be performed. Another example is the use of a second color of visible light so that additional information about useful attributes such as depth of the blood vessel can be presented to the user.

Figure 3:
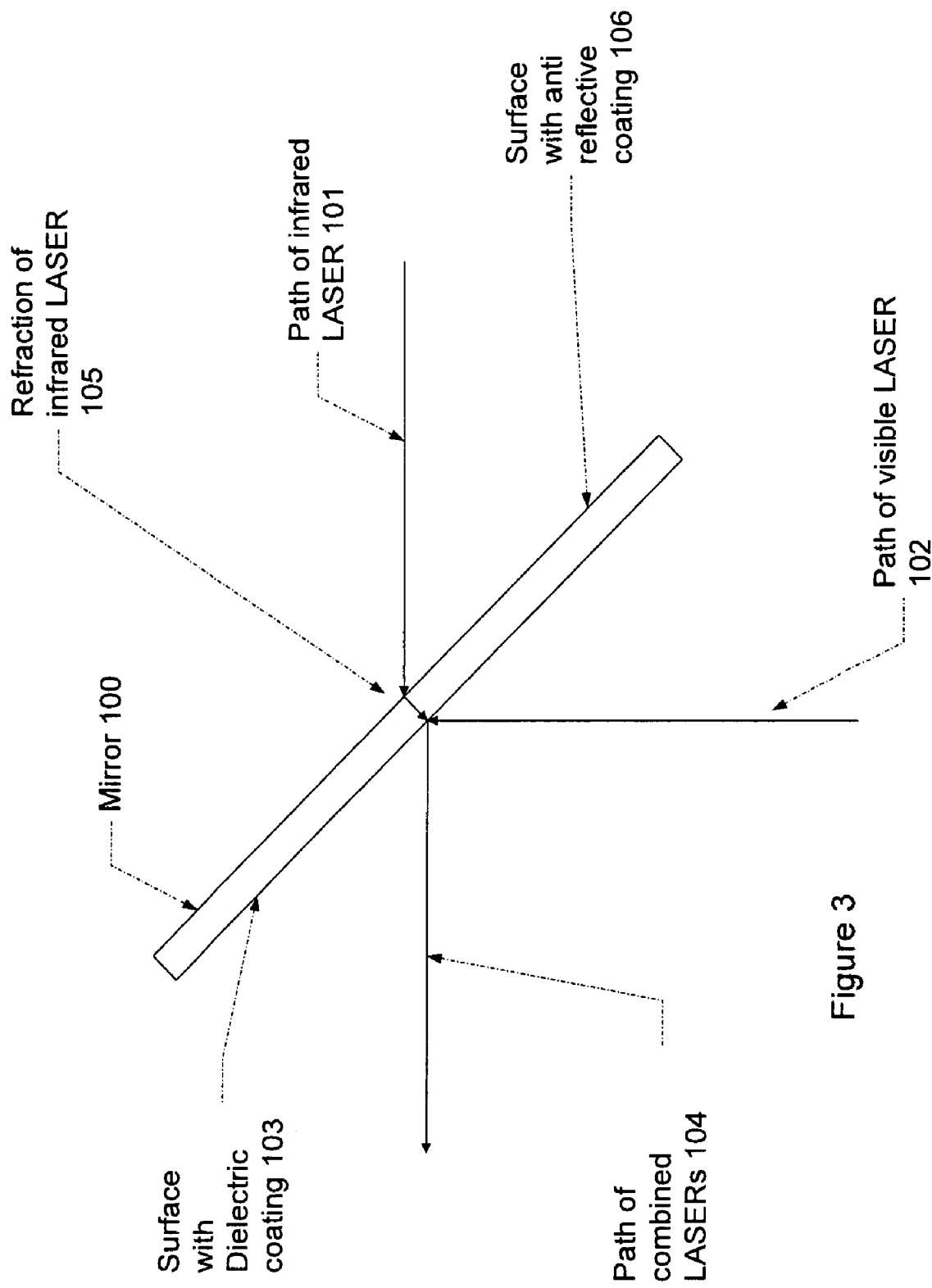
FIG. 3 shows the use of a dielectric mirror to combine multiple lasers into a coaxial output beam

FIG. 3 depicts a dielectric mirror approach. The mirror is shown with the infrared laser placed behind the dielectric mirror. The dielectric mirror is selected so that the infrared laser (e.g., 740 nm) passes through the mirror. The back side of the mirror can be coated with an anti-reflective coating 106 to minimize loss of intensity of the infrared light due to reflection from the back surface of the mirror. It also minimizes the shielding necessary for the back reflection of the infrared light. Note that there is a refraction effect on the infrared laser that is adjusted for by the proper alignment of the lasers. The visible laser (e.g., 638 nm) is directed to the front surface of the mirror which is coated with a material that reflects the light of that laser. The combination of the transmitted laser light and the reflected laser light is now aligned and exits the assembly coaxially. Various implementations can be created that alternate the positions of the visible and infrared lasers.

Similar assemblies can be repeated multiple times for creating coaxial combinations of more than two lasers if needed for the specific marketing or technical requirements of the product.

Combining Lasers with Polarized Elements

A characteristic of laser light is that it is polarized in a known orientation. By carefully controlling the orientation of the laser light, dielectric elements that reflect and pass light polarized in specific orientations can be used to coaxially align the lasers.

Figure 4:
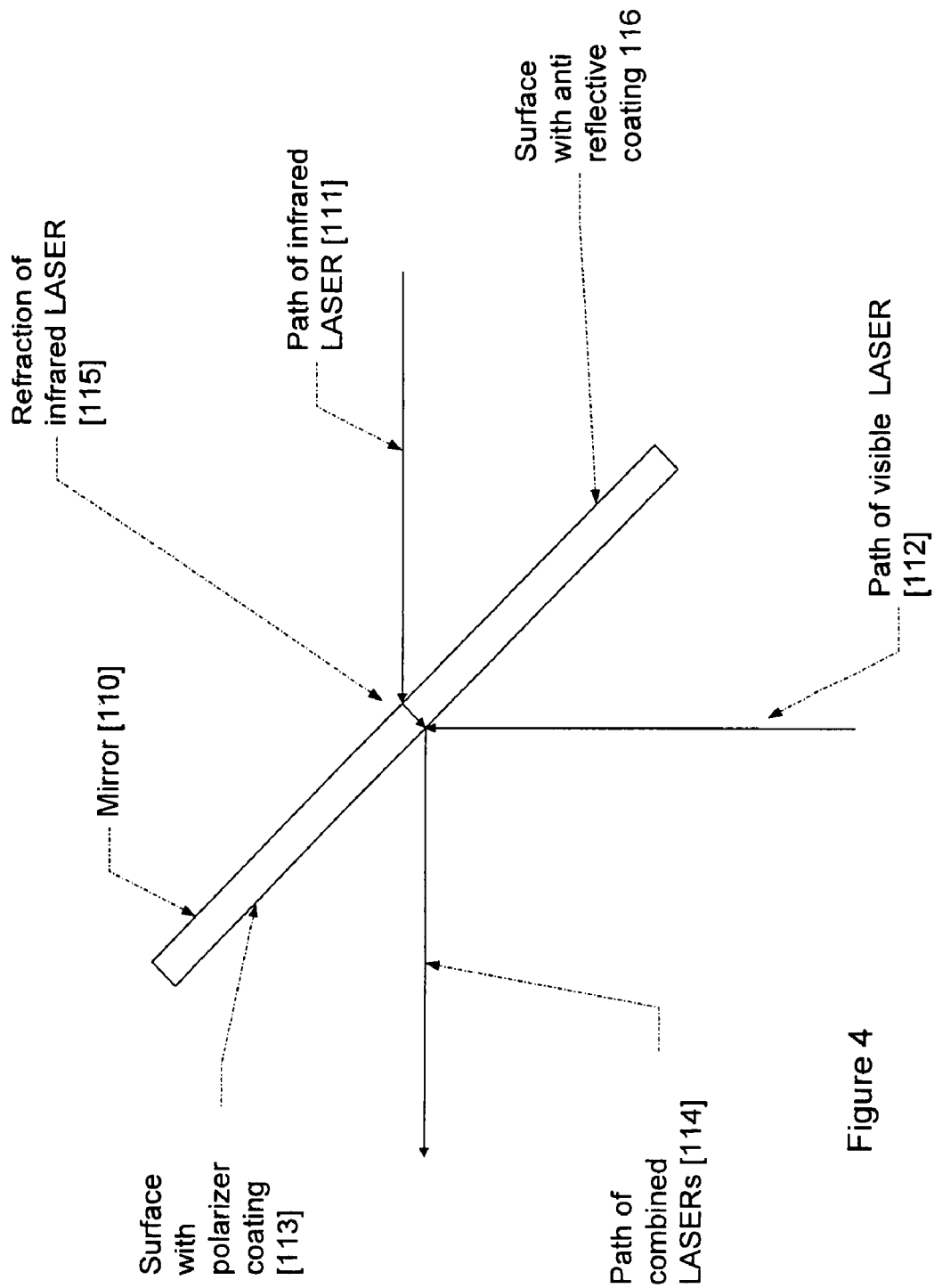
FIG. 4 shows the use of a polarized mirror to combine multiple lasers into a coaxial output beam

With regard to the polarized approach, referring to FIG. 3 and replacing the dielectric coated mirror with a polarized element as shown in FIG. 4. One laser is polarized in a first orientation and is placed behind the polarized element. The polarized element is selected so that the first polarized orientation passes through but the second polarized angle is reflected. The second laser is polarized to the second polarized angle and is aimed at the front of the polarized element and is angled and aimed so that the reflection of the first laser is coaxial with the second laser passing through the polarized element.

In FIG. 4, the element 110 is shown with the infrared laser 111 placed behind the polarizing element. The laser 111 polarization (orientation) and the polarizer 113 orientation is selected so that the infrared laser 111 passes through the element. The back side of the element can be coated with an anti-reflective coating 116 to minimize loss of intensity of the infrared light due to reflection from the back surface of the element. It also minimizes the shielding necessary for the back reflection of the infrared light. Note that there is a refraction effect on the infrared laser 115 that is adjusted for by the proper alignment of the lasers. The visible laser 112 is directed to the front surface of the element 113 polarized so that it is reflected by the element. The combination of the transmitted laser light and the reflected laser light is now aligned and exits the assembly coaxially. While element 110 shows a coating on the front surface, the coating may also be placed on the opposite surface.

Similar assemblies can be repeated multiple times for creating coaxial combinations of more than two lasers if needed for the specific marketing or technical requirements of the product. Additionally, the visible and infrared lasers may be swapped if desired and the parameters of the assembly adjusted appropriately.

Multiple Lasers in a Single Package

Laser diodes that combine more than one laser into a single package can also be used as the laser light source. This eliminates the need for additional beam combining elements in the system. For example, Sanyo DL-1195-251 provides both a red and an infrared laser in a single package.

Multiple Source Array for 1d Scanning

All the embodiments so far have related to a visible laser point source and a IR laser point source bouncing off multiple mirrors, or a single mirror moving in multiple directions, to create a two-dimensional scanning pattern where both the X and Y axis of the two dimensional imaging area is scanned with the single coaxial source of laser light. Rapid scanning causes the eye to integrate this into a single image. In such a system, the beams need to be actively steered in both the x and y directions in the desired pattern. Since there is only reflection from the point at which the laser is currently striking, the photo detector sub system can make inferences about the presence of veins at that particular spot on the target.

An alternative embodiment would be to use a linear array of visible laser sources and a linear array of IR laser sources which then are reflected off a single mirror moving on a single axis. The effect of putting these lasers side by side is to eliminate the need to move the laser point in both the X and Y directions. An appropriate density of laser sources will be required so that the image presented to the user achieves a desirable resolution. These sources could be from individual lasers for each desired line of resolution or from a lower resolution array optically split into a sufficient number of sources to achieve the desired resolution. Many laser arrays known in the art could be used including a VCSEL array.

Using a laser array, you "paint" an entire field of view with the broad brush (the array of laser sources). An advantage of this approach is (i), the mirrors are less complex, and (ii) that the collection of the reflected IR light could also be by means of a retro collective mirror. A retro collective mirror has a field of view corresponding to the array of lasers, and moves in concert with the movement of the array of lasers. A retro collective unit has a significantly improved signal to noise ratio since it is only receiving signal input at any given time directly in a line of sight with the lasers, thereby minimizing the effect of ambient light and other noise sources. A retro collective mirror is inherently larger than a mirror that simply moves the beam. This is to allow for a large light collection area. However due to inertia, as the mirror is made larger, it can no longer be moved as fast as needed for a single laser. This arrangement of multiple lasers allows the system to eliminate the fast moving mirror.

As shown in FIG. 5a, the array of laser light sources 400/408/403, is arranged so that the beams strike the moving mirror 402/406/402 perpendicular to the axis of rotation 402a/407 so that as the mirror swings back and forth on its axis, the laser beams are scanned so that the emitted light forms a rectangle on the target surface 410. FIG. 5b shows a side view of the arrangement, with the array of lasers 403 strike the moving mirror 402 and are reflected in a moving pattern 404.

In addition to the paired visible and IR lasers, the array of lasers could be a single wavelength array of sources that use one wavelength to detect and project as described elsewhere.

In addition to lasers, if the distance to the object being scanned is tightly controlled, then LEDs could be used in place of lasers.

Using Light Valves

A device called a grating light valve, such as those made by Silicon Light Machines (http://www.siliconlight.com), can be used in a similar manner to an array of laser sources. These light valves, typically based on MEMS technology, are basically mirrors that can be set to a reflective or non reflective state. They are typically packaged as an array of light valves 1506 as shown in FIG. 6.

Referring to FIG. 6, a light source 1500 generates a laser beam 1501 which is caused to strike a diffraction grating 1502 which spreads the beam into a line. Since this line of light is divergent 1503, lens 1504 is used to refocus the light 1506 onto the grating light valve 1506. The light 1508, with only a single element reflected from the grating light valve shown for clarity, is reflected off the grating light valve and is directed to a moving mirror 1509, which moves along its axis 1510, and is then modulated in the second axis by that moving mirror and is projected 1511 to the target area. By enabling a single light valve to reflect and all the rest to absorb in synchrony with the movement of mirror 1509, a single scan line can be painted on the target area. Two or more of the assemblies in FIG. 6 can be bundled together so that one or more assemblies are used for visible light and one for infrared light, or a single assembly can be used for both projection and detection as will be described below.

This embodiment can also be combined with a retro collective mirror system to enhance the collection of the reflected light.

Single Laser

In another embodiment, the invention uses a single laser that emits light at a wavelength that is long enough that it is still differentially absorbed by blood but still visible to the human eye. This embodiment is very important in that it enables building a system with only a single laser. All the complexity associated with aligning multiple lasers is eliminated thereby greatly reducing cost, engine size, unit size and power consumption.

Light emitted at 635 nm is one possible choice. In this embodiment, the laser spot performs the dual function of detecting the presence of blood and displaying that presence of blood to the user. It has been determined that a portion of a 635 nm laser penetrates into the tissue and is absorbed by the veins. Accordingly the 635 nm laser can functions as did the infrared lasers for the purpose of imaging the veins. A portion of the 635 nm light does not penetrate the skin and is reflected off of the skin so that it is visible to the user. This portion of the light functions as did the visible laser in the dual laser system.

Single Laser Always on

A novel mechanism is used to allow the single laser to be used for both functions. In this embodiment the laser is never completely turned off. Accordingly, even when the image to be displayed is black, the laser is still powered on at a very low level. The low level is strong enough that it can still be detected by the photo detectors so that the device can still image the veins, but not strong enough to create a distracting visible image (so blacks may appear as a faint red color). When the intensity of the 635 nm laser is subsequently increased to project a bright portion of the visible image, the gain of the analog circuitry associated with the received signal (from the photo detectors) is reduced in proportion. Conversely, when the intensity of the 635 nm laser is subsequently decreased to project a darker portion of the visible image, the gain of the analog circuitry associated with the received signal is increased accordingly. In this manner, the received signal (as measured after the analog circuitry) remains relatively constant regardless of the intensity of the projected image.

Referring to FIG. 7a, a single laser source 70 is oriented so that its beam 71 is aimed into a steering assembly 72. This assembly is constructed as described elsewhere in this patent out of a series of fixed and moving mirrors as appropriate to the specific embodiment. A moving light beam 73 is emitted from the device which then scans the targeted area of the body 74 in a pattern that is appropriate to the specific embodiment.

Typically in this configuration, neither repeatability nor knowledge of the specific beam position at a given time is required since the processing is done in real time as the light beam reads and paints the skin. However, the delay techniques that were discussed previously can be applied to a single laser configuration.

The photo detector 76 is positioned to measure the light 75 reflected from the skin. Since this is a scanning point source, the reflected light is an instantaneous representation of the reflection from a single point 82 on the body. Note that the beam penetrates some distance into the body so the reflected signal is a composite of both surface and subsurface features. The output of the photo detector 77 is fed into a detection circuit 78 [that uses techniques that are well known in the art] to determine a change in the amplitude of reflected light and therefore detecting the relative amount of blood at the point 82 at which the laser is currently scanning.

The detection circuit 78 provides an output 79 to the power supply 80 to the laser source 70. As soon as a vein is detected at the point 82, the power is increased to the laser source 70 which increases the output of the laser so that it is visible to the operator. As soon as the detection circuit 78 detects that the point 82 is no longer over a vein, then the control output 79 is changed so that the laser 70 outputs a light level that is sufficient for detection, but is no longer visible, or is dimly visible, to the operator. The detection circuitry includes the functionality to cancel out the increased reflection when the laser is brightened and the decreased reflection when the laser is dimmed so that the action of projecting the image does not interfere with the ability to detect the veins.

If desired, the sense of on and off can be inverted, whereby the laser is brightly lit when no vein is detected and dim when a vein is detected.

Figure 7B:
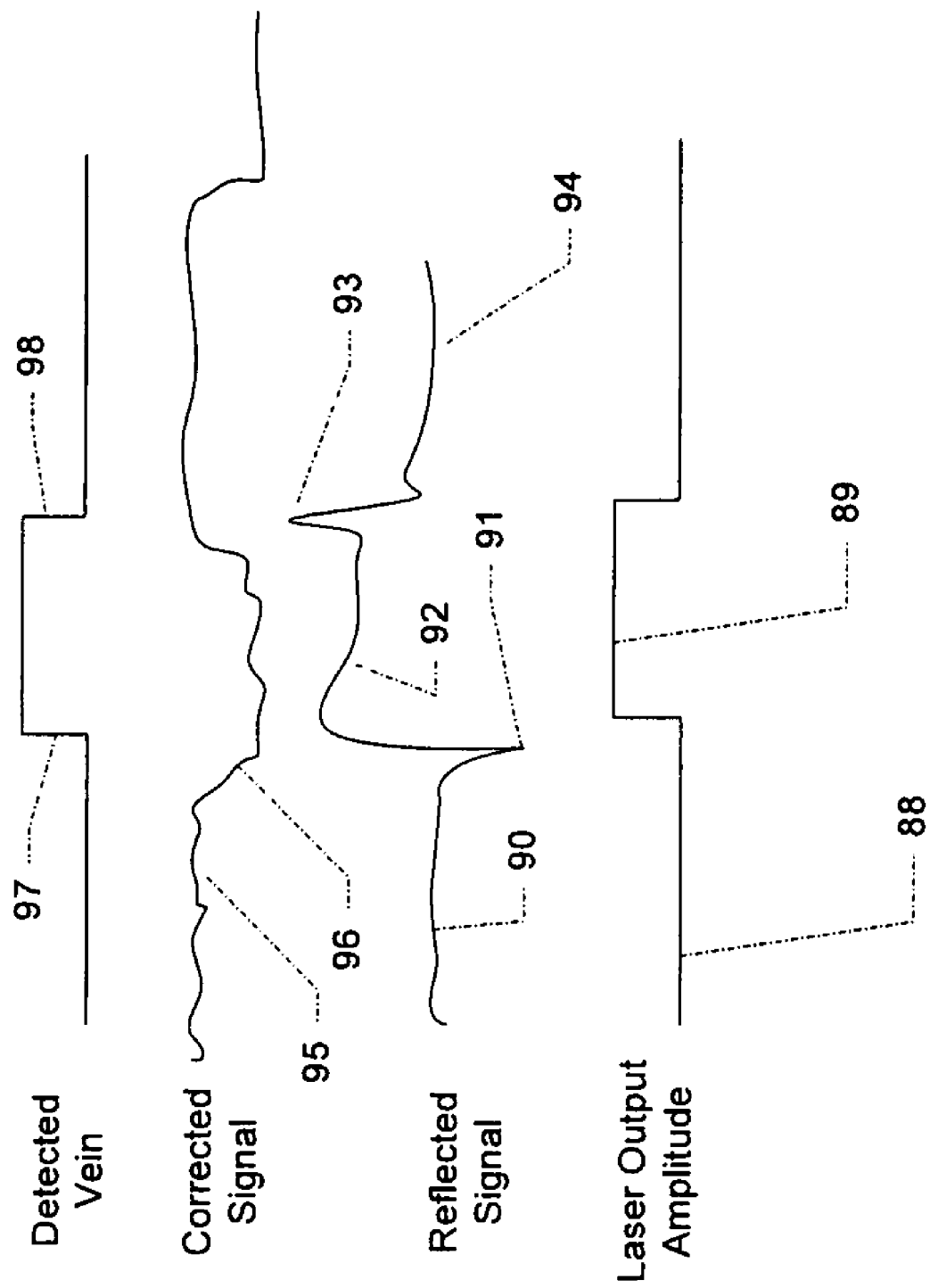
FIG. 7 shows the system and waveforms for detecting a vein and re-projecting an image along the same path.

FIG. 7b provides a representation of the signals being used by the system. The reflected signal 90-94 is representative of what is seen at the inputs 75 and outputs 77 of the photo detector as well as the initial stages of the detection circuitry 78. The corrected signal 95, 96 represents what would be seen in later stages of the detection circuitry 78 once the variations in the laser amplitude 88, 89 are canceled out. The detected vein 97, 98 are representative of the logic in later stages of the detection circuitry 78 as well as the output signal 79 from the detection circuitry 78 to the input of the laser power supply 80. The laser output amplitude 88, 89 represent the output of the laser source 70, 71 as it is increased and decreased to project the acquired image.

Following the reflected signal, at 90 the system is seeing a varying analog signal that is representative of a reflection pattern indicative of a beam that is not crossing a vein. Since different individuals based on skin color, skin condition and place on the body will reflect different amounts of light as this baseline 90, the detection circuitry is designed so that it can determine this baseline in real time. At 91, there is an amplitude drop off as the beam crosses a part of the body where blood is absorbing sufficient light that the detection circuit 78 determines that the beam is over a vein. An internal representation or flag 97 that the beam is over a vein is set and the output to the laser power supply 79 is changed so that the laser amplitude is increased 89 to the bright condition thereby projecting the vein position. Once the beam is brightened, there is a corresponding rise in the amplitude of the reflected light 92. Internally, the detection circuit 78 corrects for that amplitude 96 to eliminate false readings and to prevent saturation of the detection chain 76, 77, 79.

As the beam 73 continues to move, as long as the reflected level continues within the range for vein presence 92, the laser will stay in its high state 89. The beam will eventually move off of the vein and the reflection will increase once again 93 indicating that the beam has moved off of the vein. The detection circuitry 78 will then cause the laser power supply 80 to return to the dim state 88. The reflected signal will now be reduced 94, the detected vein flag will be turned off 98. This process will continue to repeat for the duration of scanning.

Single Laser PWM

It is desirable in some embodiments to have greater control over the intensity of the beam when it is being used for detection. In a single laser system, it is required that the beam intensity be low enough in the dark areas of the image so that they appear clearly different from the lit areas. It would be desirable in certain circumstances such as different skin coloration or the desire to scan more deeply below the skin to bring the intensity of the light up for scanning. In this embodiment, the modulation of the laser between detection and projection can be in real time where the invention time slices the laser between detection and projection so that both functions are performed on the same pass of the laser over the skin.

Figure 8A:
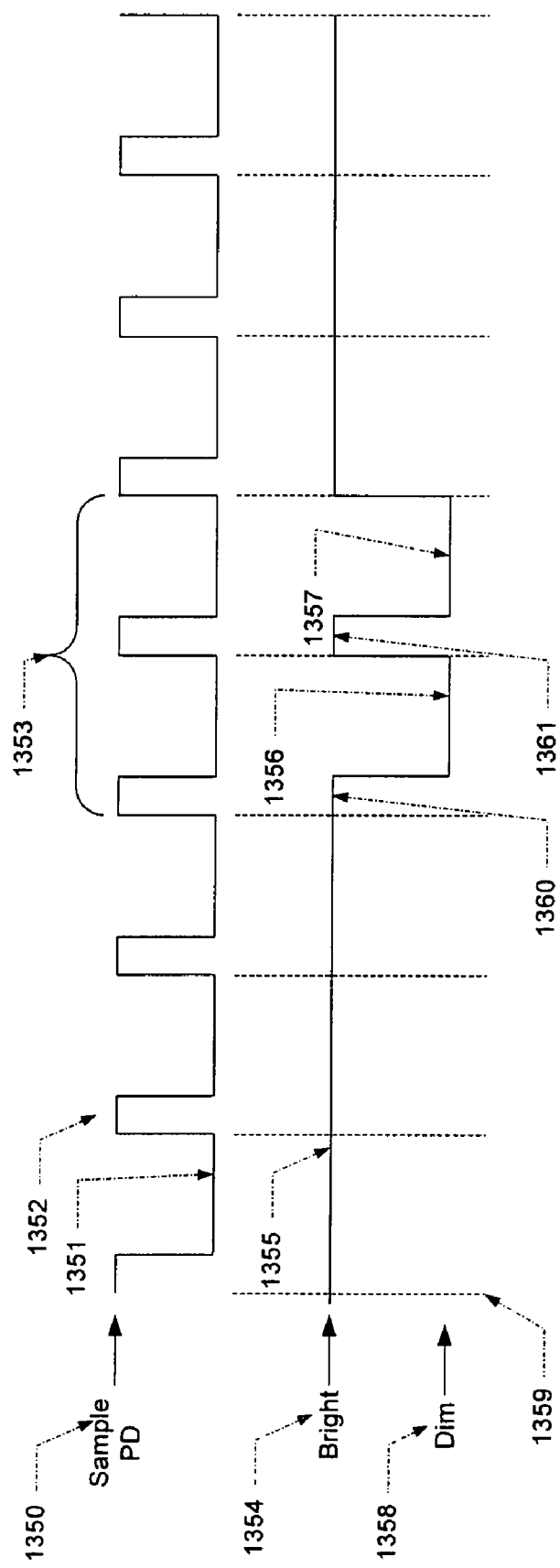
FIG. 8 shows various methods for separating visible and infra red lasers from the reflected signal

In FIG. 8a such a modulation scheme is shown. The signal 1350 shows the sample period for the photo detector. When the clock is high 1352, the signal is sampled. When the clock is low 1351, the signal from the photo detector is ignored. The laser output is switched between bright 1354 and dim 1359. Dim can also be off in some embodiments. As the beam passes over the body, the beam is kept at a bright intensity 1355 until a vein is detected during the period at 1360. In this example, the vein is seen across two periods 1353. In these periods, the output beam is dimmed 1356/1357 for the portion of the time period that is not used for sampling at the photo detector. It is brought back to its bright level 1361 during the sample period of the photo detector. Many variations of this scheme are possible including working with multiple lasers of different colors, and changing the timing of the detection 1352 and projection 1351 intervals and allowing for multiple levels of bright 1354 and dim 1356.

In addition to modulation between detection and presentation modes as described, the laser can also be modulated within each of these domains to provide for variable detection characteristics such as changing the depth of penetration and detection through the skin and changing the intensity of the projection intensity to allow for variations in user preference, ambient lighting conditions and skin color.

Another embodiment of the single laser approach is to time slice the laser output so that very short pulses of high intensity are emitted followed by longer periods of projection intensity. Projection intensity is the light output level that the system wishes the user to see. Vein detection occurs at the bright pulses, but since they are very short, and the eye has a slow response time, they will not perceptibly interfere with the desired projection image. The advantage of this embodiment is that it allows higher intensity for the detection phase allowing for deeper structures to be imaged and allows the system to adjust for skin characteristics.

Alternating Line & Alternating Frame

The techniques discussed previously for alternating lines and frames between detection and presentation in a multiple laser system can also be applied in a single laser system.

The use of these delay techniques allows all of the advanced vein detection techniques to be applied by allowing extra time between detection and projection as previously discussed as well as the improvements yielded by the additional control of laser intensity provided.

Using LEDs Instead of Lasers

As previously discussed a major benefit of lasers was that the beam remains a constant size over a very wide range of distances between the light source and the surface of the patient's body. An alternative embodiment can be created that is of lower cost which uses tightly focused light emitting diodes (LEDs).

Figure 9:
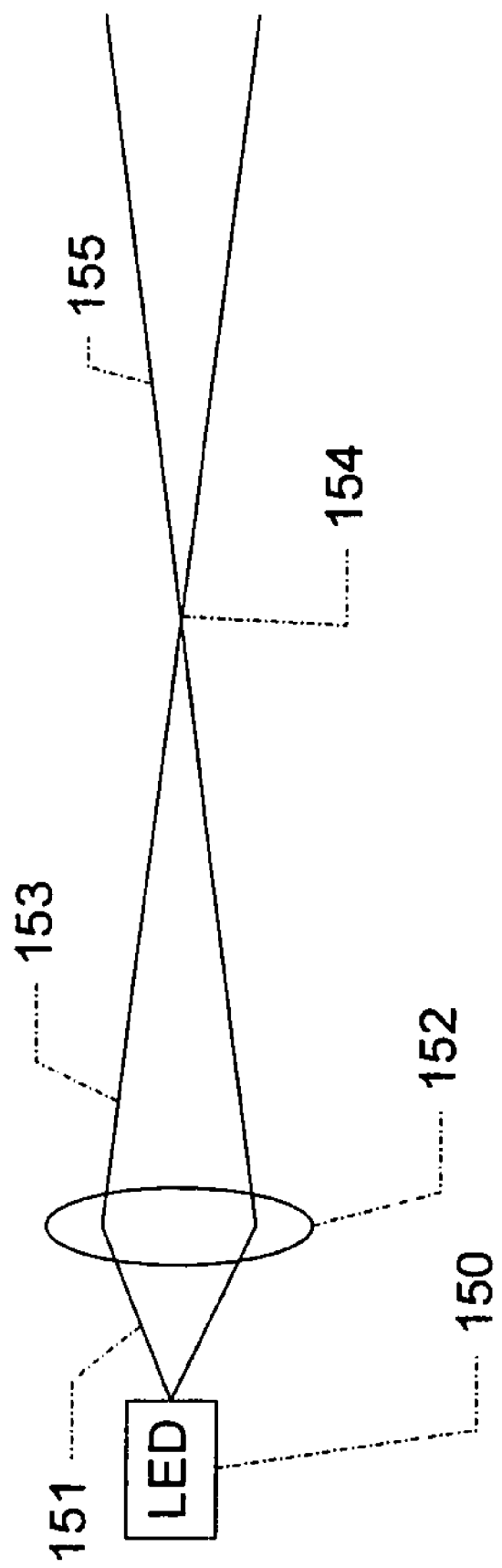
FIG. 9 shows a focusing system for an LED

In FIG. 9, a focusing scheme is shown for an LED light source. The LED 150 projects an unfocused beam of light 151 on a lens or assembly of lenses 152 which are designed to have a specific focal length so that the converging light 153 comes to a point 154 at a useful working distance. Beyond the working distance the light begins to diverge 155.

The disadvantage is that the distance between the scanner and the body surface will need to be much more tightly controlled than in a laser embodiment. Several controlling mechanisms are possible such as a physical device that is placed against the skin. One possible mechanism is shown in FIG. 10a. This approach uses a mechanical device that includes an open base 424 that is placed against the skin while allowing the image to be captured and projected through the opening 425. The opening can be either closed as shown or open based on the design requirements of the specific embodiment. The base 424 is connected to the scan head 422 through one or more separation members 423/424 that are sized to ensure the proper distance is maintained between the scan head and the skin. The scan head 422 can be fixed to the positioning device or it can be a separate piece that is attached when needed and then removed.

In an alternate construction, as shown in FIG. 10b, the mechanism can simply be a rod 430 of the appropriate length that projects from the scan head so that the distance is maintained when the end of the bar touches the skin 420.

Additional features include:
1. A lighted crosshair or other pattern projected towards the skin that becomes crisply focused when the device is being held at the proper range
2. An electronic ranging mechanism such as infrared or ultrasonic that measures the distance and then emits a set of tones that indicates that the device is at the appropriate distance. The tone feedback can be positive—only on when at the proper distance, negative—only on when outside of the proper distance or both with separate tones to indicate the two states.

IR Camera, LED Projector

Another useful embodiment of the invention is based on the use of LED projection with alternative types of detection. Given the need for tight control to be maintained of working distance, or to provide an auto focus mechanism in an LED embodiment, the detection subsystem can be replaced with a camera element that is sensitive to IR light and an IR light source to illuminate the target area. In this embodiment, the image would be captured using the camera, processed to detect vein positions within the field of view and an LED implementation as described earlier would be used to project the image back on the patient's body.

Auto-Focusing in Non-Laser Embodiments

Figure 11:
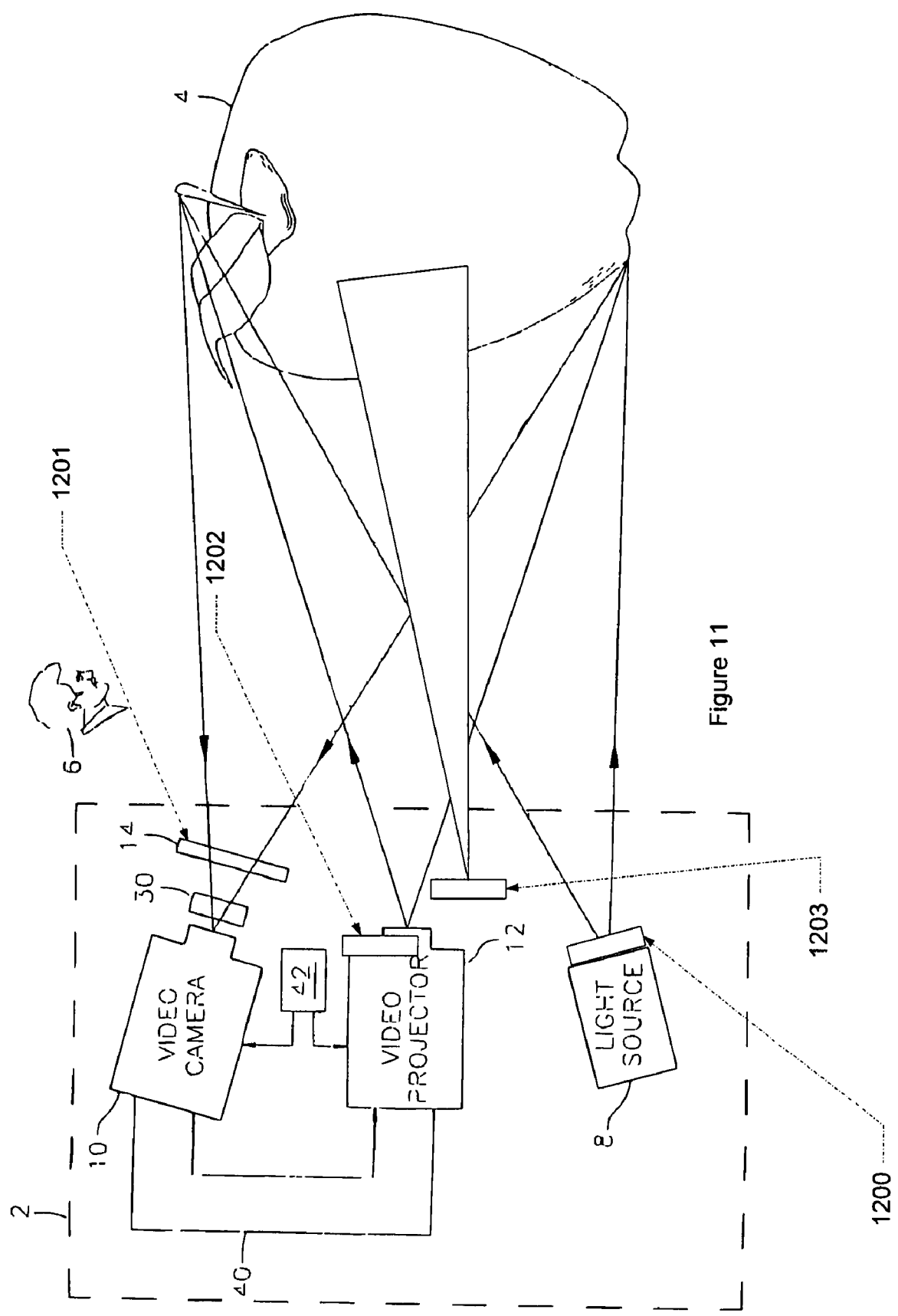
FIG. 11 shows an auto-focus system for a camera/projector based embodiment of the invention

As discussed, a key benefit of using lasers is that they are inherently focused over a wide working range. As discussed above, since LED's do not remain focused over a long working range, the use of LEDs requires tight control of distance to the body area to be imaged. Auto-focus lenses, such as those seen on cameras, could be integrated into the design so that a broader working range can be provided. Typically however an LED implementation is used to minimize cost so that normally the expense of auto-focusing would have limited application. However, other embodiments of vein enhancement systems such as that described in U.S. Pat. Nos. 5,969,754 and 6,556,858 would benefit from the use of auto-focus technology and have a cost basis that support such an implementation. FIG. 11 shows an improvement to the device shown in FIG. 1 from U.S. Pat. No. 5,969,754. In this figure, an auto-focusing feature has been added. Computer controllable focusing lenses 1200, 1201, 1202 are placed in front of the key optical systems, typically replacing the existing lenses (e.g. 14). These controllable auto-focus lens systems are controlled by either the main computing element of the system or a separate microprocessor dedicated to control functions such as and including auto focus. Distance to the body is determined by a range detection system 1203, many different types which are well known in the art.

Photo Detector

In addition to the subsystems that project the laser or laser spots on to the patient's skin, a further subsystem provides the detection of the light that is reflected from both the skin and the subsurface features of the patient's body. As previously mentioned, blood rich areas of the body such as veins absorb light in the infrared spectrum to a greater degree than surrounding tissues. The invention uses one or more photo detectors to measure the varying amount of reflection from the target. Light sensitive devices including photo diodes, CCD camera elements and CMOS camera elements and LEDs can be used as the photo detector to perform these measurements. The present invention can implement multiple photo detectors spatially separated so as to increase sensitivity, and reduce the interference associated with speckle, and specular reflection. However, as mentioned previously, one can achieve a reasonable result by using a single photo diode; this will depend on the desired output and/or operating needs.

The characteristics of the photo detector(s) will vary between embodiments. Photo detectors can be selected with narrow band characteristics so that only the detection laser is received by the detector. This would also have the advantage of making the system less sensitive to ambient light. Detector characteristics can be determined through selection of the photo detector itself or through the use of filter materials placed in front of the detector. Another alternative approach would be to use a photo detector that is sensitive to a broad range of wavelengths and then by modulating the transmitted laser light, the system would be able to determine which laser, and therefore light wavelength, was being detected at a given moment in time.

Variations on the Number of Photo Detectors Used

Different embodiments may use different numbers of photo detectors based on the technical and business needs of the specific implementation. For example, a single photo detector might be used to minimize size or cost. Multiple photo detectors may be implemented so that they are spatially separated so that the system is less sensitive to specular reflection. Skin is somewhat shiny and causes unwanted specular reflection. In an embodiment where the photo detectors are separated, they each see the returned signal from a slightly different angle so that the effect of specular reflection is minimized.

The larger the area of a photo diode (one type of photo detector) the lower the speckle noise seen by the system since the random pattern of speckles are integrated as a single reflection since they all strike the photo detector simultaneously. The larger area means that the small speckles are a smaller percentage of the total area and therefore have less of an impact on the signal. However, larger photo diodes have more capacitance and are therefore slower, which is undesirable in many embodiments of the invention. By using multiple photo diodes, the detector area is increased, providing the reduction in speckle noise, without the negative impact on the speed of the detector. This is due to the smaller capacitance of the smaller photo diode and the fact that each photo diode being able to have its own pre-amplifier circuit.

A further benefit of having multiple photo diodes is that the received signal is increased without the need for additional amplifier gain and the associated noise that it would introduce into the system.

A further benefit of having multiple photo diodes is that as the laser point moves across the human limb, the curvature of the limb causes an increasing amount of the light to be reflected away from the scanner as the beam moves to the sides of the limb. The addition of spatially separated photo detectors adds additional collection area nearer to the spot being scanned and allows more of the reflected light to be captured. In addition, having two separately placed photo detectors reduces the impact of specular reflection.

As an alternative to the addition of a photo detector, collection mirrors can be used in the collection path so that light is collected from spatially separate points and are then reflected on to a single photo detector shared by two or more collection mirrors.

Figure 12:
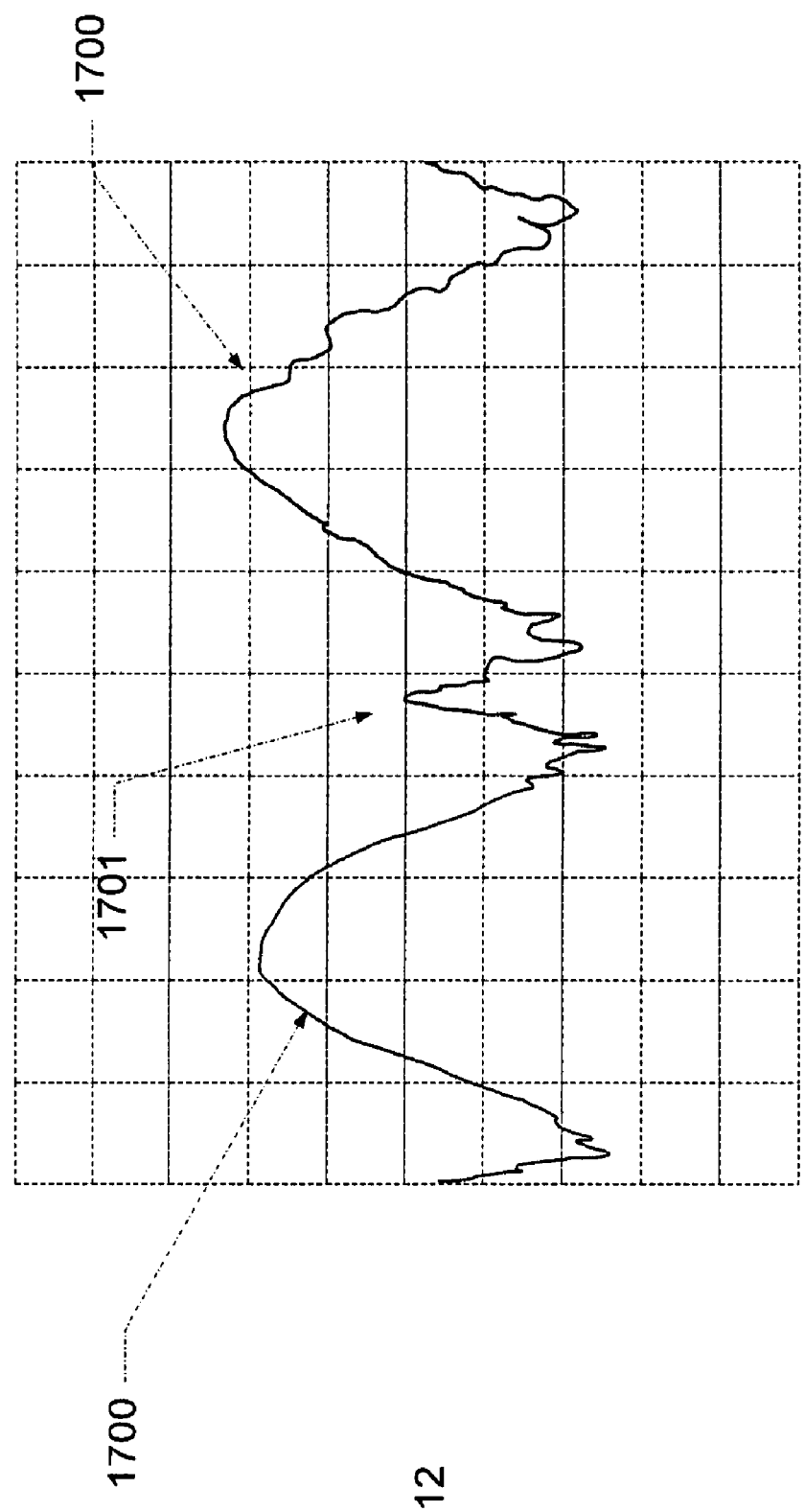
FIG. 12 shows the waveform of the reflected signal

FIG. 12 shows an oscilloscope image of the signal received from the photo detectors. The large 'humps' 1700 are caused primarily by the change in angle as the laser scans across the arm. The amplitude of these humps will be affected by the angle at which the beam strikes the arm. A vein signal is also shown 1701.

Array of Photo Diodes

Figure 13:
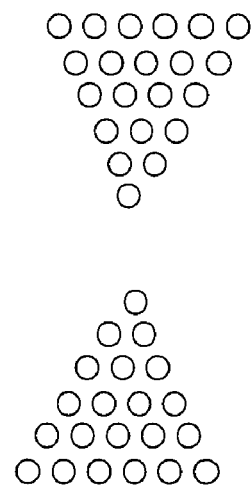
FIG. 13 shows an array of photo detectors arrange to increase the detection area in proportion to the angle from center

In one embodiment, there is an array of smaller photo detectors arranged so that there is more collection area towards the outside of the detection area (where the roll off of signal due to the curved body and the angle of the laser occurs) and less towards the center where the reflection is more direct and intense. An example pattern is shown in FIG. 13. This could be implemented as a discrete photo detectors arranged in the appropriate pattern or as a monolithic semiconductor component.

Fresnel Lenses—Tailored Response Over the Field of View

Another technique to control the variation of reflection due to the change in laser angle across a scan line is to use specially configured lenses over the photo diodes. In this example a lens is cut from a standard fresnel lens in a pattern that increases the amount of collected light as the angle from the center of the photo diode increases thereby flattening the received signal.

Figure 30:
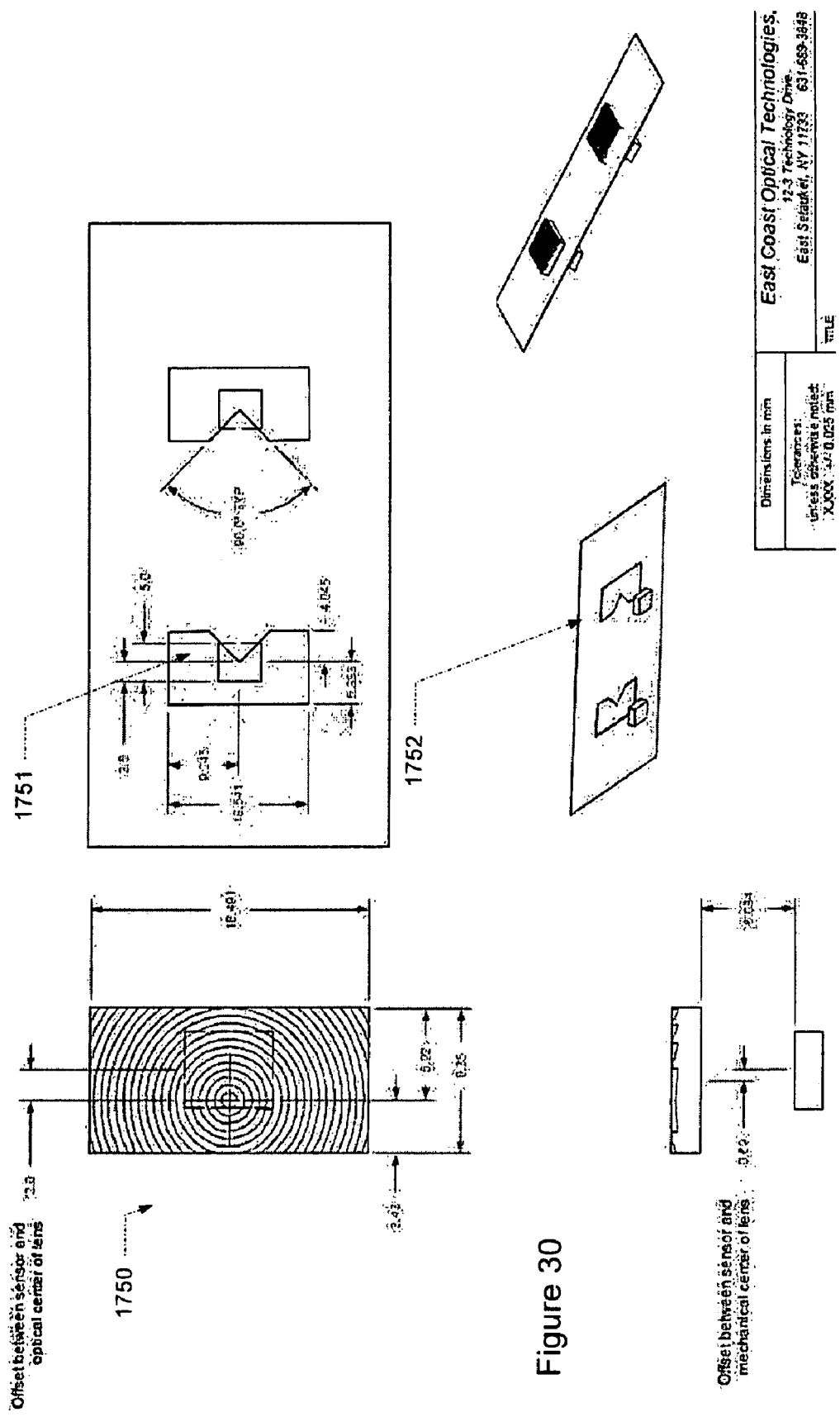
FIG. 30a shows a perspective view of the sensor and mechanical center of the Fresnol lens assembly that can be used to enhance the return signal from the edges of the scan area.
FIG. 30b shows a perspective view of the sensor and the optical center of the fresnol lens assembly that can be used to enhance the return signal from the edges of the scan area.
Figure 30A:
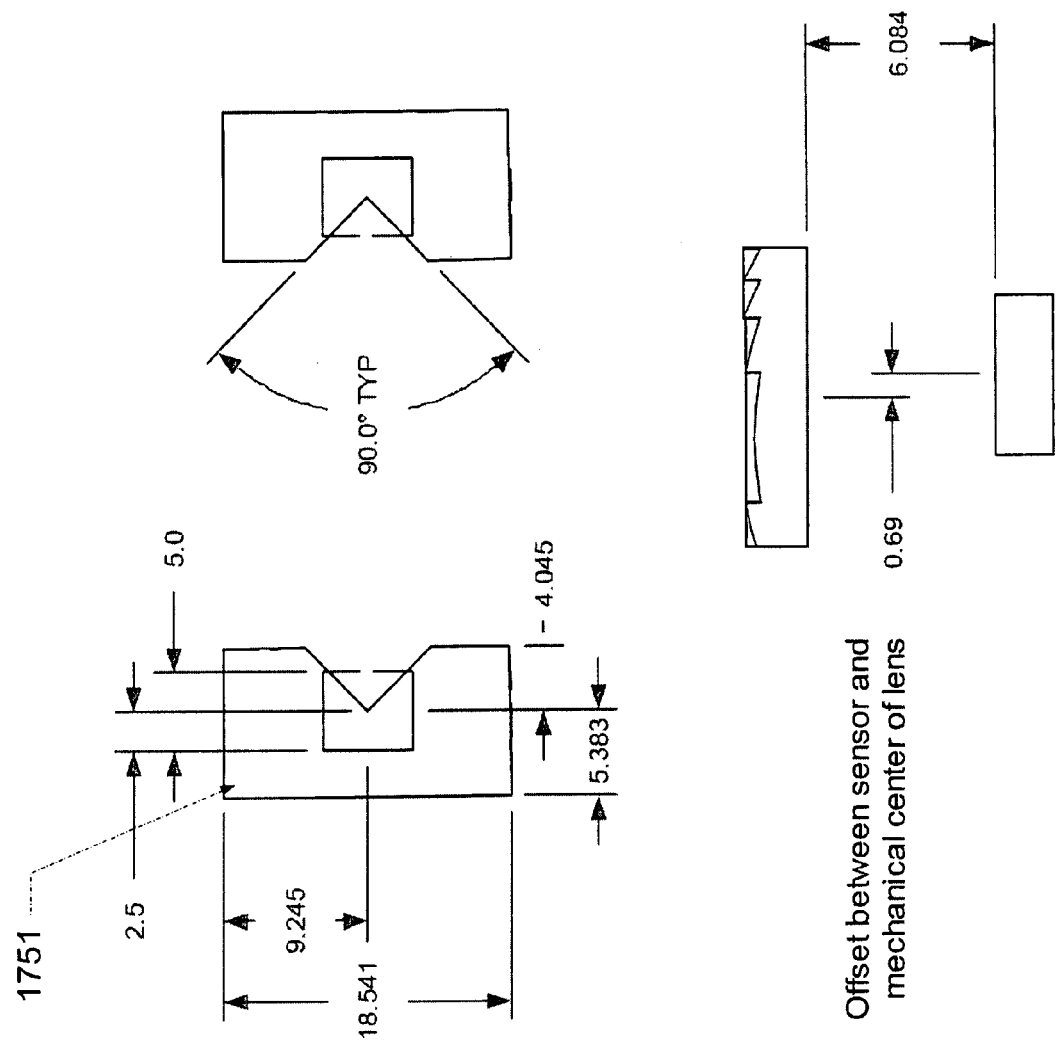
Figure 30B:
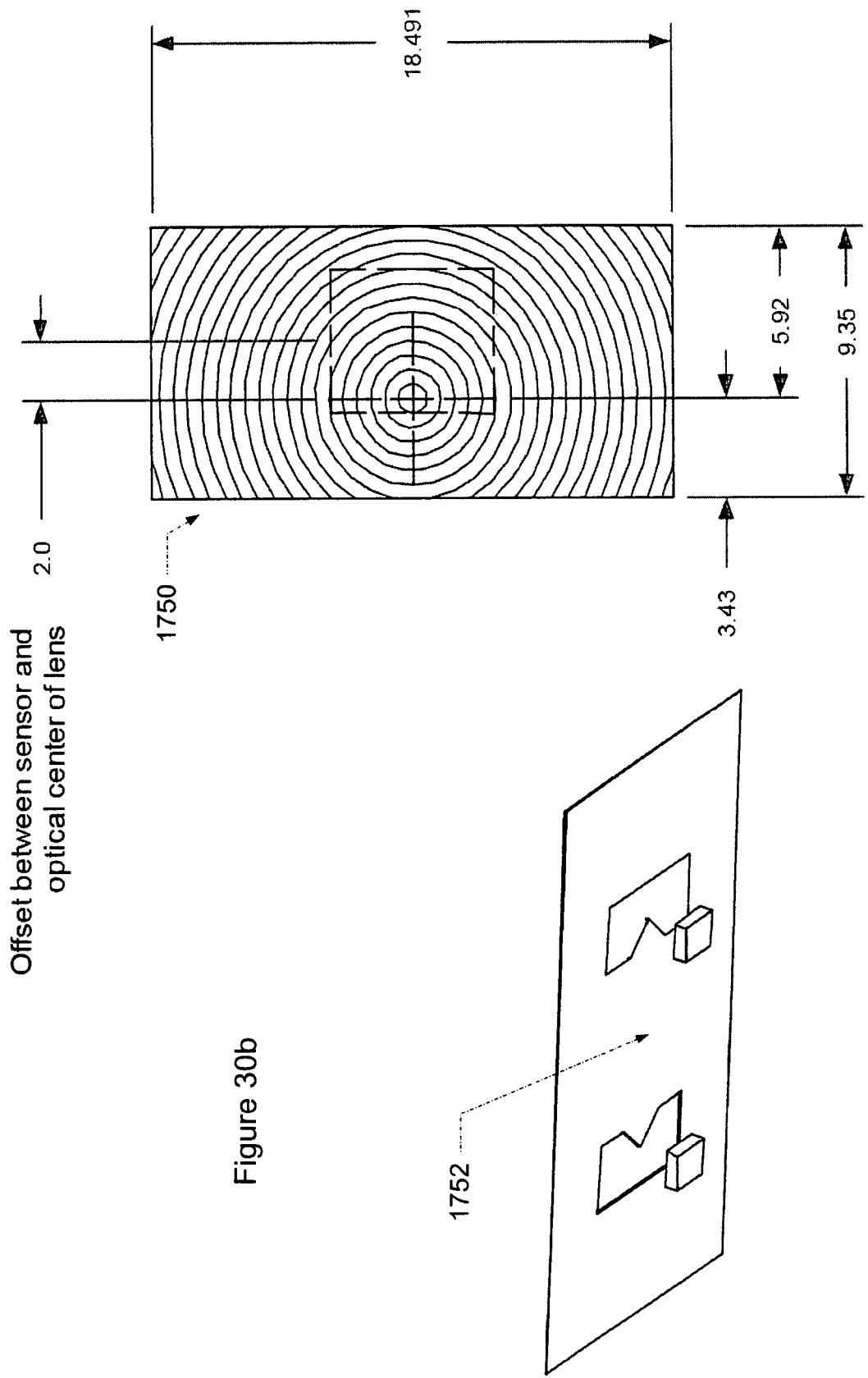

As shown in FIG. 30, a standard fresnel lens 1750 is cut in a pattern 1751 that when placed over the photo detector provides additional collection of light reflected from the edges of the scan line and then refracts that light into the photo detector.

Electronic Filter

The frequency domain of the signal caused by the angle change as the laser sweeps is slightly different than the signal caused by the presence of a vein. Through the use of electronic filters, well known in the art, such as switched cap filters, the impact of this signal can be reduced early in the signal processing chain, importantly prior to the vein detection circuitry.

Measuring Topology with an Additional Laser

In the prior descriptions, a simplified model of the reflection of the laser light was presented. In fact, there are varying degrees of absorption of light from all of the structures illuminated including the skin, the blood vessels and other surface and subsurface structures of the body. Additionally, since the body is a three dimensional structure, the range to the point on the surface being scanned varies in real time as the imaging point is scanned. For example, the curved shape of the arm would result in less returned reflection towards the edge of the arm as that surface curves away from the scanning device. The result is that these variable reflections off of these body structures add signals that must be filtered out to accurately detect the vein structure. Furthermore, as the beam sweeps across the body, when the beam is at the center point of its sweep, the reflected light received at the photo detector is greater than when the angle of the beam is at its maximum deflection and therefore more light is reflected away from the photo detector.

There many techniques that can be used to eliminate or cancel out these undesirable signals.

The reflected signal received by the infrared photo detector is representative of both the veins and the surface topology of the patient's body. Put another way, the surface of the patient affects the reflected infrared signal. This is not desirable in that in most applications the user is only interested in the veins of the patient and not the surface topology. It has been observed that the short wavelength light such as blue and ultraviolet are reflected by the skin and is mainly representative of the surface topology of the patient and has no vein information contained therein. By utilizing a second coaxial laser light source at a short but visible wavelength and a second photo detector subsystem for receiving the short wavelength light reflected signal, the short wavelength light signal (which contains information about the topology of the skin) can be subtracted from the infrared signal (topology+veins) yielding a signal that is solely the veins (topology+veins−topology=veins). This works in that since the beams are coaxial, they will be affected by the topology of the target area symmetrically.

This approach is particularly useful in a system that does not have a microcomputer for storing a complete image and for performing image processing on that image to enhance the veins (and reject all other types of signals) but also has benefit to a stored image system.

Figure 14:
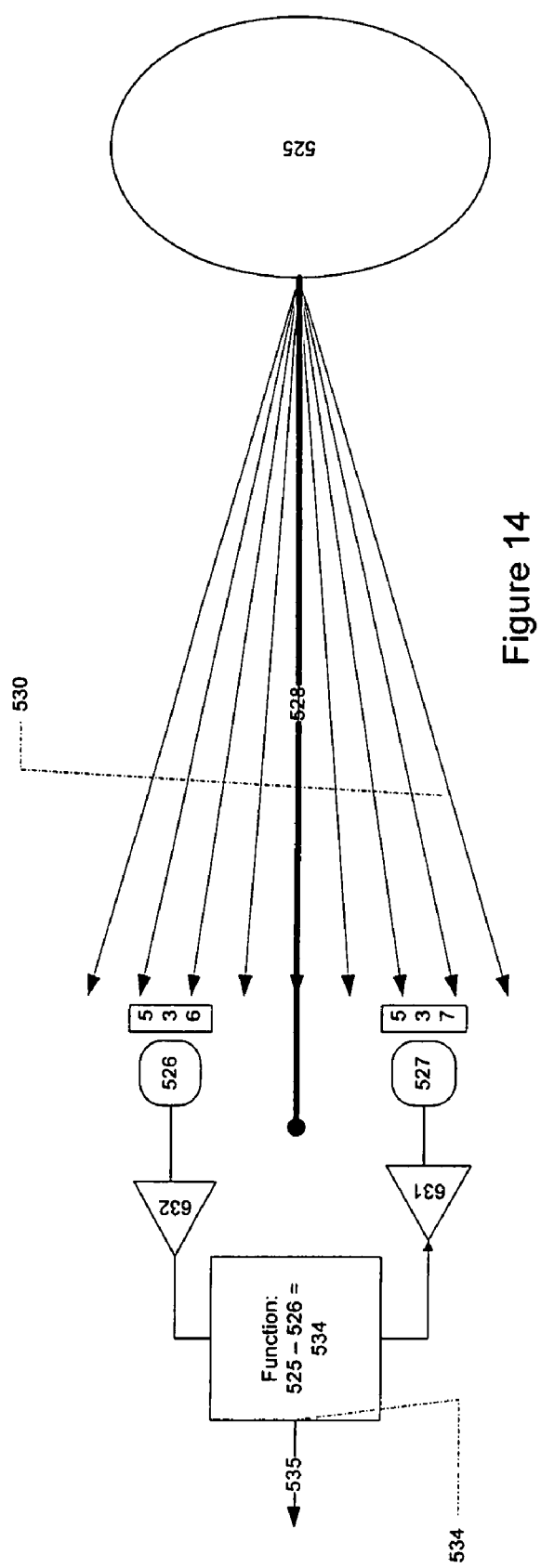
FIG. 14 shows the use of a short wavelength laser in combination with an infrared laser to eliminate the effect of the changing topology of the body as the laser scans across its surface

Referencing FIG. 14, the coaxial combination of the short wavelength and infrared laser 528 is projected onto the body surface. Reflected light 530 is captured by the photo detectors 526 and 527. Detector 526 detects short wavelength light and detector 527 detects infrared light. These detection characteristics may be either a result of one of the signal modulation techniques described elsewhere herein, component selection or through the use of a filter 536, 537 placed in the path of the reflected light.

The output of the photo detectors 526, 527 are amplified and conditioned by pre amplifier circuits 631, 632 and then fed through the differential amplifier 534 which subtracts out the surface topology represented by the reflected short wavelength light yielding an output 535 that is primarily based on the reflected vein pattern.

The simplest embodiment would use a red laser for both detection and projection as described earlier in conjunction with the short wavelength laser.

An Implementation with Three Lasers

As a further embodiment, a three laser system can be built to further enhance the captured and projected image. In this embodiment, three lasers are used: "near" ultraviolet (e.g., 407 nm for imaging the skin topology), visible (e.g., 630 nm providing the visible light for image projection), and infrared (e.g. 740 nm for imaging the veins). Two photo detectors are used. One is for receiving the ultraviolet, and one is for receiving the infrared light. The near-ultraviolet (407 nm) laser has absolutely no penetrating qualities into the skin and therefore the reflection very faithfully reflects the patient's topology. This signal is then subtracted from the infrared signal to yield just the vein signal. This embodiment is further advantaged in that the wavelengths of the ultraviolet and infrared lasers are very far apart from each other, and therefore, there is no inadvertent signal pickup by the respective photo detectors.

This implementation would operate in a substantially similar way to what was previously described for FIG. 14 with the exception that the coaxial laser light source 528 would include three laser inputs: infrared for vein detection, ultraviolet for topology detection and a visible color for projection. Photo detector 526 would be selected for ultraviolet detection characteristics and/or filtered by 536 to provide selective detection of the ultraviolet laser.

Many combinations of multiple lasers and detectors are possible that each provide optimizations based on the type and depth of structure being scanned for, for example adding additional visible lasers for additional projected information as described elsewhere.

Long Pass Photo Detector Filter, Photo Detector Sees Only IR Light

One goal of the photo detector design is to acquire only the desired signal such as the vein pattern without interference from the reflected light from other objects in view such as the topology of the body or ambient light.

Many techniques are possible. In some embodiments, a photo detector will be selected that is matched to the wavelength of the infrared laser. In another embodiment, a filter that has the ability to block all light other than the wavelength of the infrared laser can be placed in front of the photo detector so that only the infrared light passes into the photo detector. In a third embodiment, the amplitude of the laser light is modulated either in the time or frequency domain, thereby allowing the system to know which laser is being seen by the photodetectors. The third embodiment has the benefit of allowing a photo detector that is capable of detecting a broad spectrum of light (e.g., a photo detector that is responsive to both 638 nm laser and 740 nm lasers). This allows a broader range of photo detector devices to be used that are selected for other desirable characteristics such as low cost, small size or greater sensitivity.

Special Laser Handling

As a mirror moves back and forth as it scans the laser beam it decelerates before it reaches a full stop then reverses direction and accelerates again. During some portion of the outer extremes of travel the mirror is moving too slowly for the information returned by the reflected laser to be used. In addition, the output power at these extremes is more dangerous because it is spread over a smaller area. Therefore reducing or blocking laser power in these extremes helps to ensure that it stays within government mandated safety limits. Furthermore, the laser current needed is proportional to the temperature of the laser. This is important in a battery powered device in that the amount of current needed to run a cooler laser is lower and therefore the battery lasts longer.

In the preferred embodiment, one or more of the lasers are turned off during the unused portion at the ends of the scan lines. The benefits of this are:

1. It saves power in the areas that are blind or unusable because of the slow movement of the mirror
2. It reduces overall power used by the laser since it is now off a percentage of the time, reducing the temperature of the laser
3. It extends battery life
4. It is safer, due to less power during the slow moving portion of the scan
5. The active area appears brighter since there is no bright edge to the pattern caused by the slow moving mirror An alternative embodiment would leave the laser on all the time, but change the size of the exit window aperture so that the brighter parts of the scan are clipped off by the window. This embodiment is safer than the preferred embodiment in that the failure mode is less likely to occur, but there is none of the power savings. There are useful benefits to the internal reflection cause by clipping the output however. These include:

1. An internal photodiode can measure the reflected laser light for calibrating the lasers
2. In the case of projecting an image stored in memory, convergence (the need to know exact laser spot position between frames) becomes critical. If the laser beam can hit an extra photodiode when it touches the shade, then that signal can be used for laser spot position sync. If the shade is also mirrored, then the extra photodiode can be placed on the top PC board, to catch the reflected beam.

A further embodiment would be to proportionally reduce the power at the mirror slows so that the brightness is kept constant. This would be useful if a border demarking the edge of the image was desired or if some system data was to be displayed in this border area.

Safety

In some embodiments, it is desirable to maximize the output of the laser so that a greater signal or greater penetration into the body is needed. All laser projection devices have governmental safety agency regulations dictating power output limitations. These limitations are typically expressed as a maximum output of the laser at a given distance from the eye over some period of time. Therefore, a number of techniques that control power output and the time profile of the output can be used to ensure that the device meets these safety criteria.

The balance between high power (yielding brighter images or greater 3*d* penetration) and safety are an important part of the design of the device.

In one possible embodiment, physical barriers can be placed in the design of the product that prevents the user's eye from getting close to the origin of the laser projections. If a user's eye can not get close to the source of the laser, the laser power may be increased. For example, in an embodiment, protruding bars (think of a football helmet cage) can be placed in the direction of the optical path that prevents the user from placing an eye too close to the lasers. Accordingly, the laser power can be increased.

In an alternative approach, signal processing can be utilized to control the power output. By way of example, veins have a very distinctive pattern, (e.g., they are tubular shaped). An embodiment can be created in which the acquired image pattern is stored in a computer memory, image processed to determine whether veins are present, and only upon confirmation of vein being present is the image projected. In this manner, the visible laser is not turned on if the unit is aimed at a user's eye (no vein pattern detected).

In a further embodiment, the power of the infrared laser can be set initially low to detect the presence of surface veins, and only after they are detected is the power of the infrared laser increased (to image deeper veins) and the visible laser turned on to project the vein pattern.

An additional alternative method is to only turn on the device a when a proximity sensor determines the surface, or eye of a user, is a predetermined distance away from the origin of the lasers, for example an Agilent HSDL-9100 proximity detector. The power of the laser can be set so that it is safe at the threshold distance. There are many range detectors known in the art such based on optical and ultrasonic techniques that can be used in the invention.

An additional alternative method is to turn the lasers on for a short duration to determine if a vein pattern is in view before turning the lasers on for an extended period to image the vein pattern.

Since the moving mirrors are subject to inertia, they will move more slowly towards the end of their movement than they do at the center of movement. Therefore, the laser intensity over time is higher at the edges than it is in the middle. The system can be designed to manage the bright edges as follows:

1. In some embodiments, it may be desirable to have the brighter edges since that helps demark the edge of the scan area
2. The housing can be designed so that the exit window clips (or blocks) the edges of the pattern so the more intense light does not exit the device
3. The electronics can be designed so that the amplitude of the transmitted laser is reduced near the edges
4. The electronics can be designed so that the laser is turned off near the edges In all of these embodiments, these techniques can be applied to one or more of the lasers in the system. Furthermore they can be done independently, for example, the visible laser is left on to show the border line, while the IR laser is shut off at the edges.

Ergonomics

The basic invention provides for the detection of and the projection of an image of the pattern of blood vessels directly on to the patient's body. In this manner, the practitioner has a direct sense of where the veins are and where the center line of the vein is so that they may easily and accurately perform venipuncture. One intention of the invention is to be as easy to use as possible. One expression of ease of use is to ensure that the device enhances and doesn't interfere with the normal work process of finding and accessing the vein.

The integration of the detector and projector into a single device also improves on the Crane Patent. In Crane, the vein enhancer implements two separate devices, one for illumination and/or trans illumination and a separate device used for detecting the low light. Such a configuration is awkward and difficult to operate. In addition, having two separate devices increases the likelihood losing one of them.

Scanning Activation Techniques

Several techniques can be applied to allow the user to control operating characteristics of the device such as on/off and gain. This user input is very important from both a safety and operational standpoint. The gain of the scanning system will need to be changed based on skin color and condition as well as the depth of detection desired by the operator. The gain of the projection will also need to be adjusted based on ambient light conditions and skin color and condition.

These include

1. A trigger or switch mounted on the handle of the device in proximity to the normal position of one of the fingers such as the thumb. Such an implementation will be described later.
   a. A trigger or switch that has one position used for on and off
   b. A trigger or switch that has two positions, where the first position puts the device into an aiming mode and the second begins scanning. This type of implementation could be useful in an LED or camera implementation where focal length is limited.
   c. A trigger or switch that has two positions, where the first position is for low gain, and therefore short penetration, and the second is for high gain.
   d. A trigger or switch with a single position that can be tapped multiple times to change the gain of the system
2. A slide switch trigger, where multiple positions along its travel change settings on the device
3. An analog trigger as in a video game joy stick, where the distance of the pull on the trigger is used to change settings of the device
4. A pressure sensitive switch where pressure is used to change settings on the device
5. A rolling thumb control where rolling the wheel in one direction reduces gain and the other direction increases gain
6. Any of the above implemented such that the switch stays in position when it is released and must be manually reset to an off position
7. Any of the above implemented as a dead man switch such that as soon as pressure is removed from the switch it returns to the off position.

Gravity Tilt for Aiming Projection on Skin.

In the present invention there are described a number of novel mechanisms to automatically maintain the position of the imaged area as the practitioner moves the needle to perform venipuncture. It will be appreciated by those skilled in the art that the present invention is not limited to locating veins, arteries and other blood-rich structures and either implicitly or explicitly focused on placing a needle into the structure. There are many procedures, such as an intramuscular injection, where it is desirable not to puncture a vein. The invention can be used to avoid hitting a vein in this case.

Gravity Adjusted

One such mechanism is to mount the imaging head on pivot-able mechanism mounted to the needle protector. The mechanism is arranged so that the force of gravity biases the projection angle at a predetermined angle to the earth's surface. As the needle is moved, the field of view continues to remain at a constant angle to the surface of the earth.

Computer Control Using Orientation Detection

Another mechanism would be to use electronic devices including tilt switches and/or accelerometers to monitor movement of the scanning element. A mechanism such as a switch press could be used by the practitioner to indicate that the scanner should go into a mode where it attempts to maintain the field of view on a fixed position on the body. As movement is detected, the device moves the scan area to compensate for the practitioners hand movement.

Several movement control mechanisms are possible. In one embodiment, positioning actuators can move the scan element in two dimensions thereby moving the imaging/projection area. In another embodiment, the internal mirror arrangement can be such that a bias is added or subtracted from the mirror's travel, thereby changing where the projected image is placed. In another embodiment, a combination of both techniques can be used. In another embodiment, an engine with higher than necessary resolution for vein location can be used and a window is moved within the higher resolution space.

Computer Control Using Feature Detection

The previous embodiment relies on the system detecting a change in its position by measuring the movement of the scan head. In another embodiment, as the image of the vein structure is captured, the system can identify unique patterns in the structure of the captured image. For example, the system could look at a cross point between two veins. In a frame to frame comparison, the change in position within the imaging field of this unique pattern can be determined and then the scan position can be moved by one of the techniques previously described so that the unique pattern is kept in a constant position within the imaging field of view.

Florescent Cream on Skin

In the embodiments previously described, the projection of the image relies on repeated scanning of a visible light source over the area of the body being scanned. It is known in the art that there are materials that emit visible light when energized by a violet or ultraviolet light source. These materials can continue to emit light for a period of time, up to several minutes, after the energizing light source is removed. Furthermore, these materials can be mixed into a gel, cream or liquid base so that it can be applied to the surface of the skin. In addition, the florescent material can be combined with the antiseptic that is already used in venipuncture.

An embodiment of the invention can be made where a violet or ultra violet laser (e.g., 407 nm) can replace the 630 nm laser. The practitioner can apply the florescent material to the surface of the skin and then the scanner can be passed over the area to scan the veins. The device uses the violet/UV laser to activate a pattern that matches the vein position on the treated skin.

This embodiment is very useful and unique for several reasons. First, the image of the vein position is maintained even after the device is turned off and put away, thereby freeing both hands for the venipuncture. Secondly, the size of the imaged area is now limited by the area that the florescent material is applied to, not by the projection area of the device. Third, if the procedure is taking too long, the image can be reactivated by rescanning the area.

Still further, a three laser system can be built, comprising a visible laser for presenting the vein image and a near IR for detecting the position of the veins and a violet/ultra violet for energizing the florescent materials. All lasers are arranged to project along a single axis. Without the violet/ultra violet laser turned on the system operates as described in previous embodiments. However, once an acceptable image is viewed, the 407 nm can be energized to paint the same image as that projected by the 630 nm laser, thereby energizing the florescent material to emit the vein image.

It is known in the art that there are chemical dyes that can change color by exposure to light. Such a material can be substituted in the above embodiments in place of a florescent material.

Distance Aware User Interface

Several control mechanisms that can be used to adjust various operating parameters for the unit are previously described. Another embodiment is to use sensors well known in the art to determine distance to the body surface being scanned. For example, an IRDA module typically used in a laptop computer could be used to sense distance by using the amount of reflection from the IR led back to the photo sensor as a proxy for distance.

These can be added to the device or in a preferred embodiment, the average intensity of one or more of the lasers already in the device can be used to approximate the distance based on the amount of light reflected. This average intensity would vary based on distance.

When the scanner is close, say 6", the scanning angle can be set to maximum and the IR power, signal gain and differentiation levels are set to medium. As the scanner moves away from the body, the scanning angle can be reduced in proportion to the distance. In this way, if the target were for example the arm, the scanned area would not grow as distance increases. This would prevent wasting detection area by preventing the imaged area from growing bigger than the arm.

When unit is moved closer than 6", the level of differentiation, and gain is increased. This is OK to do at close range but at far distances this would cause more false positives—veins would be indicated in places that they do not exist. However, at close range this will show deeper veins. This provides a very intuitive user experience. Move closer—see deeper. Other inventions that use fixed focal length systems and therefore must be kept at a single distance from the body cannot provide this user interface.

Electronics

Time Division Multiplexing Two or More Lasers

In the system design, the photo detector can be selected or filtered so that it is responsive to the infrared laser but not the visible laser. In the manner both lasers can be on at the same time without having the visible laser couple into the photo detector. In some cases, useful attributes of a photo detector such as size or cost would make it preferable to use a photo detector which is responsive to both the visible laser and the infrared laser. In this embodiment, both of the lasers can be pulsed on and off at high rates without affecting the apparent quality of the image (visible light projection) or the quality of the acquired image (the reflections of the IR laser). By synchronizing the two lasers so that while one is on, the other is off, the image acquisition circuits (photo diode and amplifiers) can be arranged to only see signals from the appropriate laser. In this manner the other lasers do not interfere at all with the signal acquisition apparatus.

Frequency Modulation of Lasers

Figure 8B:
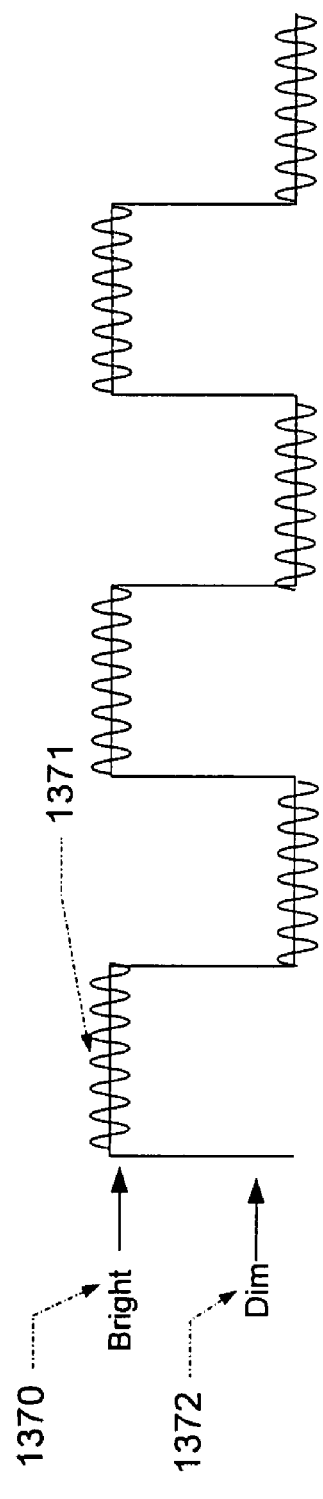

Through the use of amplitude modulation on the transmitted laser, simple filter circuits can be used in the photo detection subsystem to allow one or more laser signals to be differentiated from ambient light and from other laser signals in the system. In FIG. 8, the laser output signal waveform is shown with two levels, bright 1370 and dim 1372. For example, in a single laser system, the bright signal might be used to project and the dim signal would be used to scan. Furthermore, the dim could also be an off state for the laser and this implementation would still be effective.

In the photo detector subsystem, the output of the photo detector can be DC coupled so that no low frequency or DC bias signals pass through to the next stage in the circuit. In this manner, any light, including ambient light, that doesn't exhibit the high frequency modulation, is not seen by subsequent stages of the circuit.

Figure 8C:
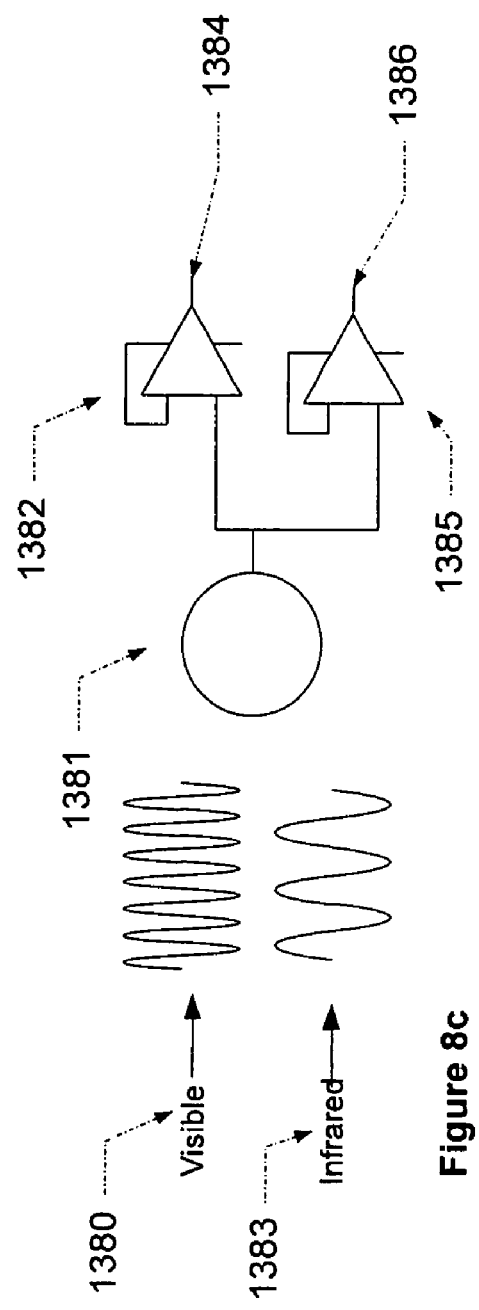

Another mechanism to differentiate between lasers is shown in FIG. 8c. In this embodiment, the lasers are amplitude modulated at different frequencies causing the reflected light received at the photo detector to also be frequency modulated. The visible laser 1380 is modulated at one frequency and the infrared laser 1383 is modulated at another. The light received at photo detector 1381 is a combination of the reflected light from both lasers. The received signal is fed through two different band pass filter circuits. The circuit at 1382 selects for one frequency and the circuit at 1385 selects for the other. Therefore the signal at 1384 and 1386 are representative only of the light reflection from one of the lasers. This can be implemented in a single circuit so that only the infrared vein signal is seen or in two or more circuits where both an infrared vein signal is seen and a long wavelength topology-detection signal is received. A whole range of high pass, low pass, band pass, band block and notch filters can be used based on the technical and business needs of the specific embodiment.

User Adjustments

The system can be arranged as either a binary system or grayscale system. In a grayscale system, the infrared laser signal received by the photo detector is simply echoed and re-transmitted by the visible laser. In this manner, various levels of intensity can be shown. Accordingly, the image of a vein may vary in intensity as a function of the magnitude of signal received.

In a binary system, the projected image is either on or off. To determine whether the projected image should be on or off, a comparator with a trip point is placed after the photodiode. If the signal crosses the trip point the visible laser is turned on and when it falls below the trip point it is turned off.

The system can set these parameters automatically based on built-in rule sets or a user input device like a dial, or push buttons, or any other means of user input could be placed on the device, and the user manually adjusts the trip point (essentially making the device more or less sensitive.)

Some of the parameters that will often need to be controlled to deal with patient and environmental variability include:
 1. Laser intensity
   a. Visible for projection brightness
   b. Infrared for penetration depth
 2. Persistence of vein lock
 3. Selection of vein size to detect
 4. Working range and focus distance
 5. Field of view size
 6. Mirror amplitude IR Modulation Analog or PWM (Pulse Width Modulation)

Throughout all the embodiments, when we discuss adjusting the power of a laser, such adjustment could be made by either adjusting the current to the laser, or alternatively, modulating the laser on and off at a rapid rate (pulse width modulation or PWM). Depending upon the duty cycle, the average laser intensity will be changed. With respect to the visible laser, the human eye integrates the signal and, provided the frequency of the PWM is faster than the eye integration time, the laser will appear as if it was always on, but brighter or dimmer as the on cycle time increases respectively.

The system will also need to adjust the power of the infrared laser. This can be done by adjusting the current to the laser, or alternatively, by PWM. Provided that the PWM modulation is faster than the response time of the receiving means (photodiode plus amplifiers), the modulation will have the same effect upon the received signal as if you reduced the current to the laser.

Simplified Scanning

There are various methods that can be employed for creating a scanned laser pattern. In many embodiments, it is desirable for the scan pattern to be the same from frame to frame and for the system to be able to determine the instantaneous position of the lasers. Such an implementation would allow time consuming processing and integration of data across frames to occur.

In general however, the lower level of position precision that is required, the easier it is to produce the pattern, the lower the system complexity becomes and the lower the cost becomes. In an embodiment without image memory, since one does not need to remember the specific signal at a specific position over time, there is no need for a reproducible scan pattern. Therefore, from frame to frame the laser scan lines do not need to fall reproducibly upon the scan lines of the prior frame and there is no need to know the instantaneous position of the laser. The reason one does not need a reproducible scan pattern or instantaneous position information is that the visible light is coaxially aligned to the infrared laser. The visible light is a function of the received image in real time. Accordingly, whatever location is being imaged is instantaneously being projected.

Scan Amplitude Modulation Scanning

One such simplified modulation scanner which is well suited to this invention is amplitude modulated circular mirror. In this case a mirror is arranged to run at resonance in a circular or oval pattern. The magnitude of the circle is then amplitude modulated at a rate high enough to avoid appearance of flicker. Accordingly, a scan pattern is formed which starts with small concentric circles and grows sequentially larger until reaching a limit and then collapses sequentially to the smallest circle.

Such a pattern has many advantages over a traditional raster scan pattern. Rather than a rectangular shape which would be typical of a raster scan, this method can be used to generate circular or oval pattern shapes. The mirror in this design is always moving and the laser is always actively painting—there are no required off times as the mirrors move into position for the next scan line. The pattern can be adjusted so that it spends more time scanning near the center of the pattern so a brighter, denser, better defined image appears in the center of the scan area. Additionally, the mirror operates at resonance which provides the lowest power dissipation, which is important in handheld battery operated devices.

System Gain Adjustment

It is necessary to adjust the gain of the system during operation in order to ensure that the amount of reflected light is within the proper operating range of the photo detectors.

One method of adjusting the gain is to maintain a constant output from the detection laser and adjust the gain of the photo diode amplification circuitry so as to get an appropriate signal that is neither too low for detection nor too high so that the photo detector or circuit saturates. This approach can become fairly complex due to the speed requirements of the gain adjustment.

Another method is to fix the gain of the photo detection circuitry but adjust the power output of the IR laser so that an appropriate signal is output from the photo detection circuitry (once again not to low or saturated). It is much easier to design circuits that adjust the IR laser due to the extremely high modulation bandwidth of the lasers. As previously discussed, the laser can be adjusted either by analog or digital means.

A laser must be calibrated in that its intensity is sensitive to ambient conditions such as temperature. Some laser diodes have internal mirrors to perform the calibration. An alternative technique is to use the housing of the scanner to block a portion of the light, perhaps an outer scan line and reflect that light back to the photo detector. That reflected light can be used for calibration.

Stored Image, Allows Multi-Scan Averaging

In some embodiments of the invention, the system will have a microprocessor and memory buffer so that the reflected light from the scanning laser will be kept as a representation in memory. By averaging the image over multiple scans, the system can form an image with greater resolution than it could have by only using a single pass of the laser. In order for this to be done, the system needs to ensure that the image elements being captured from scan to scan represent the same physical location on the patient.

The benefit to the system design is that the gain of the photo detector and subsequent analog circuits can be reduced.

Figure 10:
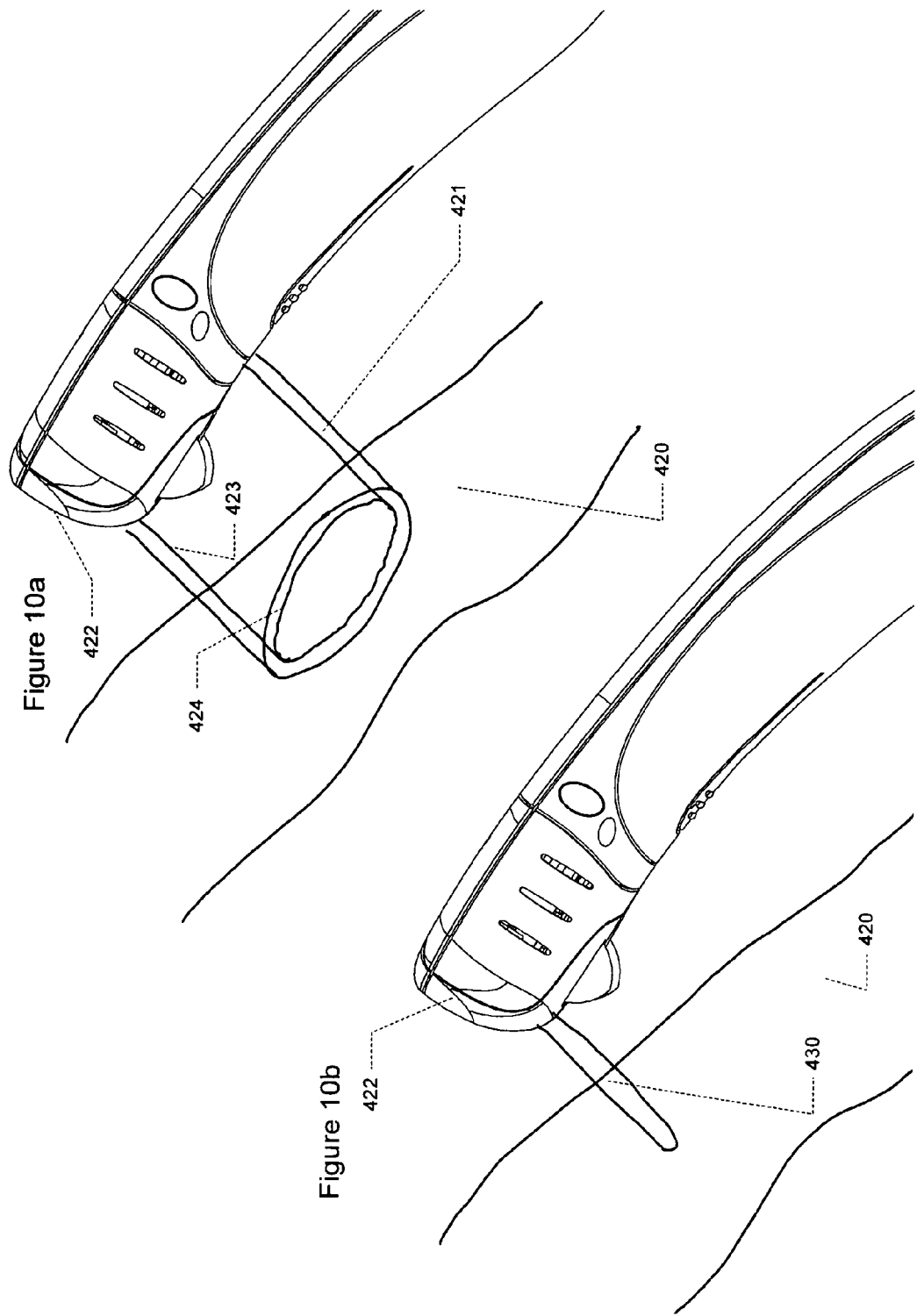
FIG. 10 shows a mechanical focusing mechanism for an LED embodiment of the invention

There are several ways to do this. One is to provide a mechanical stabilization, similar to what was described for the LED implementation (FIG. 10). Many techniques for mechanical, analog and digital image stabilization are known in the art and can be applied to this invention such as best fit correlation.

For example, you can identify a specific point or a group of points within the image in a single frame, for example the cross point between two veins. The system can then adjust the position of the image from frame to frame so that the image elements averaged together represent the same position on the body.

Windowed Vein Tracking

Figure 15:
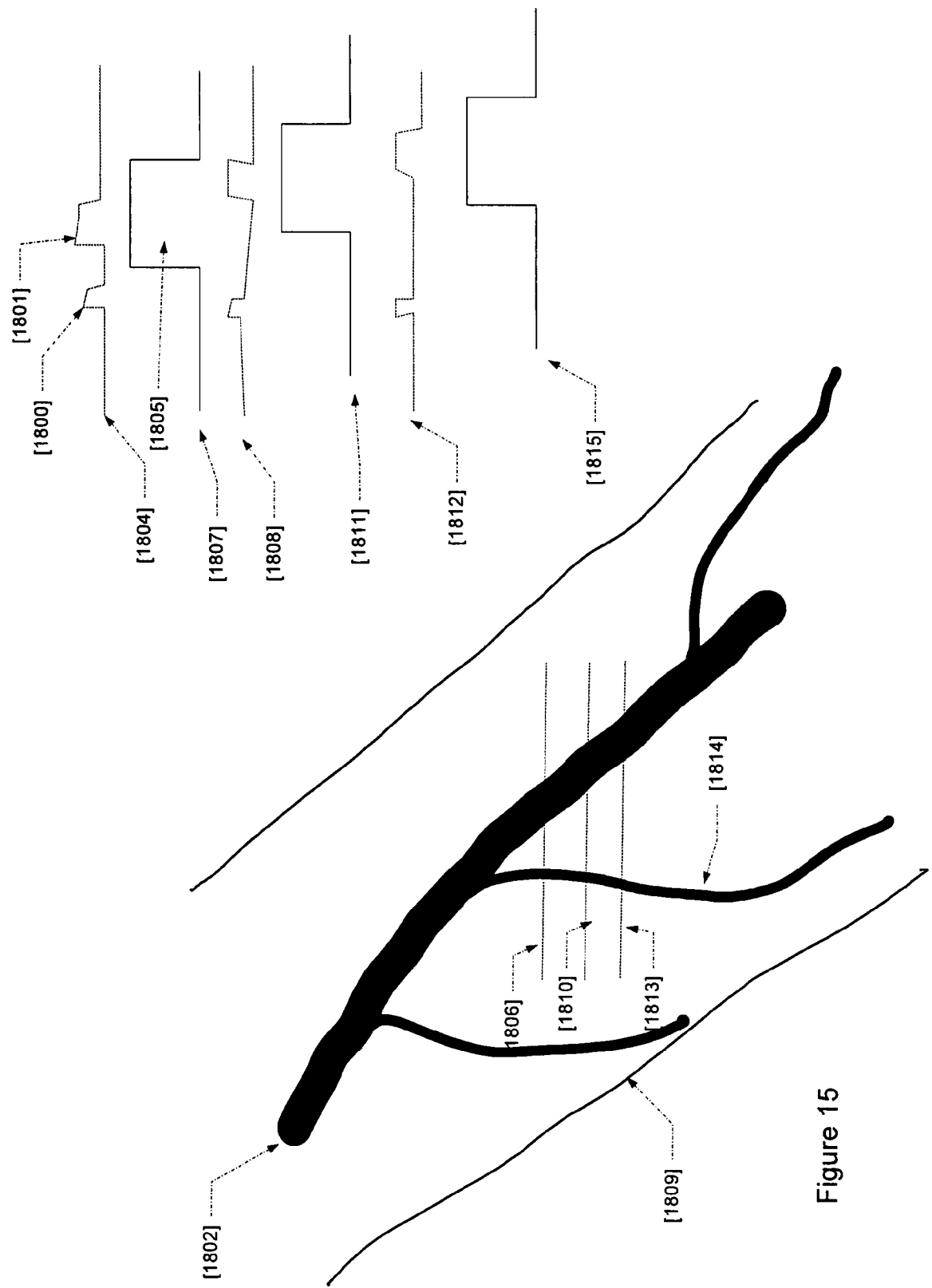
FIG. 15 shows a vein lock system that aids in the discrimination of veins from other structures.
Figure 15B:
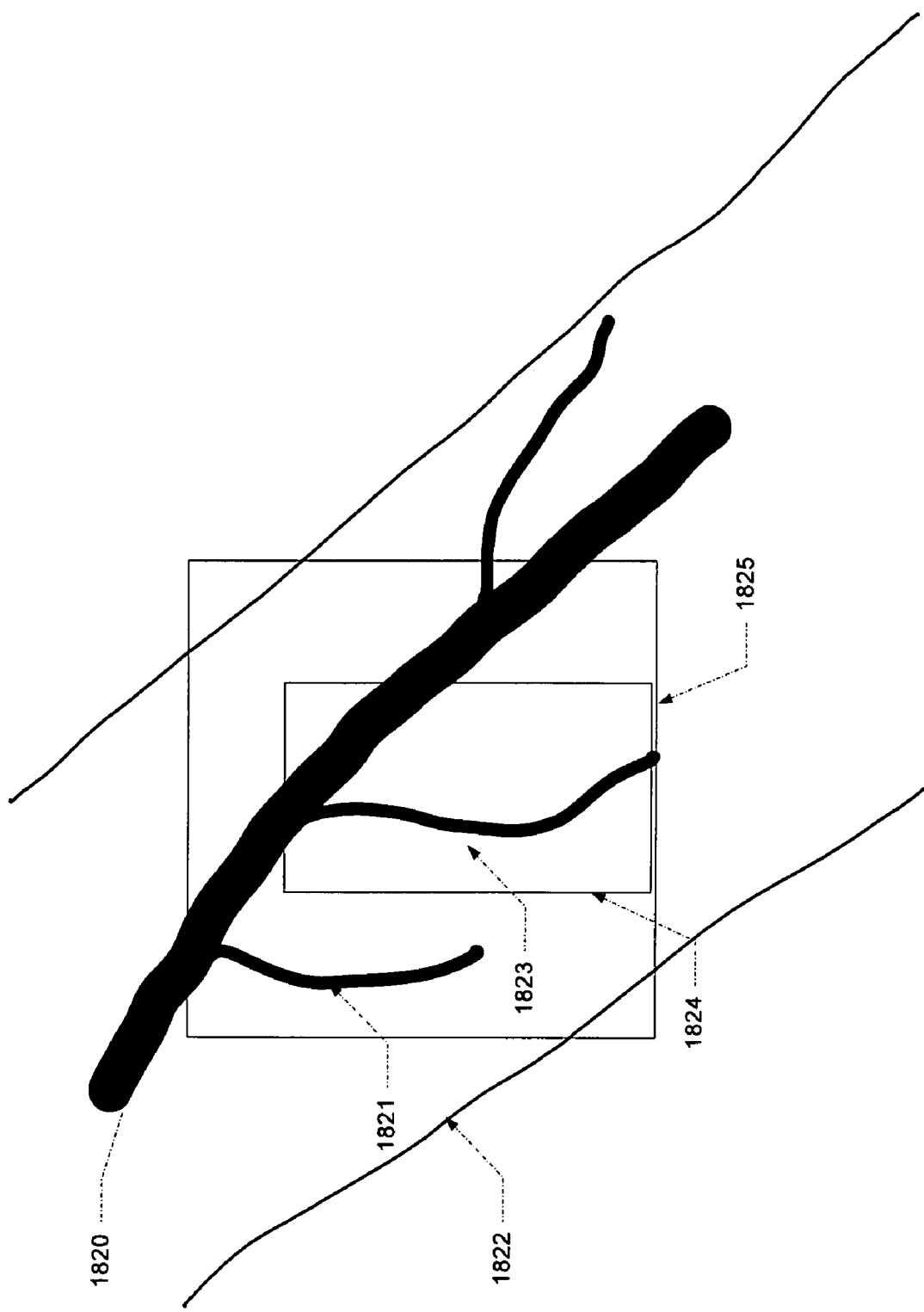
Figure 15C:
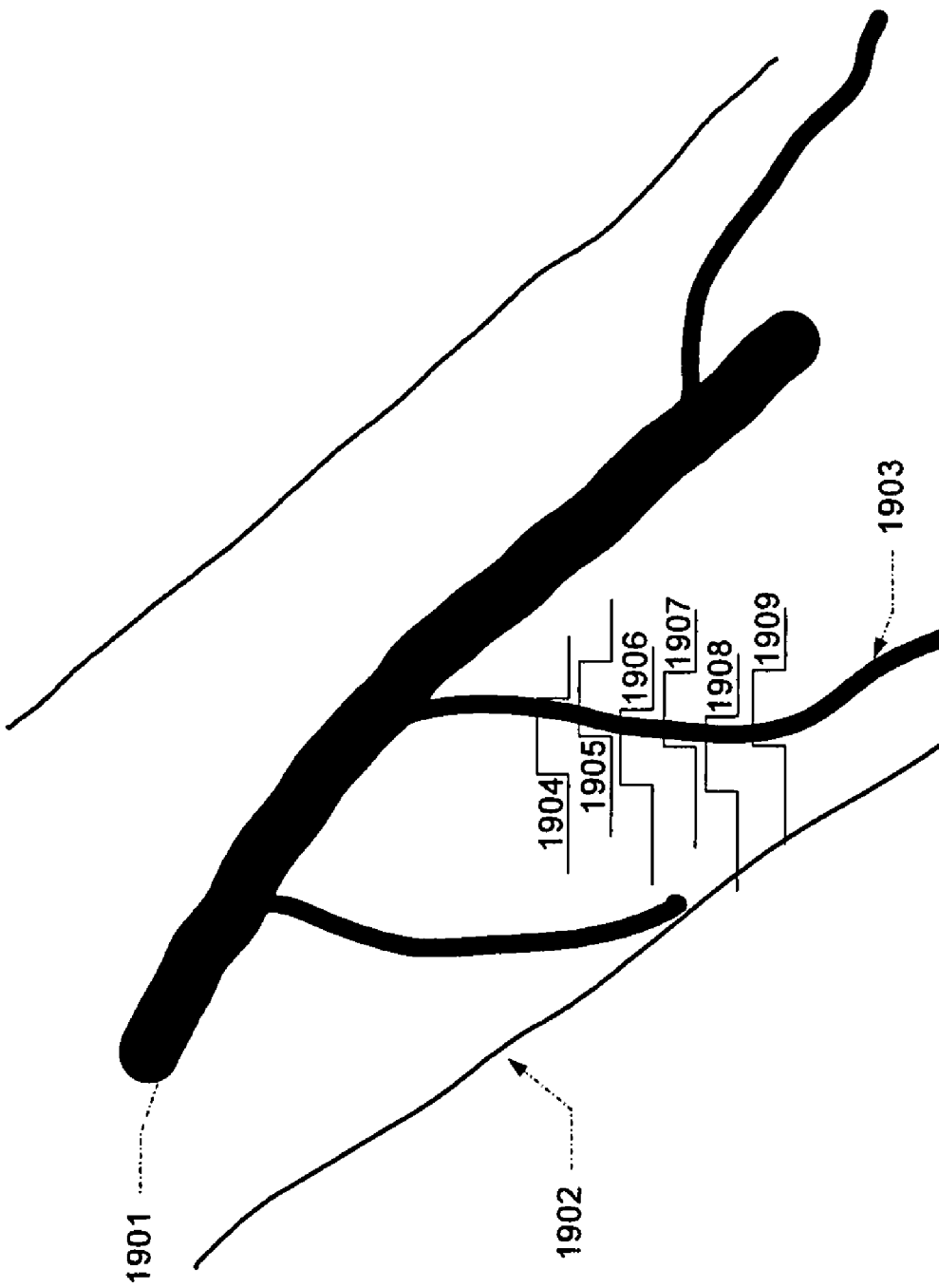

Since veins are linear structures, a novel technique can be used to accurately identify veins and to separately highlight one or more veins and ignore others without using image memory or signal processing techniques. Referring to FIG. 15, a schematic representation of an arm 1809, is shown along with a simplified pattern of veins 1802/1814. As shown, veins are roughly linear structures. Normally, depending on the part of the body the practitioner is attempting vein access, only veins that are oriented in a single direction are typically used to administer medicine or draw blood. For example, on the arm, the veins that run along the long axis of the arm are typically used. Therefore scanning that favors vein detection along that axis is desirable.

A series of scan lines are shown 1806, 1810 and 1813. Each scan line occurs sequentially in time with 1806 first, 1810 second and 1813 last. This technique relies on the fact that once a vein's position is found on a scan line, an assumption can be made where the vein is likely to be on a subsequent scan line. The vein signal can be expected to occur within a small distance to the right or left of the position seen on the previous scan line. Therefore the system can apply a windowing technique wherein vein signals that occur outside the window are given a lower priority or are ignored completely Referring to FIG. 15, a signal diagram to show the windowing approach is provided. 1804, 1808, and 1812 are the reflection signals from scan lines 1806, 1810 and 1813 respectively. In this drawing, a high signal represents greater absorption of the laser light at that point on the body. 1807, 1811 and 1813 are the "windows" calculated based on 1804, 1808 and 1812 respectively. In this drawing, when the window signal is high, detection occurs, when it is low, no detection occurs.

The signal 1800 is caused by vein 1814 and signal 1801 is caused by vein 1802. This simplified example is for a system that is designed to only show the single largest vein in the field of view. By using a system capable of keeping track of multiple windows, multiple veins could be tracked. Alternatively, the sense can be inverted and the vein within the window could be ignored.

Vein 1802 is selected as the vein of interest by some criteria, set in the system or by the user, such as size of vein or the central location of the vein in the field of view. Based on the vein's position as detected by the pulse 1801 on the reflection signal 1804, a window signal 1807 is created that ignores vein reflections that occur outside of the detection window 1805 on the next scan line 1810/1808. Referring to signal 1808, vein 1814 is ignored since it falls outside the window and vein 1802 is detected since it falls within the window. However, since the vein is traveling at an angle with relation to the scan pattern, the vein is now offset within the window. In order to track the vein on subsequent scan lines, the system now re-centers the window 1811 so that when it is applied to the next scan line 1813/1812, the vein falls within the window. This process repeats for the entire field of scanning.

A user interface can be implemented allowing the user to select a number of veins to detect simultaneously and to switch focus from vein to vein. Also, the user could control the width of the window to optimize the detection of the vein. Additionally, the user can turn this feature on and off so that they can either see all veins or just a specific vein or veins. Since there is inherent directionality to the procedure, the user can rotate the scanner to see only those veins at a particular orientation.

Diagrammatic Walkthrough
Walk Through of the Engine

In FIGS. 17 through 22, an embodiment of the device is presented. This implementation uses two lasers, one infrared and one red. The lasers are made coaxial through a series of bounce mirrors and are combined by a dielectric mirror. Two moving mirrors are used to move the beam in a raster pattern which then exits the engine and strikes the patient's body. The collection path includes two spatially separated photo diodes. The electronics use an analog, real time approach whereby the detection of a vein causes an immediate reduction in the projected visible light at the point at which the vein is detected. The operator sees this pattern of dark lines directly on top of the position of the veins.

Figure 17:
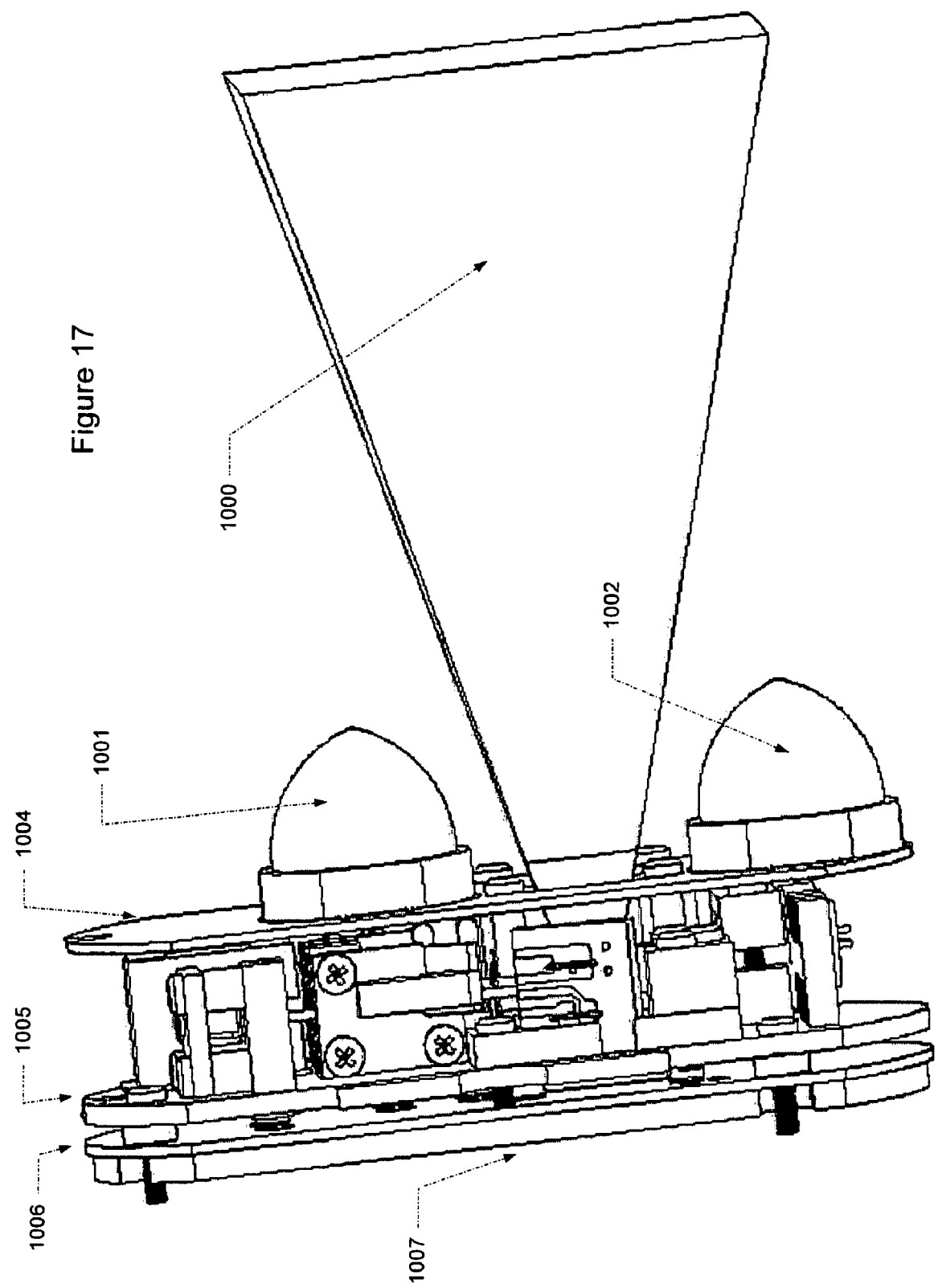
FIG. 17 shows a side view of a prototype embodiment of the invention.

Referring to FIG. 17, the scanning engine is shown as an assembly including a detector deck 1004, an optical deck 1005 and a circuit board 1006. Both mechanical and electronic parts are mounted on these boards. The engine is oriented so that the laser scanning pattern 1000 projects perpendicular to the boards through an orifice in the detector deck 1004. The photo detectors 1001-1002 are aimed along the same axis so that they have a clear view of the reflected light.

Figure 18:
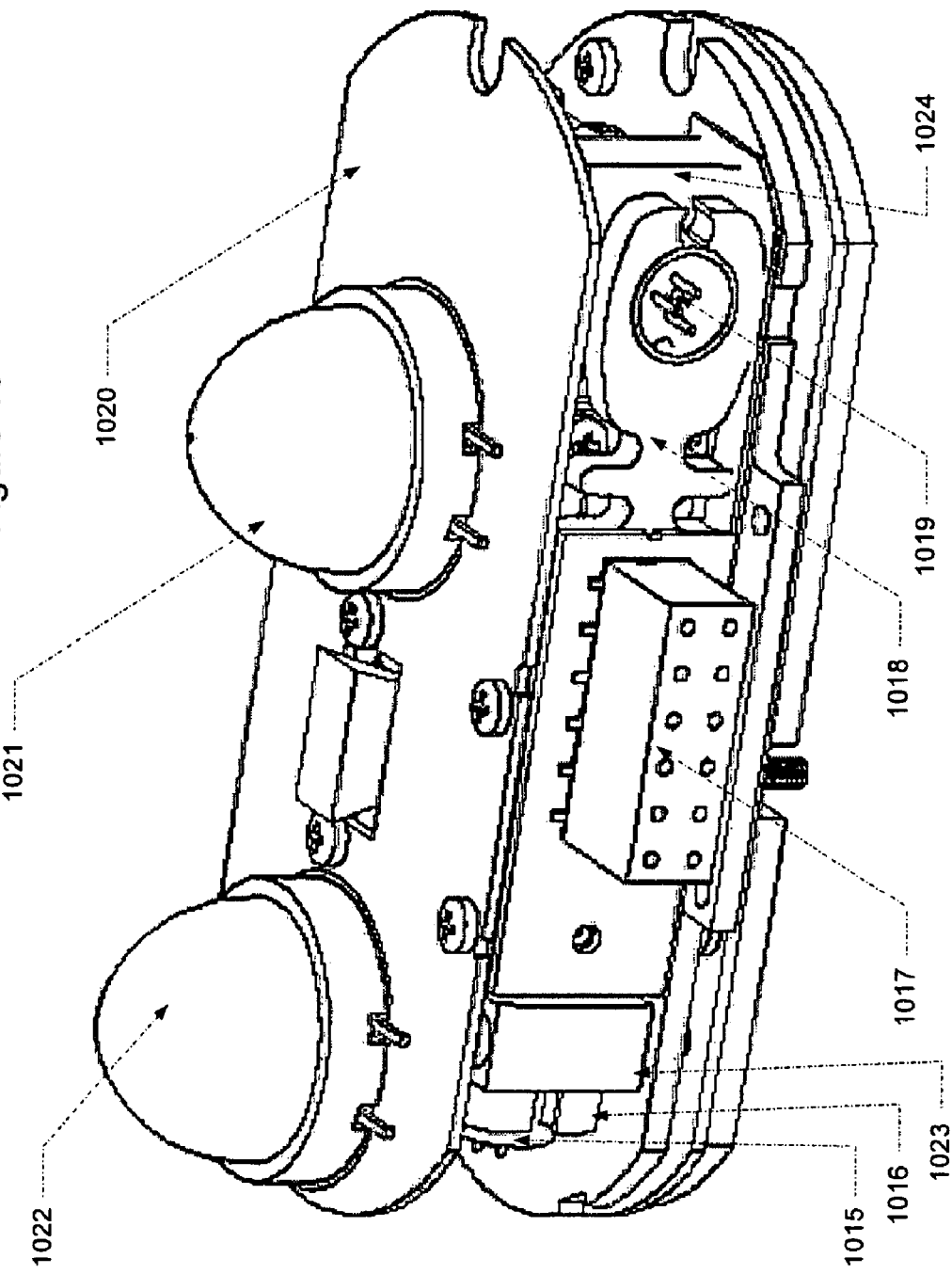
FIG. 18 shows an alternate side view of a prototype embodiment of the invention.

In FIG. 18, the visible laser diode 1015 and infrared laser diode 1019 are arranged for best fit within a miniature form factor of the engine and therefore rely on a series of bounce mirrors to realign the beam. Both laser diodes are mounted to holder assemblies 1023/1024 and heat sinks 1016/1018. Proper thermal management of the diodes extends their working life and increases the reliability of the engine.

An optional connector 1017 is mounted to the side of the engine to allow it to be used in an embodiment of the device that allows the scan head to be removed from the portable handheld device and mounted on an alternative base such as a tabletop stand.

The detector deck 1020 is a printed circuit assembly that holds the photo detectors 1021/1022 as well as other electronic components necessary for the operation of the engine. For example, the pre-amplifier circuitry for the photo detectors will typically be mounted in close proximity to the detectors 1021/1022 so that noise in the system is minimized.

The photo detectors 1021/1022 are shown with integrated dome-shaped lenses to increase sensitivity in the direction of the reflected laser. Various schemes both with and without lenses can be implemented in engine embodiments. In addition, filters can be placed in front of the photo detectors so that the wavelength of light they respond to can be specified.

Figure 19A:
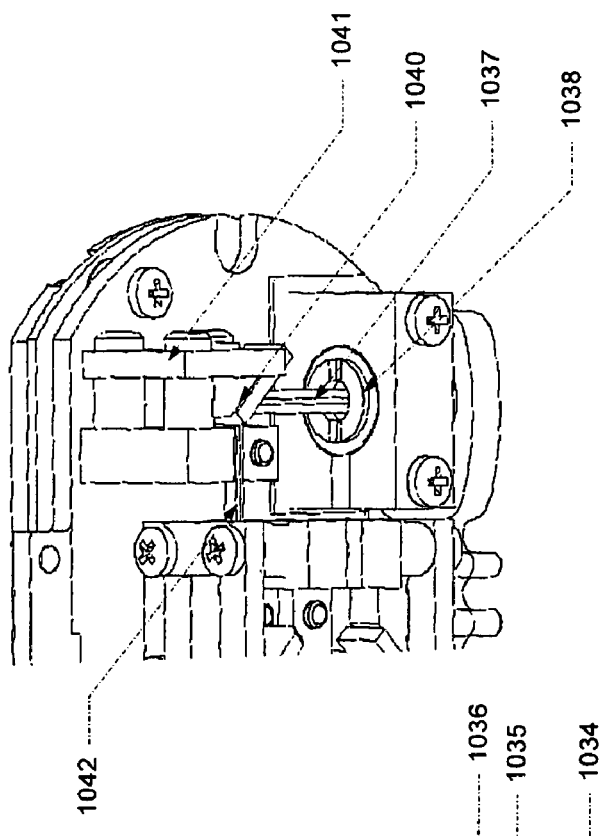
FIG. 19 shows views of several sub assemblies of a prototype embodiment of the invention.
Figure 19C:
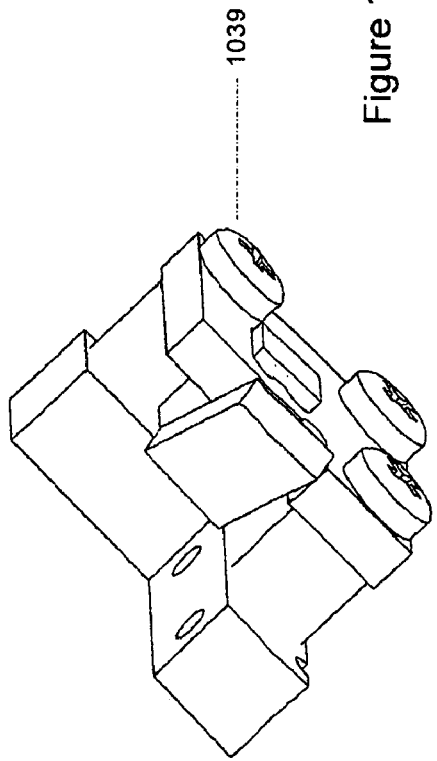
Figure 19B:
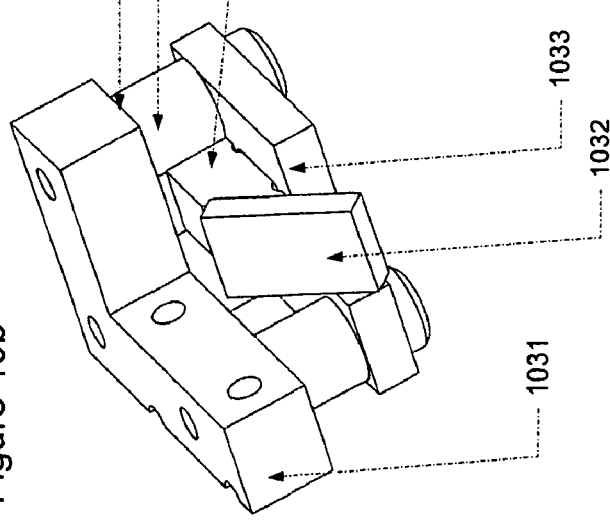

In FIG. 19 *a-c* which is an illustrative example, several views of the bounce mirror assemblies are shown. Since the intent of the design is to make two or more laser beams coaxial, proper alignment is critical. Shown is one of the exit windows from the laser diode 1038 with the beam 1037 striking the mirror 1040 thereby reflecting the beam into the new desired orientation 1042. The mirror is held in position by an adjustable holder 1041.

The holder assembly 1041 is comprised of a fixed platform 1031 that is fastened to the optical deck in a fixed manner. The mirror 1032 is attached to a wedge 1034 that is angled in the desired manner to reflect the beam in the appropriate direction. The wedge is fixed to a floating deck 1033 which is attached to the fixed platform 1031 through a number of screw 1035 and spring 1036 assemblies. The spring 1036 is placed around the screw 1035 and is compressed by the two platforms 1033/1031 so that the springs provide a constant force against the two platforms ensuring that they are held as far apart as the screws will allow. The screws (e.g., 1039) pass through an unthreaded hole in the floating deck and into a threaded hold in the fixed platform 1031. By tightening or loosening the screws, the decks are moved closer or further apart. Through the use of multiple screws, several degrees of freedom of adjustment are obtained, thereby allowing the beam to be properly aligned along the desired path.

In this design, three of these bounce mirror assemblies are used. This design uses mechanical screws to fine tune the position of the mirrors and in practice would be locked in place once positioned with an adhesive material such as locktite. High volume configurations of the product could use robotic assembly and the mirrors would be positioned and then welded, epoxied or glued into place eliminating the cost and complexity of the screw/spring assembly.

Figure 20:
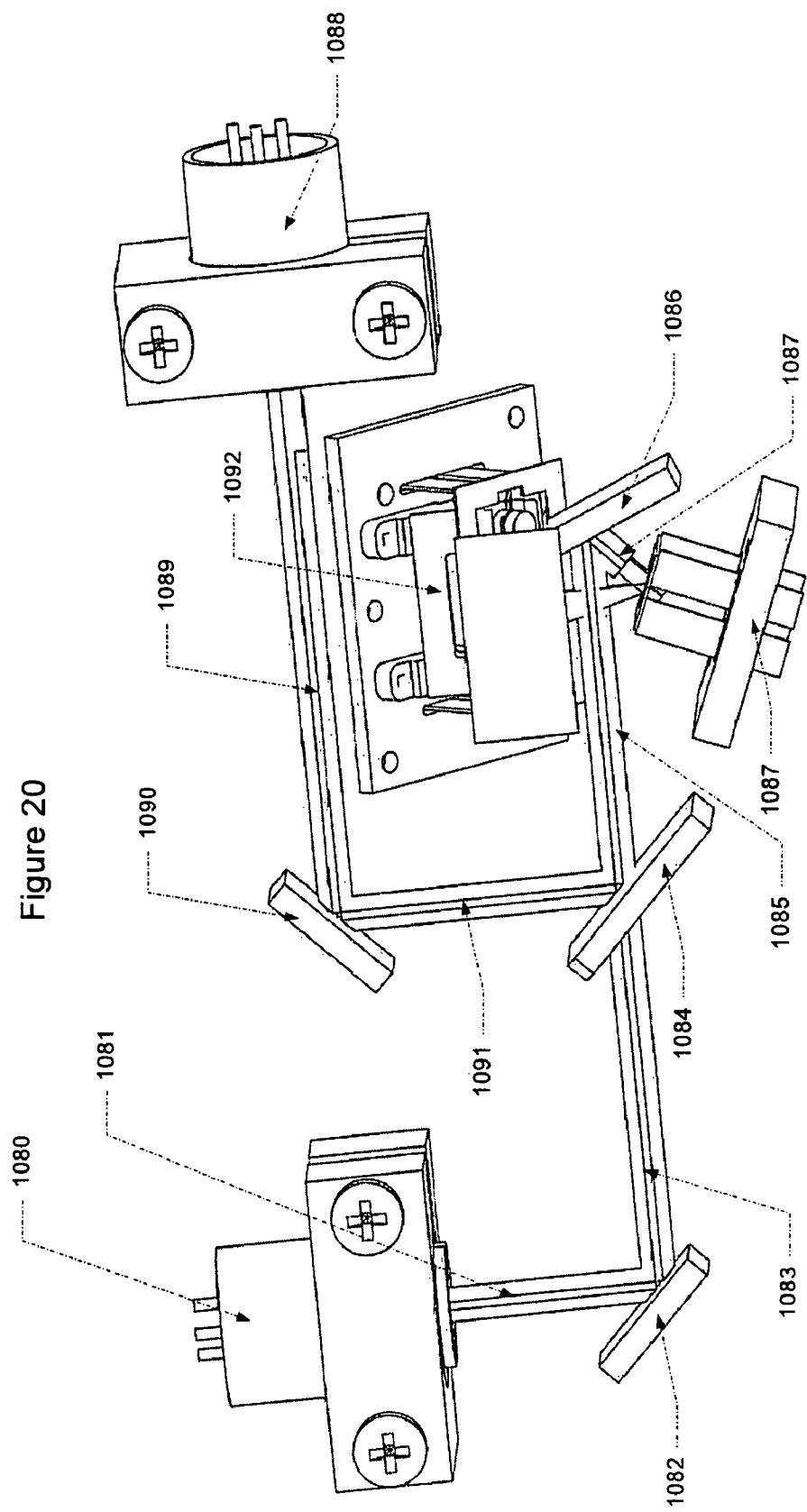
FIG. 20 shows a view of the prototype embodiment with parts removed so that the laser path and the key components controlling the laser path are visible.

Referring to FIG. 20, the path of the laser beams are shown. Many parts have been removed from the diagram to allow the beam path to be easily seen. The laser diode 1080 emits a beam 1081 which strikes the angled mirror and is reflected along path 1083 which then strikes the dielectric mirror 1084. The mirror's characteristics are selected so that this beam passes through mirror 1084 and exits along path 1085.

The second laser 1088 emits its beam along path 1089 which then is reflected off of mirror 1090 along path 1091. The beam 1091 strikes the dielectric mirror 1084 which as been coated to reflect the wavelength of light emitted by laser 1088. Therefore, the beam is reflected along path 1085. At this point the two lasers are now coaxial. The beams 1085 are reflected off of mirror 1086 and are reflected along path 1087 so that it strikes the moving mirror that is part of assembly 1087. This fast-moving mirror is oriented to provide the x-axis scanning. The light is reflected onto the mirror in assembly 1092 which is a slower moving mirror that provides the scanning in the y-axis. In this diagram, the resulting scanned beam pattern exits out towards the back of the drawing.

Figure 21:
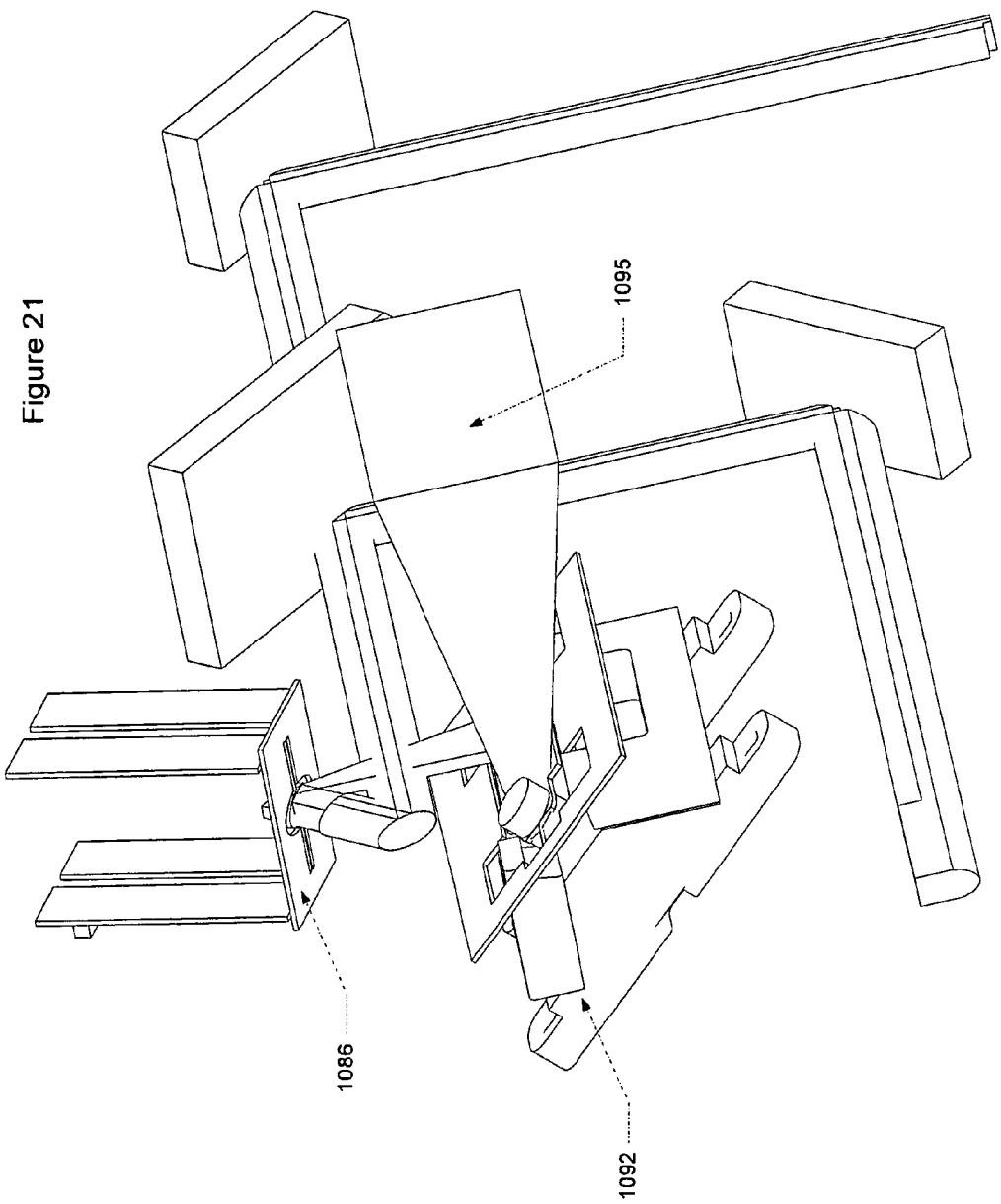
FIG. 21 shows an alternative view of the prototype embodiment with parts removed so that the laser path and the key components controlling the laser path are visible.

In FIG. 21, which is an alternative view of the previous drawing, the scanned laser beam exit pattern 1095 is seen more clearly.

Figure 22:
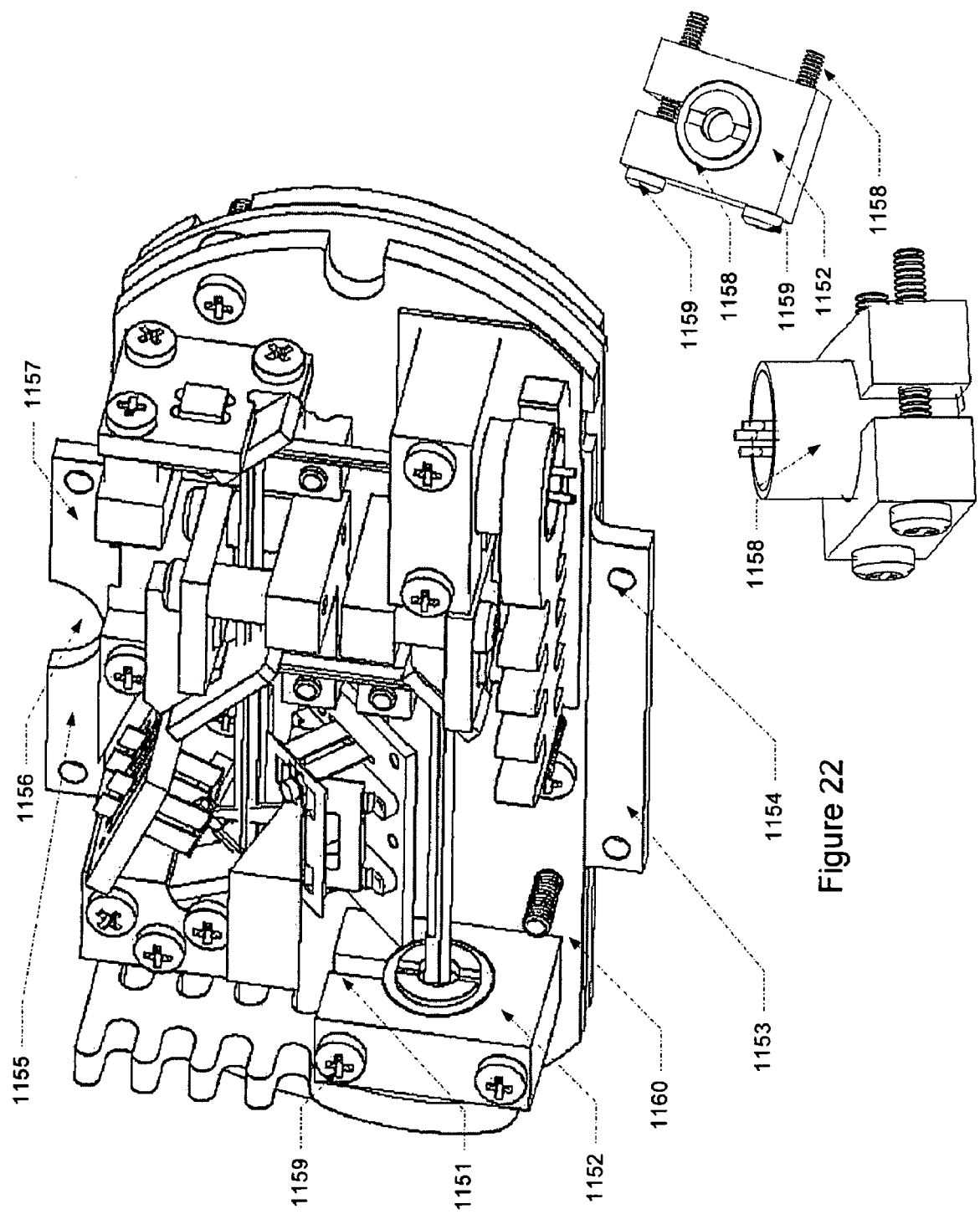
FIG. 22 shows a view of the prototype embodiment with a circuit board removes so that additional elements are visible

In FIG. 22, additional novel features of the design are seen. The laser diode mounting bracket 1152, is a split ring design. The screws 1159 pass through unthreaded holes in the bracket 1152 and into threaded holes on the optical deck 1160. By tightening the screw on the split side of the bracket 1152, the laser diode assembly 1158 is compressed and held in place. This allows the position of the diode to be locked in both an in/out orientation and in rotation. Locking the rotation position is critical in designs that use the laser's polarization rather than wavelength for beam alignment.

The engine uses extensions 1153, 1155, 1157 on the circuit board to provide mounting features so that the entire engine assembly can be firmly mounted into a housing. The extensions could also have been on the detector deck or optical deck or on one or more of the mechanical components of the engine. Holes such as 1154 are provided so that either a screw or a boss can be used to align and hold the engine in the housing. The extensions can be held in place with screws or by captivating them in a feature of the housing. The extensions can be made in a range of shapes so that they do not interfere with features in the housing. For example, the notch 1156 is designed so as not to interfere with a boss in the housing.

In the current design, the high speed mirror 1111 is implemented with a Texas Instruments TALP3400 and the low speed mirror 1111 is implemented with a Texas Instruments TALP4500. The red laser diode 1111 is a Sanyo DL-LS1148 and the infrared laser diode is a Sanyo GH0781JA2C. The laser lens 1111 is a Thorlabs, Inc. 350150-B and the photo diodes 1111/1111 are Hamamatsu S6968-01.

Figure 23:
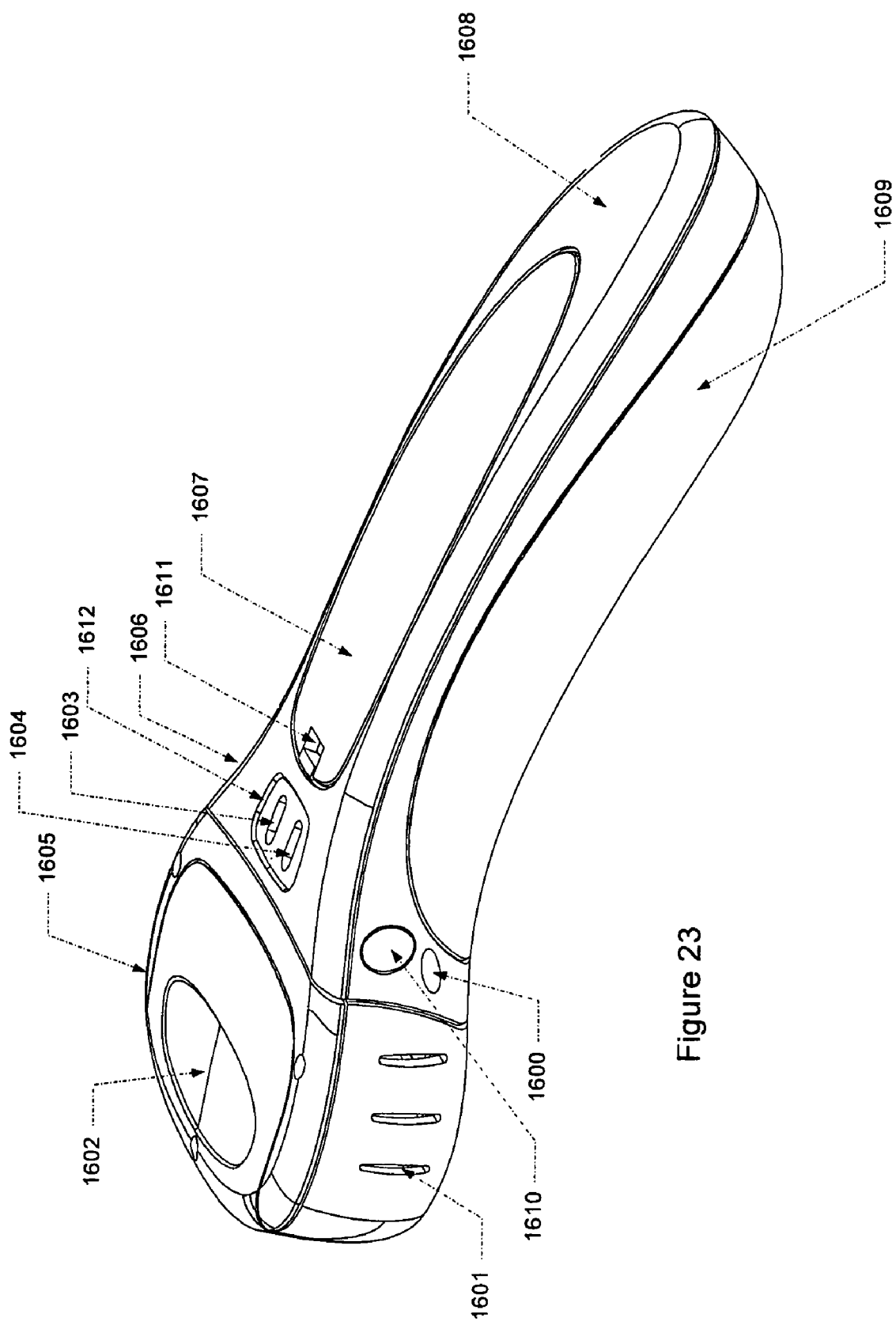
FIG. 23 shows the enclosure of a prototype embodiment from a top-side view.

Referring to FIG. 23, one embodiment of a portable handheld vein scanner based on the engine described previously described. It will be appreciated that this device is just one example of the design of the present invention and that the shape and features can be altered to fit the end user's needs while still employing the teachings of the present invention. This embodiment is typically a two piece design with a detachable head 1605 connected through a friction fit; a snap on mechanism or other suitable means to a handle 1606. The buttons 1610, which are on both sides of the handle, are designed so that when they are pressed, latches that hold the scan head and the handle together are released and the user can separate the two pieces. Screw holes 1600 on both sides of the handle are provided along with matching internal bosses in the scan head allow the handle and head to be permanently attached should the deploying organization wish to prevent the separation of the parts.

The handle is composed of a top housing 1608 and a bottom housing 1609 that are snapped and screwed together to form a single unit. The battery door cover 1607 completes the handle package. This door cover 1607 is designed to be removed by the user with the latch 1607. There is also provision for a screw hole in the battery door and a matching hole in the inner housing should the deploying organization wish to prevent the end user from accessing the battery.

In the top portion of the handle, two LED openings are provided 1603, 1604. These are illuminated by LEDs on a board inside the handle and provide important status information to the user. The openings at 1603 and 1604 can be filled with a light pipe or pipes to bring the light up to the top surface and can be covered either with a molded light pipe or with a label that fits into the opening at 1612. An inset area is provided at 1602 that allows for a label to be positioned providing a company logo, a product model identifier or other user viewable indicia. Since the top and bottom are separable, it may be desirable to repeat identical or other labeling information on the handle part as well. Additional labels can be placed on the inside of the battery door, battery compartment or on or near the scanner opening on the other side of the scan head 1605.

As seen in the engine design discussions, thermal management of the laser is critical to minimizing power consumption and life of the laser. Therefore, openings 1601 are provided on both sides of the scan head to allow convection cooling of the scan engine. In certain embodiments, it might be desirable to have a fully sealed unit. In this case, the openings will be eliminated and other techniques well know in the art will be used to cool the lasers. For example, the heat sinks on the engine can be continued on the outside of the housing.

Figure 24:
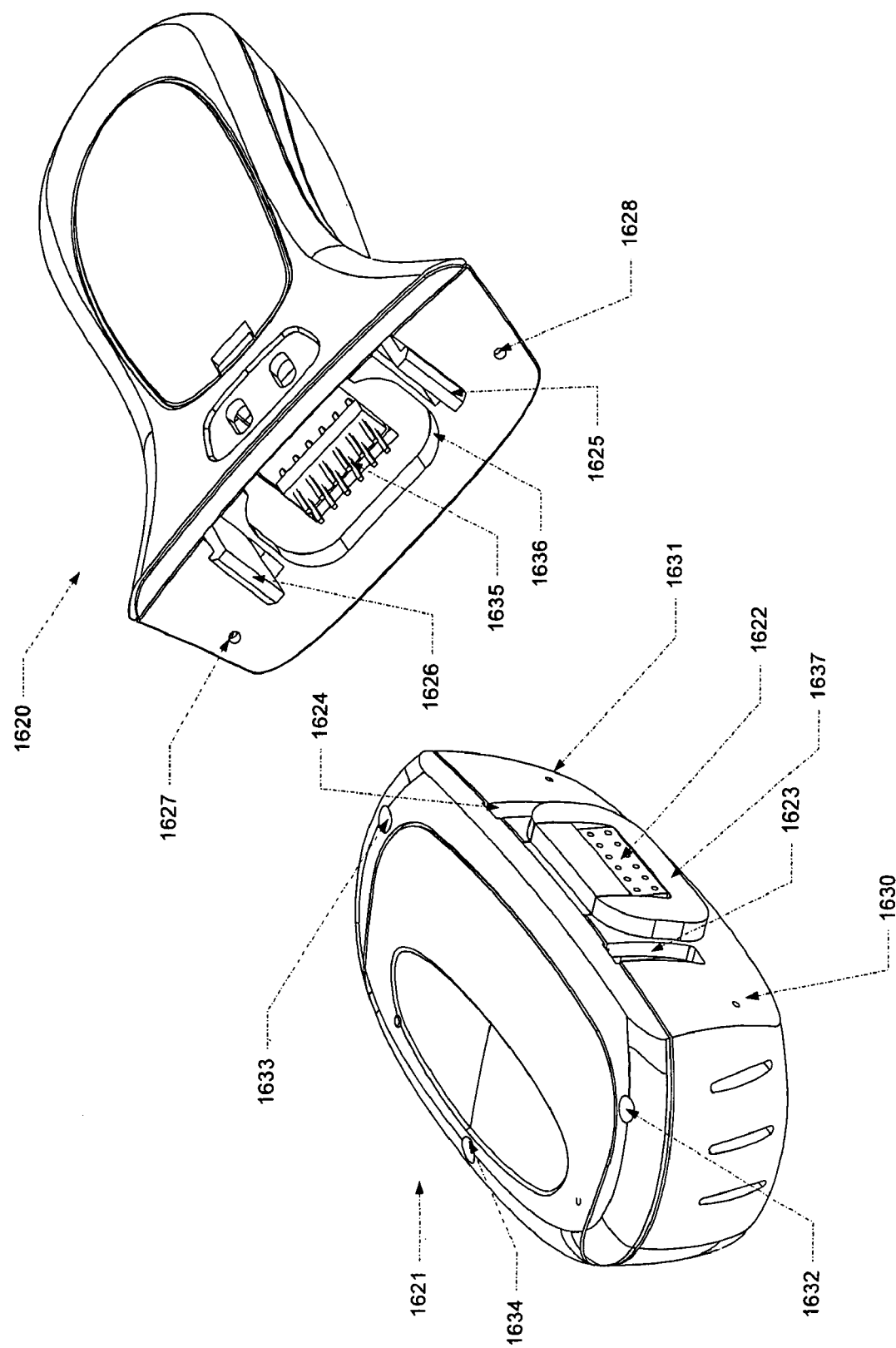
FIG. 24 shows the enclosure of a prototype embodiment with the scan head separated from the handle.

Views of the handle 1620 separated from the head 1621 are shown in FIG. 24. 1630/1631 are the matching screw holes for the optional screws 1600. These holes are designed to engage the threads on the screws. The holes 1627/1628 line up with these holes and do not engage the threads, but are designed so that the screw heads apply pressure against the head and handle thereby keeping them connected.

Further screw holes are seen at 1634, 1633, 1632 that hold the top and bottom plastic pieces of the scan head together. Internal mating bosses are provided in the lower half of the scan head housing.

Mating latches 1626/1625 and holes 1623/1624 hold the scan head and handle together. The latches 1625/1626 are internally sprung so that when the buttons 1610 in FIG. 23 are not pressed, they captivate the outside edge of the slots 1623/1624. When the buttons 1610 are pressed, they no longer engage the slots 1623/1624.

Two mating electrical connectors 1635 and 1622 are provided so that the battery, switch and other electronics in the handle 1620 connect to the electronics in the head 1621. A shoulder 1637 and a matching inset 1636 are provided to ensure proper alignment of the connectors as the head and handle are separated and re-connected.

Figure 25:
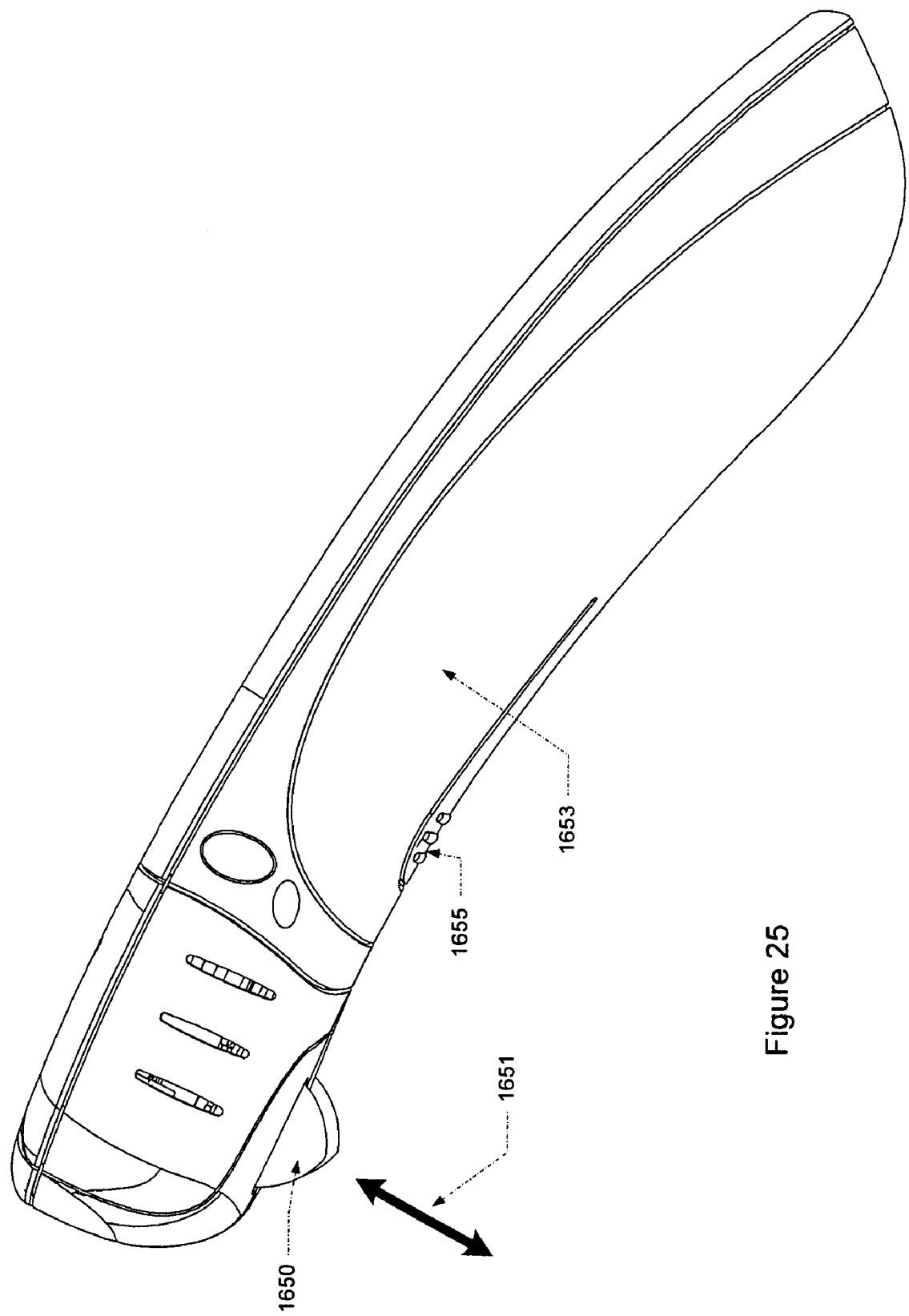
FIG. 25 shows the enclosure of a prototype embodiment from a side view.

In FIG. 25, the head and handle are shown attached. A trigger that allows the user to control the operation of the scanner is shown at 1655 and 1662 (See FIG. 26). This trigger is molded as part of lower housing 1653 and internally comes in to contact with an electrical switch. The hinged part of the lower housing that forms the trigger 1655 is designed so that it has an appropriate level of force so that the user doesn't accidentally trigger the unit but doesn't have to press to hard either. The mating electrical switch is selected so that the user gets positive tactile feedback of the switch closure.

Figure 26:
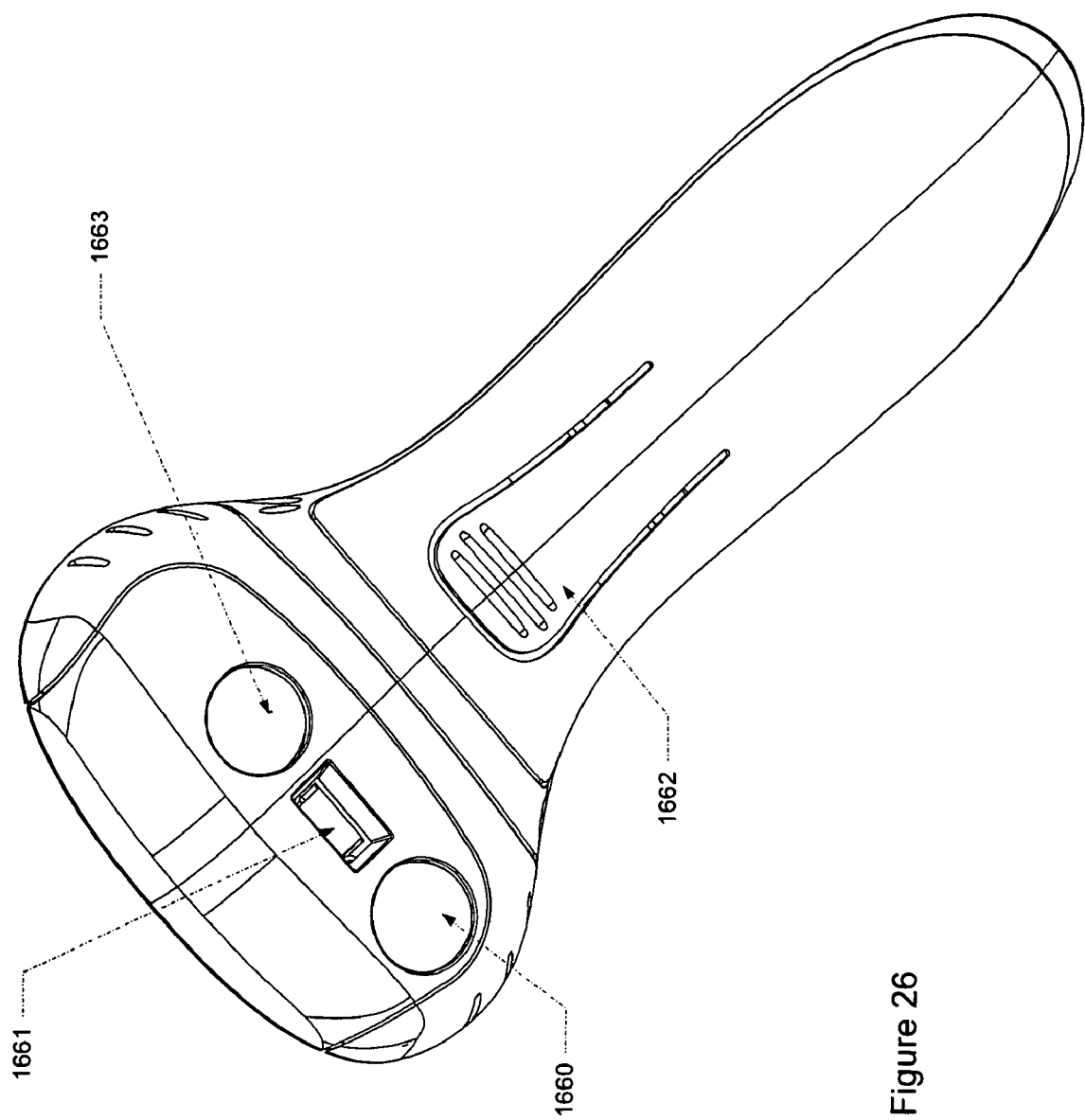
FIG. 26 shows the enclosure of a prototype embodiment from the bottom.

The lenses for the photo detectors are shown at 1650. They are aligned in the same plane as the emitted laser path 1651 so that they can pick up the reflected light from the target area. In FIG. 26, the photo detectors 1660/1663 are shown arranged around the laser exit window 1661.

Figure 27:
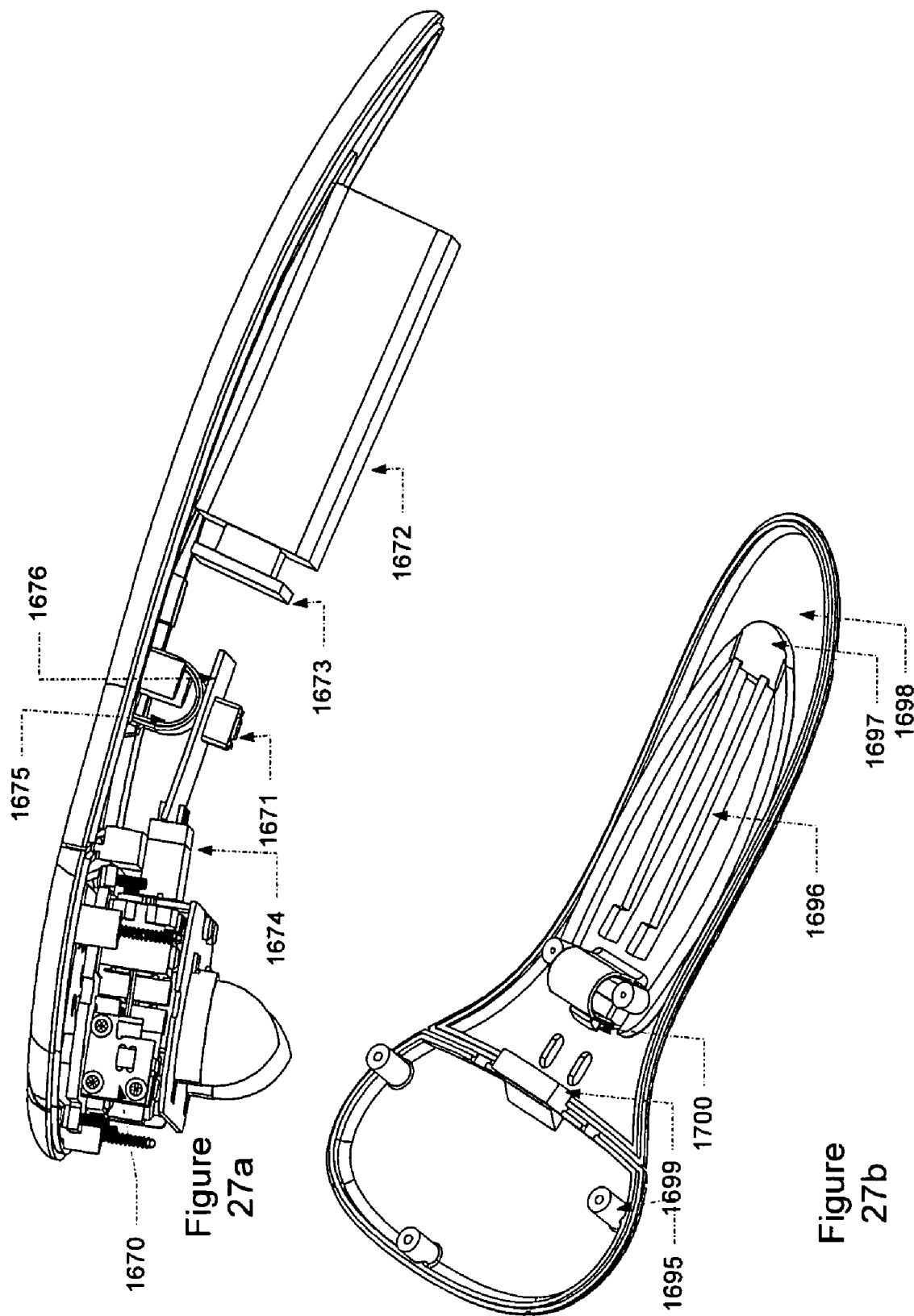
FIG. 27 shows the enclosure of a prototype embodiment from with the top and bottom separated so that the internal assembly is visible.

FIG. 27a is shown with the lower housing of both the handle and the head removed FIG. 27b showing the position of the scan engine 1670, the paired electrical connectors 1674 and the electrical switch 1671 that were described earlier. A PCB 1676 is show holding the switch, the LEDs and the connectors 1674 previously described. A second PCB that mates to the battery connectors is at 1673.

The battery door spring mechanism is shown at 1675. The loop in the mechanism provides force in the forward direction (towards the head) thereby engaging the latch. A second view of the door and the latch mechanism is shown in drawing 27b with the tongue 1697 that engages the handle top housing 1698 and the clip on the latch 1700 that engages the handle top housing at the other end of the battery door.

One of several screw bosses 1695 is used to connect the top and bottom halves of the housings. Furthermore, an alignment standoff is shown at 1699.

Figure 28:
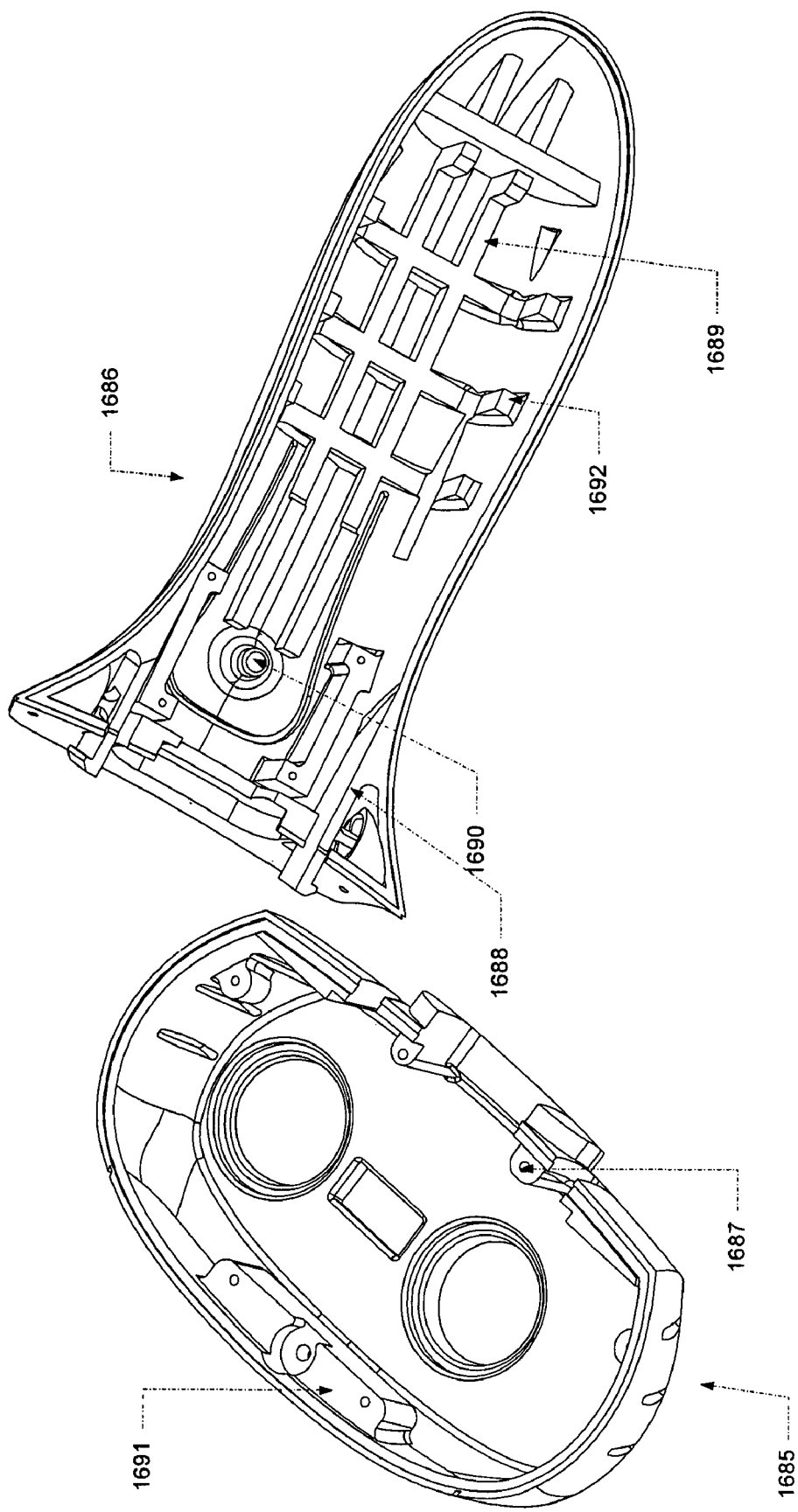
FIG. 28 shows the top part of the enclosure of a prototype embodiment with the other parts removed.

Referring to FIG. 28, which shows the cavity/rear housings of both the head 1685 and handle 1686, several additional details are revealed. Bosses 1691 and 1687 provide mounting for the mounting tabs on the scan engine described earlier. These can be secured with screws or can be captivated between the two halves of the housing. An alternative design could captivate the engine in shock absorbing materials to increase the ruggedness of the device.

Further detail of the spring latch mechanism described earlier can be seen at 1688 and the contact point/stud for the electrical switch from the trigger is shown at 1690.

Ribbing that performs the multiple function of strengthening the housing and locating the battery is shown at 1689 and 1692.

Figure 29:
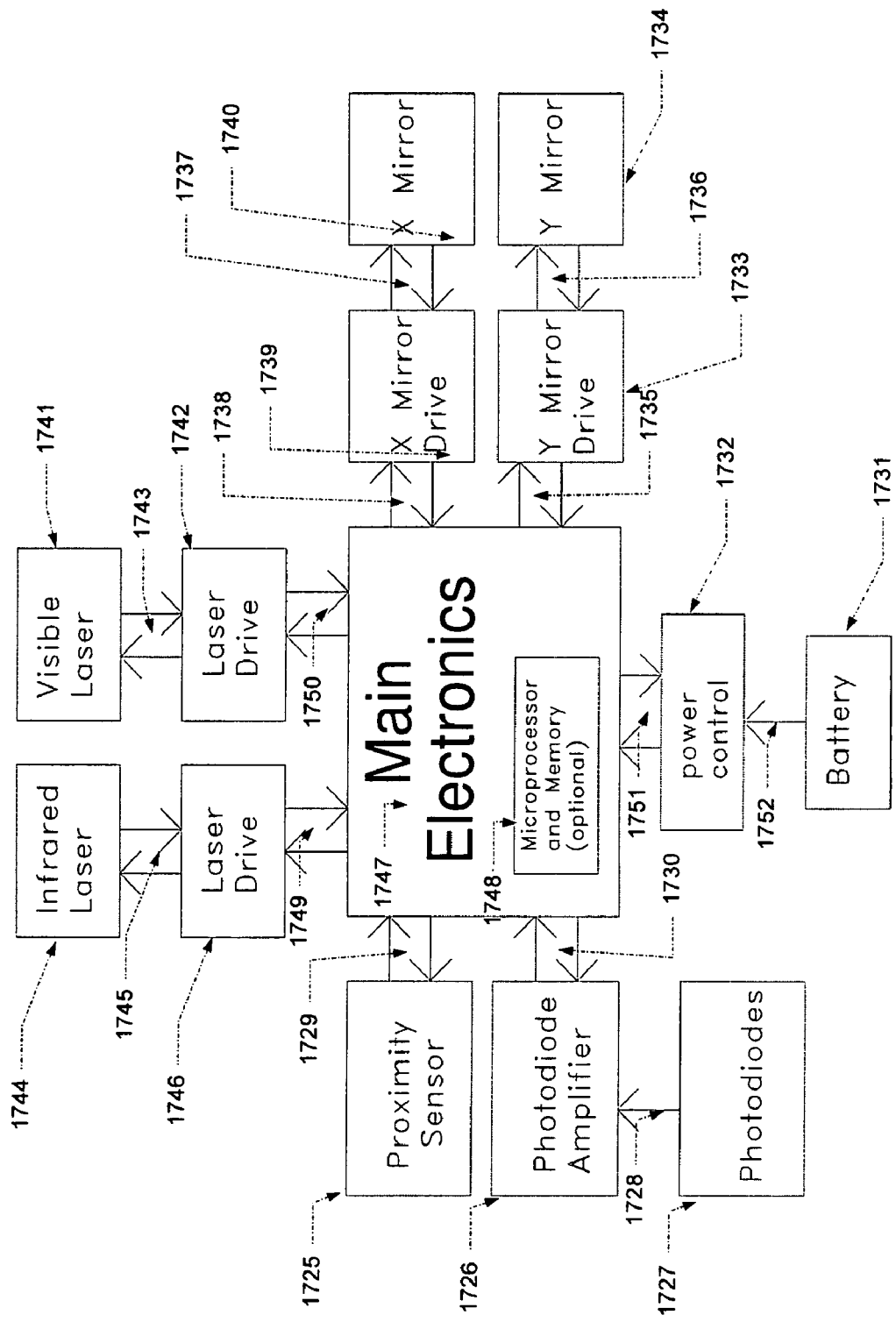
FIG. 29 shows a block diagram of a prototype embodiment of the invention.

Referring to FIG. 29, a block diagram of the invention is presented. The electronics system 1747 can be based on discrete electronic components or can have one or more microprocessors and memories 1748. In this embodiment, a small processor with on chip memory is dedicated to housekeeping functions including laser calibration, proximity sensing, and other system control and setup functions. Additional processing and memory components can be added to perform higher level functions like image-based vein detection.

In this embodiment, a raster pattern is implemented. A mirror drive subsystem 1738/1733 is controlled 1738/1735 by the electronics to drive the X mirror 1740 at a higher speed than the Y mirror 1734 to create the raster pattern. The electronics will control mirror on and off, and the mirror will report back when it begins its scan. The mirror drive systems 1739/1733 provides the drive waveform to the mirrors 1740/1734 that cause them to oscillate at the proper speed and in synchrony. This consists of sine wave to the mirrors. The drive circuitry also contains detection circuitry that uses a feedback path 1737/1736 from the mirrors to detect that the mirrors are in motion. In this manner, if a mirror has failed to move, the engine can shut down the lasers to ensure user safety.

The lasers are also controlled by the main electronics 1747 through a set of drive circuits 1746/1742. These circuits provide the ability to set the intensity of the lasers 1744/1741 from off through maximum intensity. In this embodiment, the lasers contain internal mirrors for calibration and which are read back from the lasers 1745/1743 and through the drive circuits 1748/1750 into the main electronics. The reverse path is used to control the drivers and lasers.

In this embodiment, a proximity sensor 1725 to detect that there is a surface within working range. The main electronics reads 1729 the sensor to ensure that the lasers are not turned on if there is an object either too close or no object within proximity of the front face of the scanner.

The photo detection subsystem consists of a pair of photo diodes 1727 and an amplifier 1726 that is fed through 1730 the main electronics for vein detection. A control for setting gain is provided through 1730.

Since this is a portable device, power is provided from a battery 1731, which provides 1752 power to a control circuit 1732 which provides voltage regulation and delivers 1751 the appropriate voltages to the electronics

We claim:
1. A miniature vein enhancer comprising:
 a single laser configured to emit a beam of light at a selective wavelength permitting differential absorption by blood and surrounding tissue;
 a beam steering assembly configured to receive and transmit said beam of laser light in a selected pattern directly onto a three-dimensional body target area and thereby form a visual contrast between one or more subcutaneous blood vessels and the surrounding tissue of the target area, said visual contrast being formed directly on the three-dimensional body target area to be perceivable thereon by the naked eye, said visual contrast comprising differing amounts of reflected laser light by one or more blood vessels absorbing more of said selective wavelength of laser light to create one or more darker areas identifying locations of the one or more blood vessels, and more light being reflected by the tissue surrounding the one or more blood vessels to create lighter areas;
 a photo detector configured to be responsive to said reflected laser light and to generate a detector output based on a received instantaneous representation of said visual contrast formed by said photo detector of said reflected laser light;
 a detection circuit configured to receive said detector output and to generate a control output therefrom;
 a power supply configured to provide power to said single laser and further configured to receive said control output;
 wherein when said detection circuit detects changes in the amplitude of light in said instantaneous representation corresponding to a blood vessel being detected, said detection circuit is configured to transmit a control output such that power is increased to said single laser by said power supply to thereby increase an intensity of said emitted beam of laser light to improve visibility of said one or more veins; and
 wherein when said detection circuit detects no changes in said amplitude in said instantaneous representation corresponding to no blood vessel being detected, said detection circuit is configured to transmit a control output such that power is decreased to said single laser by said power supply to thereby decrease an intensity of said emitted beam of laser light to be dimly visible but sufficient for further detection.

2. The miniature vein enhancer according to claim 1 wherein said selective wavelength comprises a wavelength in the range of 600 nm to 638 nm.

3. The miniature vein enhancer according to claim 2 wherein said selective wavelength is 635 nm.

4. The miniature vein enhancer according to claim 1 wherein said beam steering assembly comprises one or more fixed or moving mirrors.

5. The miniature vein enhancer according to claim 1 wherein said power supply is further configured to modulate an intensity of said single laser as a function of time by increasing or decreasing power to selectively scan at a variable depth for the one or more blood vessels; and wherein said modulation producing said selective scanning comprises a series of short duration pulses of higher intensity light for detection but being too short in duration for an eye of a user to detect, with each said short duration pulse being followed by a respective longer period of a lesser intensity of light being emitted to optimize said visual contrast.

6. The miniature vein enhancer according to claim 1 wherein said detection circuit is further configured to determine a reflectivity baseline of said body target area for an individual, said baseline being based upon one or more of: a skin color, a skin condition, and a position of said target area on said body.

7. A miniature vein enhancing system comprising:
a single laser configured to emit a beam of light at a selective wavelength permitting differential absorption,
a beam steering assembly comprising one or more moving mirrors configured to receive and selectively transmit said beam of laser light in a pattern onto a three-dimensional body target area, thereby creating a pattern of light directly on the three-dimensional target area such that said selective wavelength forms a three-dimensional contrast being visible to the unaided human eye and being perceived directly on the three-dimensional target area, said contrast comprising one or more darker areas identifying locations of one or more blood vessels within the target area with lighter areas identifying tissue surrounding the one or more blood vessels;
a photo detector configured to receive light reflected from the target area and transmit an output therefrom;
one or more discrete electronic components or a microprocessor, the output of said photo detector being fed into said one or more discrete electronic components or said microprocessor, wherein said one or more discrete electronic components or said microprocessor is configured to determine changes in the amplitude of light reflected from the target area to detect a relative amount of blood indicating a blood vessel and further configured to generate a control output based on the determination of the indication of a blood vessel;
a power supply configured to modulate power to said single laser to increase or decrease the intensity of said beam of light based on said control output.

8. The miniature vein enhancing system according to claim 7 wherein said one or more discrete electronic components or said microprocessor is further configured such that when no changes in amplitude of reflected light is detected, said control output causes said power supply to reduce the power to said single laser.

9. The miniature vein enhancing system according to claim 7 wherein said discrete electronic components or said microprocessor is further configured to control said power supply to cause said single laser to emit a very short pulse of high intensity light for detection of the one or more blood vessels but being imperceptible to a user, wherein said short pulse is followed by a respectively longer pulse of a lesser intensity of light being emitted to improve said contrast between blood vessels and the tissue surrounding the one or more blood vessels, said respective longer pulse being visibly perceptible to a user.

10. The miniature vein enhancing system according to claim 7 wherein said selective wavelength comprises a wavelength in the range of 600 nm to 638 nm.

11. A miniature vein enhancer comprising:
a single laser configured to emit a beam of light at a selective wavelength permitting differential absorption,
a beam steering assembly comprising one or more fixed or moving mirrors configured to receive and selectively transmit said beam of laser light in a pattern onto a three-dimensional body target area, thereby creating a pattern of light directly on the three-dimensional target area such that said selective wavelength forms a three-dimensional contrast being visible to the unaided human eye and being perceived directly on the three-dimensional target area, said contrast comprising one or more darker areas identifying locations of one or more veins within the target area with lighter areas identifying tissue surrounding the one or more veins;
a photo detector configured to receive light reflected from the target area and to generate a detector output therefrom;
a detection circuit configured to receive said detector output and to determine changes in the amplitude of light reflected from the target area to detect a relative amount of blood, said detection circuit being configured to generate a control output;
a power supply configured to receive said control output and to supply power to said single laser; and
wherein when a vein is detected by said detection circuit, said control output causes power to said single laser from said power supply to be increased, thereby increasing the intensity of said beam of laser light.

12. A miniature vein enhancer comprising:
a single laser configured to emit a beam of light at a selective wavelength permitting differential absorption,
a beam steering assembly comprising one or more fixed or moving mirrors configured to receive and selectively transmit said beam of laser light in a pattern onto a three-dimensional body target area, thereby creating a pattern of light directly on the three-dimensional target area such that said selective wavelength forms a three-dimensional contrast being visible to the unaided human eye and being perceived directly on the three-dimensional target area, said contrast comprising one or more darker areas identifying locations of one or more veins within the target area with lighter areas identifying tissue surrounding the one or more veins;
a photo detector configured to receive light reflected from the target area and to generate a detector output therefrom;
a detection circuit configured to receive said detector output and to determine changes in the amplitude of light reflected from the target area to detect a relative amount of blood, said detection means being adapted to generate a control output;
a power supply configured to receive said control output and to supply power to said single laser; and
wherein when a vein is detected by said detection means, said control output causes power to said single laser from said power supply to be increased, thereby increasing the intensity of said beam of laser light.

* * * * *